(12) United States Patent
Peartree et al.

(10) Patent No.: US 7,695,487 B2
(45) Date of Patent: Apr. 13, 2010

(54) BALLOON DISSECTION APPARATUS

(75) Inventors: Kenneth A. Peartree, Los Altos, CA (US); Thomas J. Palermo, San Jose, CA (US); Shigeru Tanaka, Half Moon Bay, CA (US); Ferolyn T. Powell, San Francisco, CA (US)

(73) Assignee: General Surgical Innovations, Inc., North Haven, CT (US)

( * ) Notice: Subject to any disclaimer, the term of this patent is extended or adjusted under 35 U.S.C. 154(b) by 1274 days.

(21) Appl. No.: 10/422,874

(22) Filed: Apr. 24, 2003

(65) Prior Publication Data

US 2003/0187472 A1    Oct. 2, 2003

Related U.S. Application Data

(63) Continuation of application No. 09/415,336, filed on Oct. 8, 1999, now Pat. No. 6,592,602.

(51) Int. Cl.
*A61B 17/00* (2006.01)

(52) U.S. Cl. .................. 606/190; 604/165.02

(58) Field of Classification Search ............. 606/190; 128/898; 604/165.03, 18, 158–172, 165.01–165.02
See application file for complete search history.

(56) References Cited

U.S. PATENT DOCUMENTS

| | | | |
|---|---|---|---|
| 1,060,350 A | 4/1913 | Miller |
| 1,213,005 A | 1/1917 | Pillsbury |
| 1,275,520 A | 8/1918 | Bell |
| 1,947,649 A | 2/1934 | Kadavy |
| 2,663,020 A | 12/1953 | Cushman |
| 2,936,760 A | 5/1960 | Gants |
| 3,039,468 A | 6/1962 | Price |
| 3,545,443 A | 12/1970 | Ansari |
| 3,626,949 A | 12/1971 | Shute |
| 3,774,596 A | 11/1973 | Cook |
| 3,782,370 A | 1/1974 | McDonald |
| 3,800,788 A | 4/1974 | White |

(Continued)

FOREIGN PATENT DOCUMENTS

AU    B-516114    5/1981

(Continued)

OTHER PUBLICATIONS

Ed. G. Berci, Endoscopy, Appleton-Century-Crofts, 1976, pp. 382-385 and 412.

(Continued)

*Primary Examiner*—Todd E Manahan
*Assistant Examiner*—Katherine M Dowe

(57) ABSTRACT

Apparatus for creating an anatomic space in tissue in a body including an introducer device having a tubular member with a bore extending therethrough. A tunneling shaft assembly is slidably mounted in the bore of the introducer device. The tunneling shaft assembly includes a tunneling shaft having proximal and distal extremities. A blunt tip is secured to the distal extremity of the tunneling shaft. A balloon assembly is provided. The balloon assembly is removably secured to the tunneling shaft. The balloon assembly includes a deflated collapsed balloon. A sheath encloses the balloon and is carried by the tunneling shaft. The sheath has a weakened region extending longitudinally thereof permitting the sheath to be removed to release the balloon.

26 Claims, 33 Drawing Sheets

U.S. PATENT DOCUMENTS

| | | | |
|---|---|---|---|
| 3,831,587 A | 8/1974 | Boyd | |
| 3,863,639 A | 2/1975 | Kleaveland | |
| 3,882,852 A | 5/1975 | Sinnreich | |
| 3,961,632 A | 6/1976 | Moossun | |
| RE29,207 E | 5/1977 | Bolduc et al. | |
| 4,077,412 A | 3/1978 | Moossun | |
| 4,083,369 A | 4/1978 | Sinnreich | |
| 4,137,906 A | 2/1979 | Akiyama et al. | |
| 4,183,102 A | 1/1980 | Guiset | |
| 4,217,889 A | 8/1980 | Radovan et al. | |
| 4,240,433 A | 12/1980 | Bordow | |
| 4,243,050 A | 1/1981 | Littleford | |
| 4,254,762 A | 3/1981 | Yoon | |
| 4,271,839 A | 6/1981 | Fogarty et al. | |
| 4,276,874 A | 7/1981 | Wolvek et al. | |
| 4,291,687 A | 9/1981 | Sinnreich | |
| 4,312,353 A | 1/1982 | Shahbabian | |
| 4,318,410 A | 3/1982 | Chin | |
| 4,357,940 A | 11/1982 | Muller | |
| 4,411,654 A | 10/1983 | Boarini et al. | |
| 4,430,076 A | 2/1984 | Harris | |
| 4,447,227 A | 5/1984 | Kotsanis | |
| 4,490,137 A | 12/1984 | Moukheibir | |
| 4,493,711 A | 1/1985 | Chin et al. | |
| 4,496,345 A | 1/1985 | Hasson | |
| 4,535,773 A | 8/1985 | Yoon | |
| 4,574,806 A | 3/1986 | McCarthy | |
| 4,581,025 A | 4/1986 | Timmermans | |
| 4,596,554 A | 6/1986 | Dastgeer | |
| 4,598,699 A | 7/1986 | Garren et al. | |
| 4,601,710 A | 7/1986 | Moll | |
| 4,644,936 A | 2/1987 | Schiff | |
| 4,654,030 A | 3/1987 | Moll et al. | |
| 4,685,447 A | 8/1987 | Iversen et al. | |
| 4,709,697 A | 12/1987 | Muller | |
| 4,738,666 A | 4/1988 | Fuqua | |
| 4,744,363 A | 5/1988 | Hasson | |
| 4,769,038 A | 9/1988 | Bendavid et al. | |
| 4,772,266 A | 9/1988 | Groshong | |
| 4,775,371 A | 10/1988 | Muller, Jr. | |
| 4,779,611 A | 10/1988 | Grooters et al. | |
| 4,784,133 A | 11/1988 | Mackin | |
| 4,793,348 A | 12/1988 | Palmaz | |
| 4,798,205 A | 1/1989 | Bonomo et al. | |
| 4,863,440 A | 9/1989 | Chin | |
| 4,919,152 A | 4/1990 | Ger | |
| 4,944,443 A | 7/1990 | Oddsen et al. | |
| 4,966,583 A | 10/1990 | Debbas | |
| 4,984,564 A | 1/1991 | Yuen | |
| 5,002,557 A | 3/1991 | Hasson | |
| 5,007,898 A | 4/1991 | Rosenbluth et al. | |
| 5,029,574 A | 7/1991 | Shimamura et al. | |
| 5,082,005 A | 1/1992 | Kaldany | |
| 5,083,576 A | 1/1992 | Ruiz-Razura et al. | |
| 5,122,122 A | 6/1992 | Allgood | |
| 5,122,155 A | 6/1992 | Eberbach | |
| 5,141,515 A | 8/1992 | Eberbach | |
| 5,163,949 A | 11/1992 | Bonutti | |
| 5,176,128 A | 1/1993 | Andrese | |
| 5,176,692 A | 1/1993 | Wilk et al. | |
| 5,176,697 A | 1/1993 | Hasson et al. | |
| 5,183,463 A | 2/1993 | Debbas | |
| 5,183,464 A | 2/1993 | Dubrul et al. | |
| 5,188,630 A | 2/1993 | Christoudias | |
| 5,195,507 A | 3/1993 | Bilweis | |
| 5,197,948 A | 3/1993 | Ghodsian | |
| 5,197,971 A | 3/1993 | Bonutti | |
| 5,269,753 A | 12/1993 | Wilk | |
| 5,295,994 A | 3/1994 | Bonutti | |
| 5,309,896 A | 5/1994 | Moll et al. | |
| 5,318,586 A | 6/1994 | Ereren | |
| 5,331,975 A | 7/1994 | Bonutti | |
| 5,334,146 A | 8/1994 | Ozasa | |
| 5,359,995 A | 11/1994 | Sewell, Jr. | |
| 5,425,357 A | 6/1995 | Moll et al. | |
| 5,478,320 A | 12/1995 | Trotta | |
| 5,496,345 A | 3/1996 | Kieturakis et al. | |
| 5,514,153 A | 5/1996 | Bonutti | |
| 5,540,711 A * | 7/1996 | Kieturakis et al. | 606/192 |
| 5,575,759 A | 11/1996 | Moll et al. | |
| 5,593,418 A | 1/1997 | Mollenauer | |
| 5,601,581 A | 2/1997 | Fogarty et al. | |
| 5,601,589 A | 2/1997 | Fogarty et al. | |
| 5,607,443 A | 3/1997 | Kieturakis et al. | |
| 5,634,937 A | 6/1997 | Mollenauer et al. | |
| 5,653,726 A | 8/1997 | Kieturakis | |
| 5,658,306 A * | 8/1997 | Kieturakis et al. | 606/184 |
| 5,667,479 A | 9/1997 | Kieturakis | |
| 5,681,342 A | 10/1997 | Benchetrit | |
| 5,730,748 A | 3/1998 | Fogarty et al. | |
| 5,772,680 A | 6/1998 | Kieturakis et al. | |
| 5,779,728 A | 7/1998 | Lunsford et al. | |
| 5,797,947 A | 8/1998 | Mollenauer | |
| 5,814,060 A | 9/1998 | Fogarty et al. | |
| 5,836,961 A | 11/1998 | Kieturakis et al. | |
| 5,860,997 A | 1/1999 | Bonutti | |
| 6,004,337 A | 12/1999 | Kieturakis et al. | |
| 6,159,219 A | 12/2000 | Ren | |
| 6,197,002 B1 * | 3/2001 | Peterson | 604/164.01 |
| 6,592,602 B1 * | 7/2003 | Peartree et al. | 606/170 |

FOREIGN PATENT DOCUMENTS

| | | |
|---|---|---|
| DE | A-2 847 633 | 5/1979 |
| DE | U 91-04-83 | 7/1991 |
| EP | A 0 010 650 | 5/1980 |
| EP | A 0 246 086 | 11/1987 |
| EP | A 0 251 976 | 1/1988 |
| EP | A 2 275 230 | 7/1988 |
| EP | 0 573 273 A2 | 12/1993 |
| EP | 0 880 939 A1 | 2/1998 |
| FR | 2 474 304 | 7/1981 |
| FR | 2 646 088 | 10/1990 |
| FR | A 2 688 695 | 5/1992 |
| GB | A 2 071 502 | 9/1981 |
| RU | 797 668 | 1/1991 |
| WO | WO83/03188 | 9/1983 |
| WO | WO 93/11824 | 12/1992 |
| WO | WO93/09722 | 5/1993 |
| WO | WO 93/10850 | 6/1993 |
| WO | WO 99/12602 | 3/1999 |

OTHER PUBLICATIONS

H. Nagai et al., A New Method of Laparoscopic Cholecystectomy: An abdominal Wall Lifting Technique Without Pneumoperitoneum, Surgical Laparoscopy and Endoscopy, vol. 1, No. 2, 1991, p. 126.

M.M. Gazayedi, "The Gazayerli Endoscopic Retractor, Model 1;" Surgical Laparoscopy & Endoscopy, vol. 1 No. 2, pp. 98-100, Raven Press, New York, Jun. 1991.

* cited by examiner

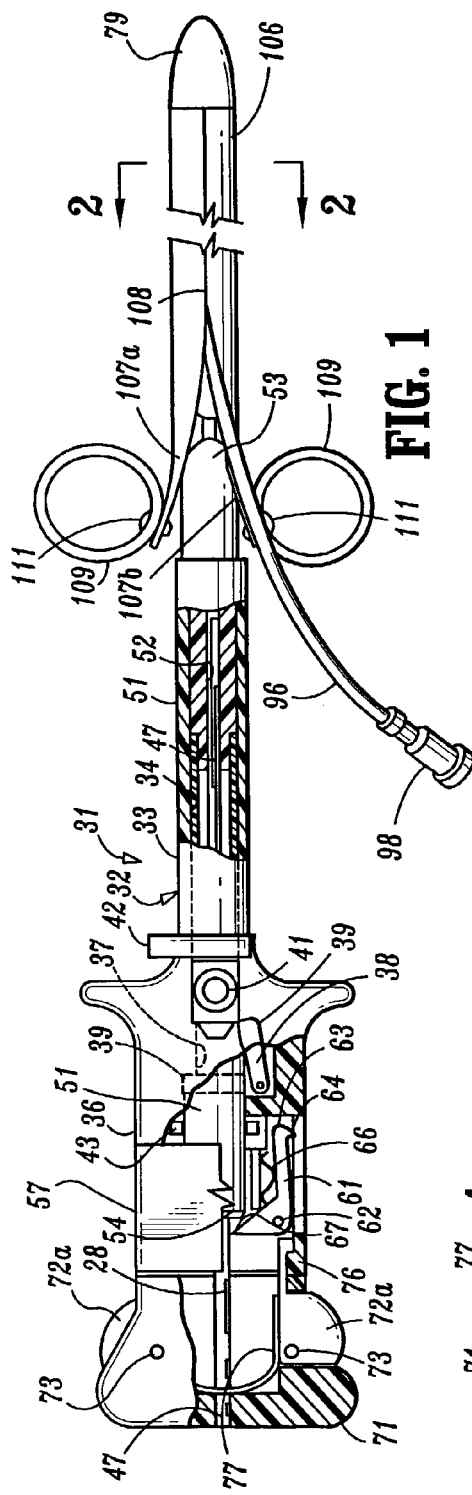
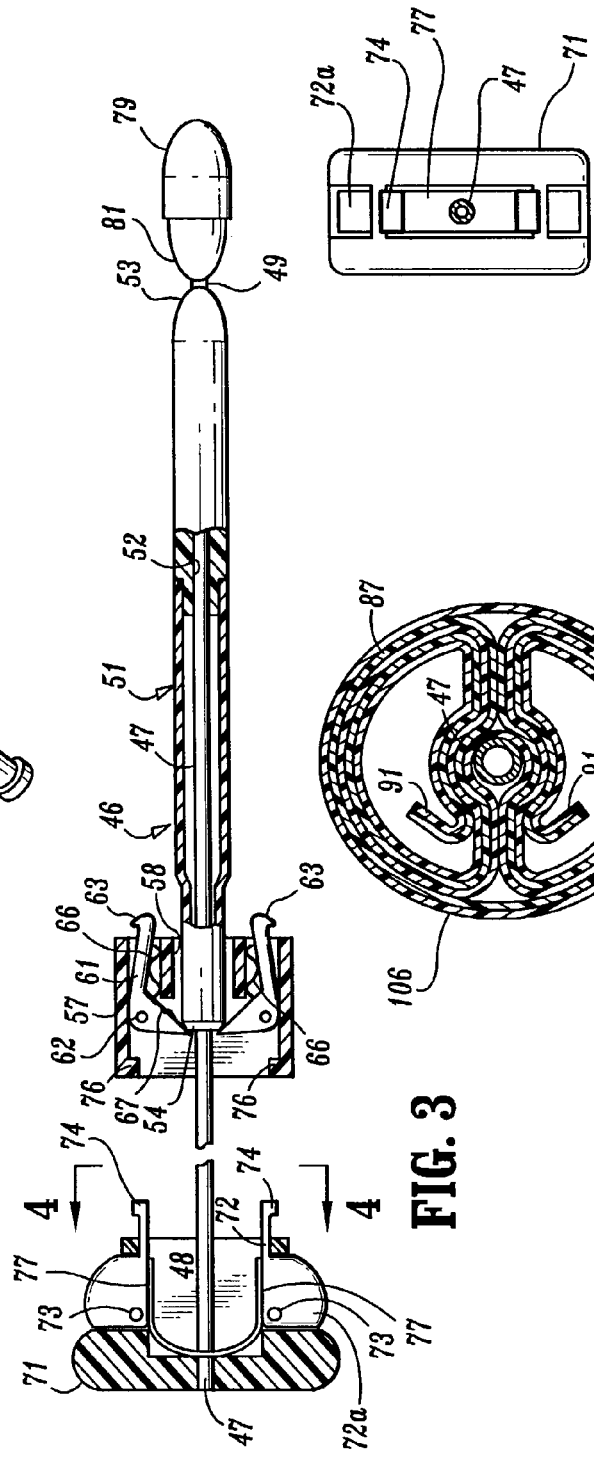
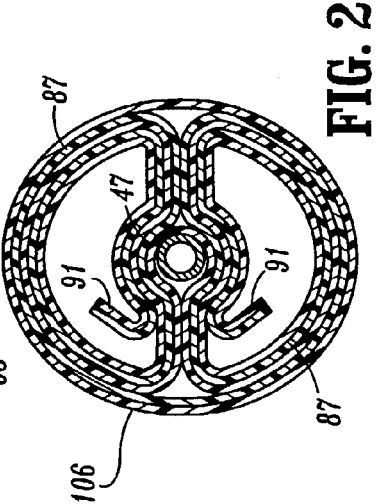
FIG. 1
FIG. 2
FIG. 3
FIG. 4

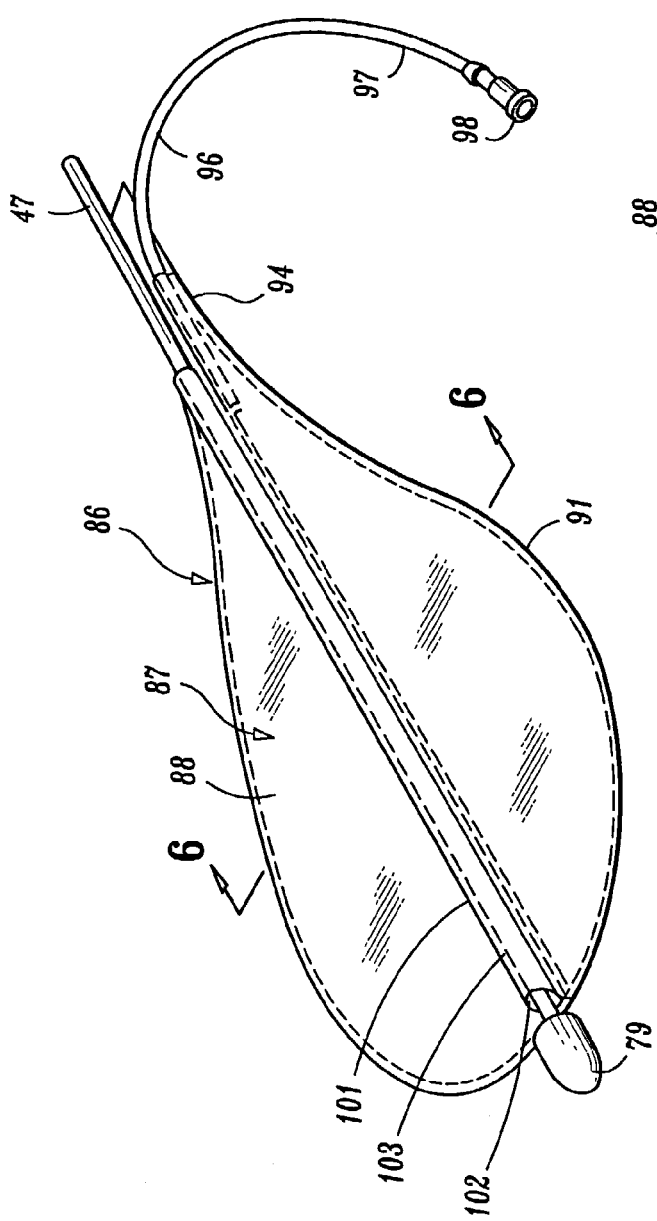
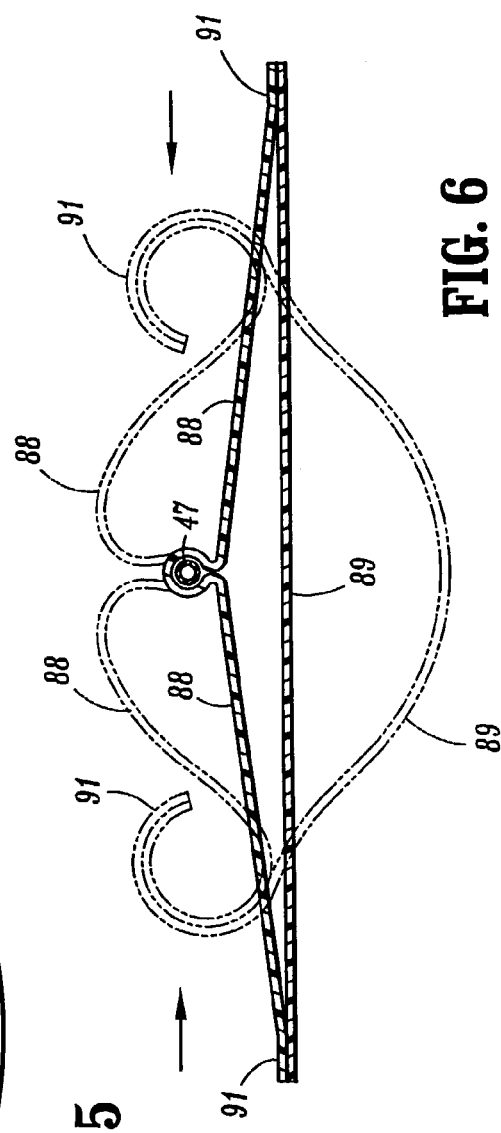

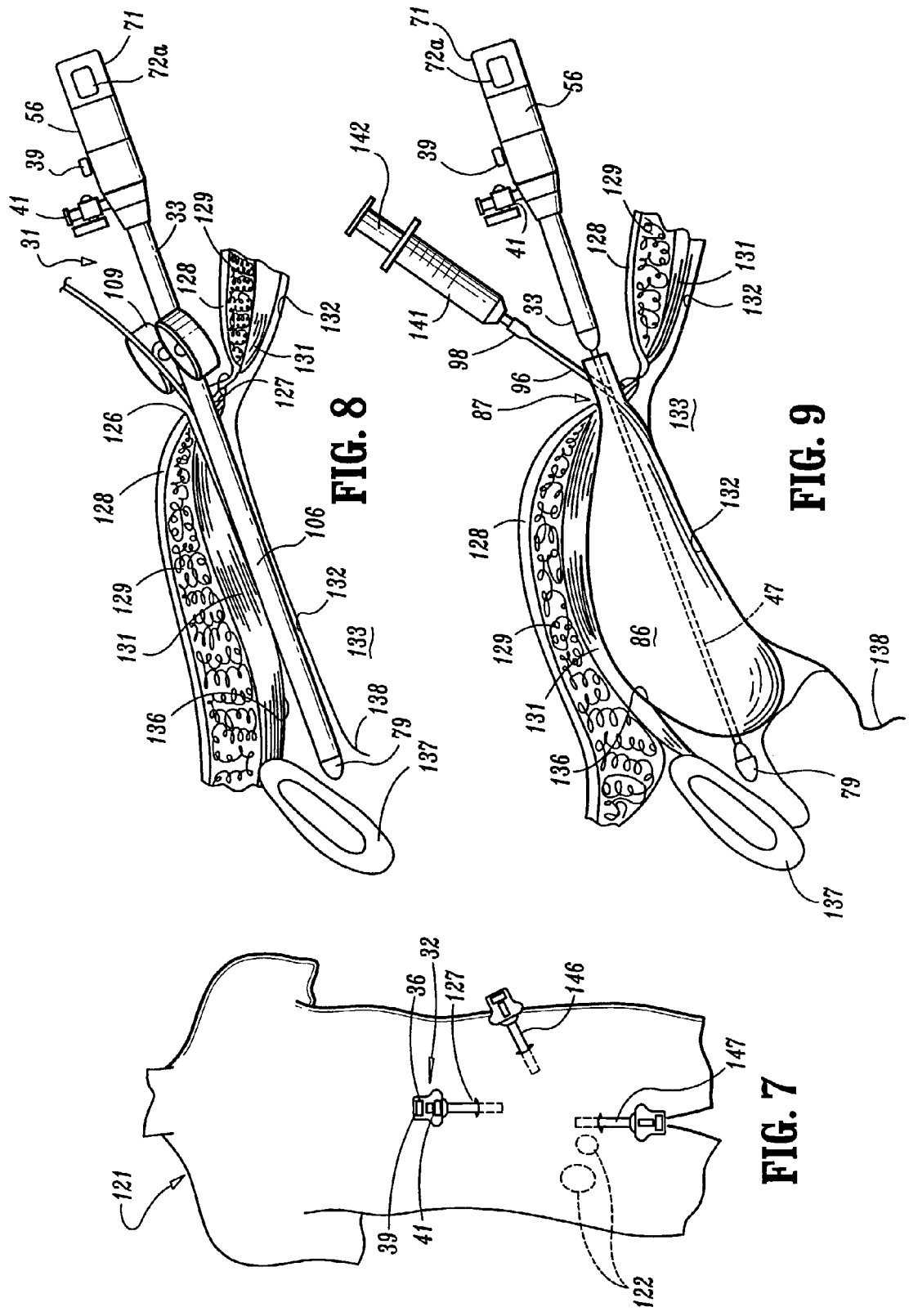

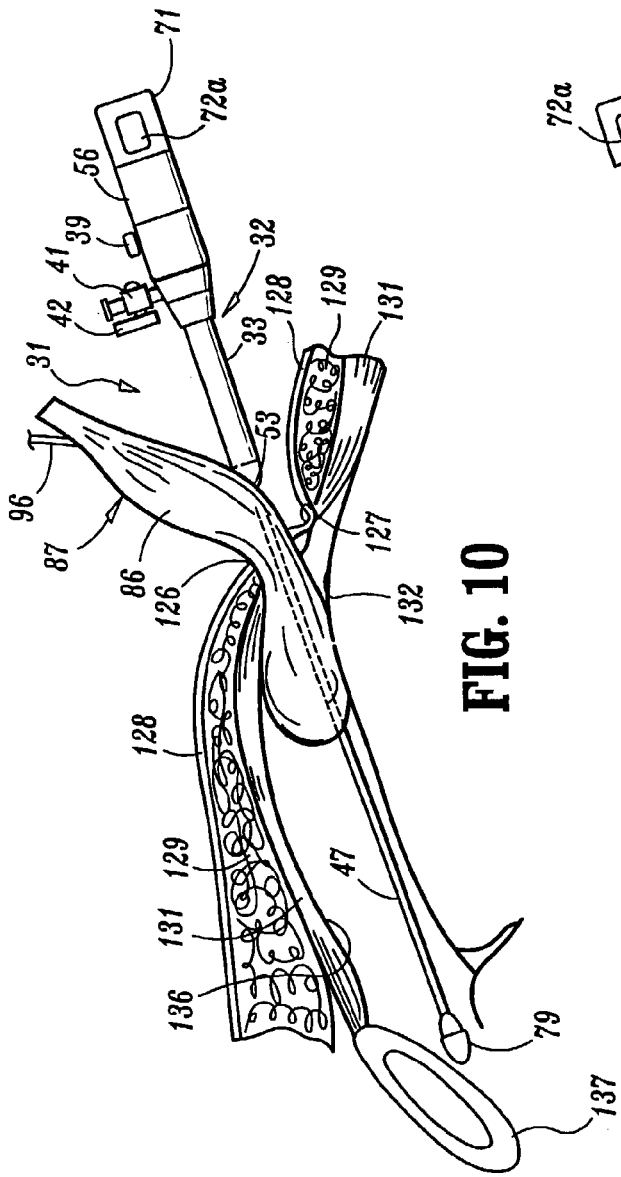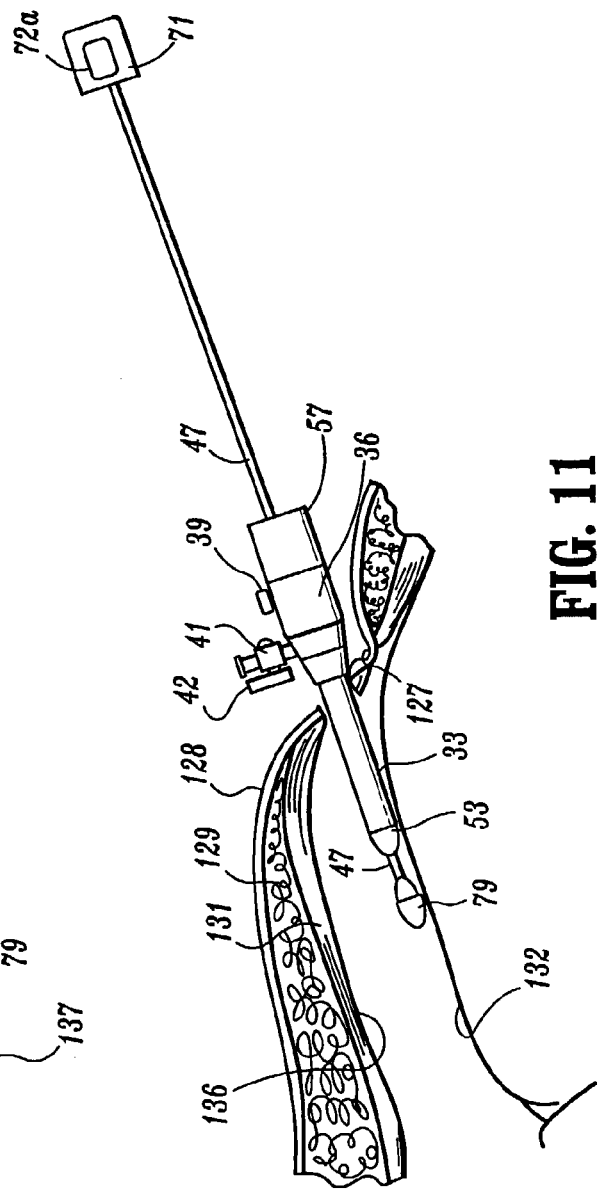
FIG. 10
FIG. 11

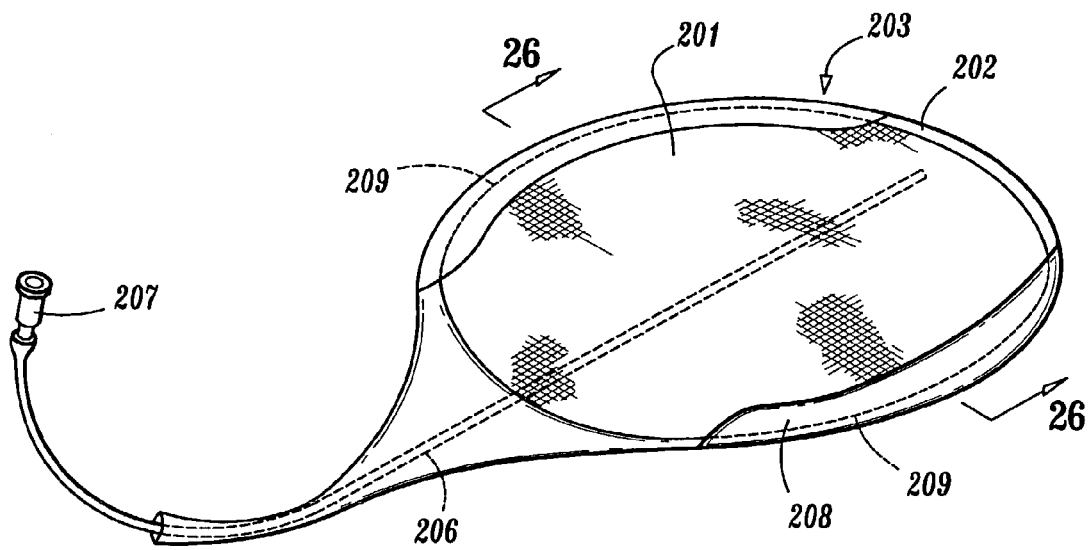
FIG. 25
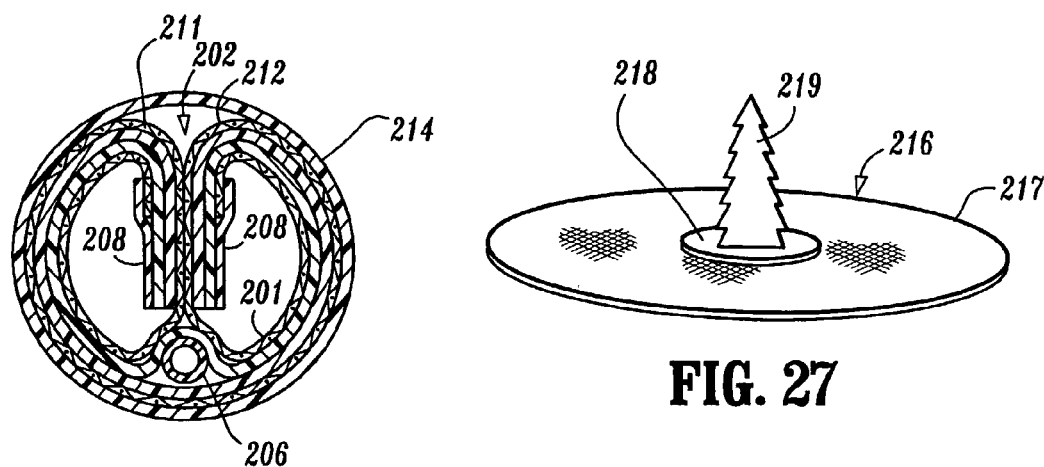
FIG. 26
FIG. 27
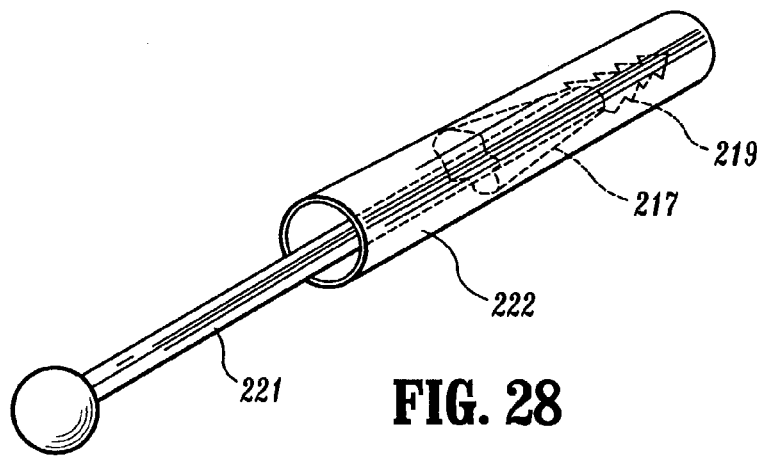
FIG. 28

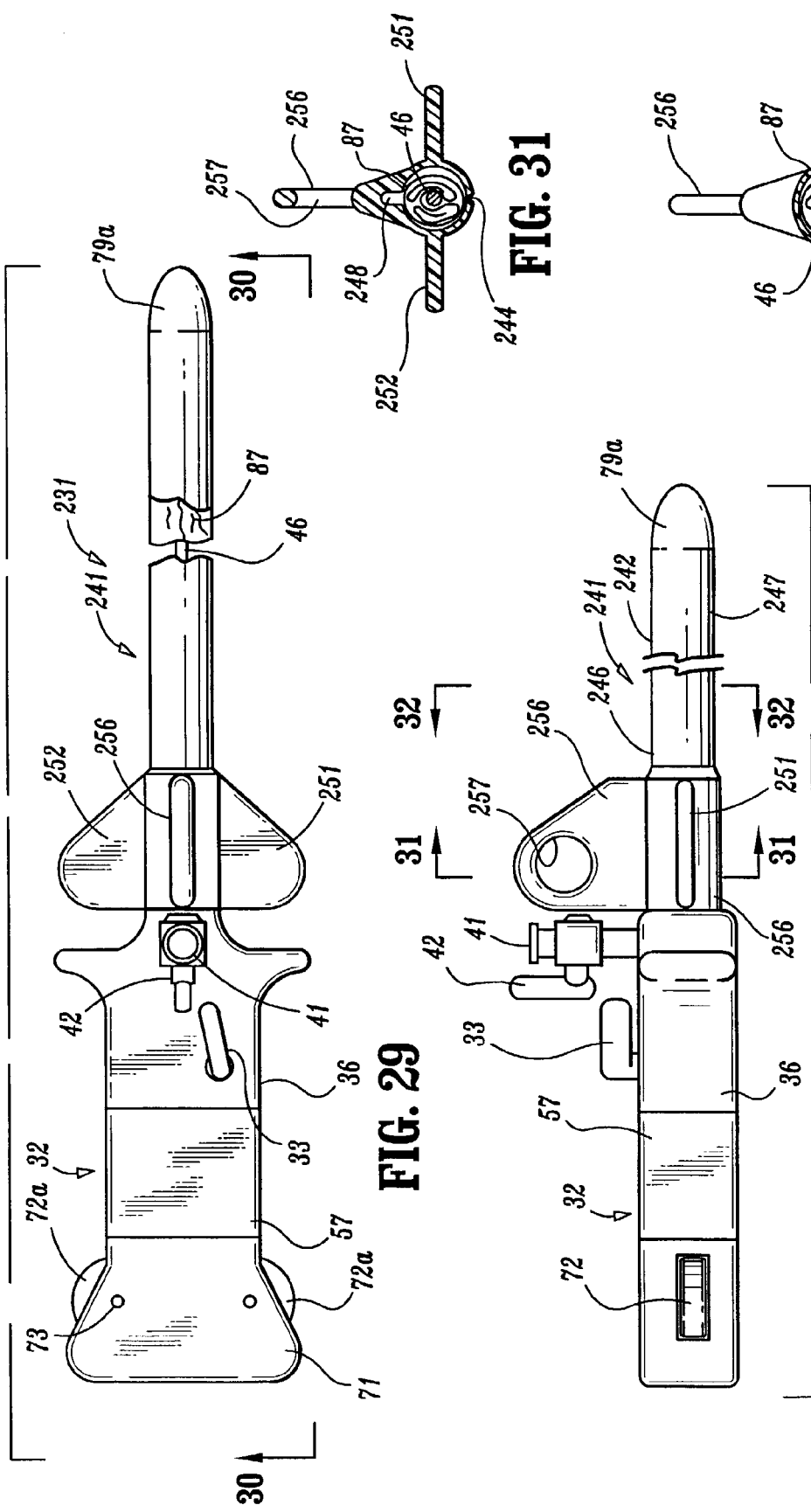

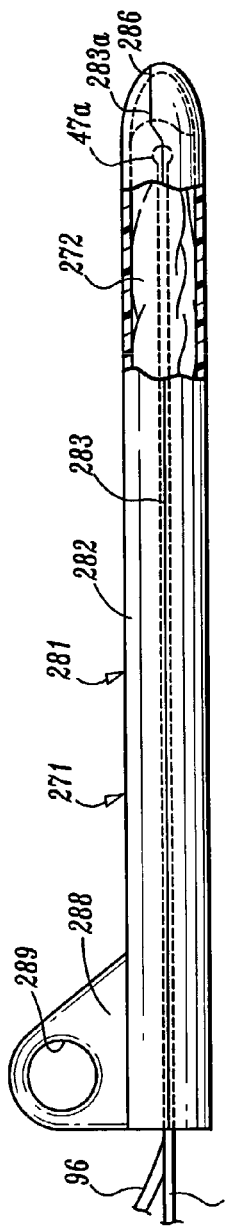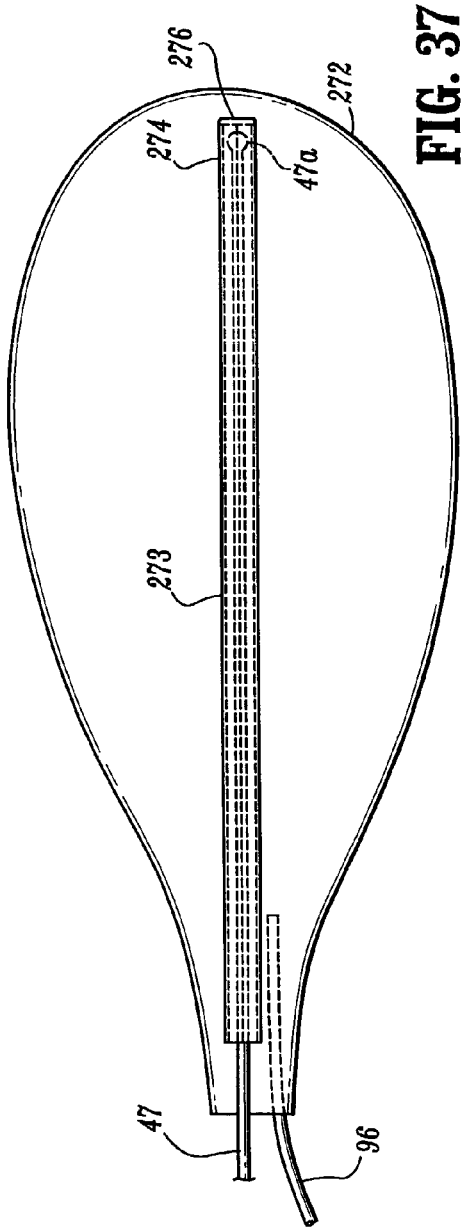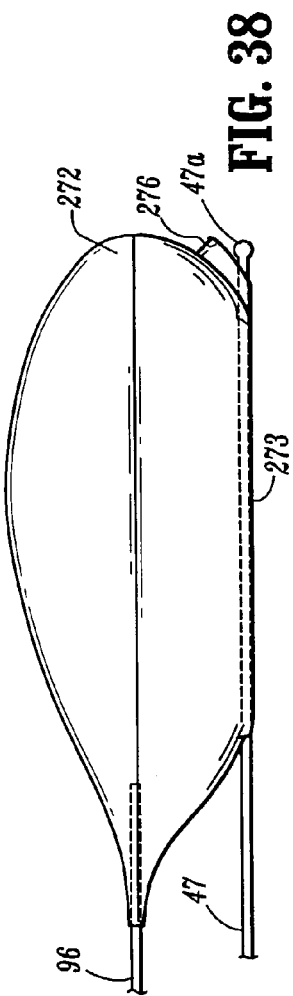

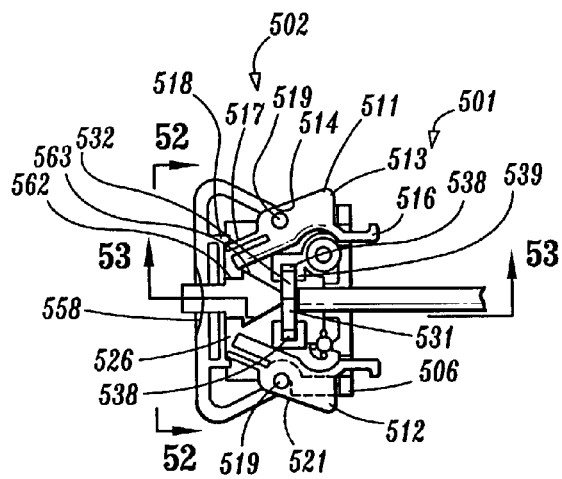
FIG. 51
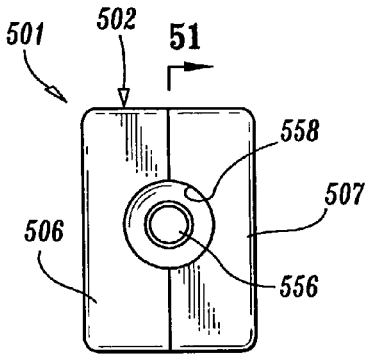
FIG. 52
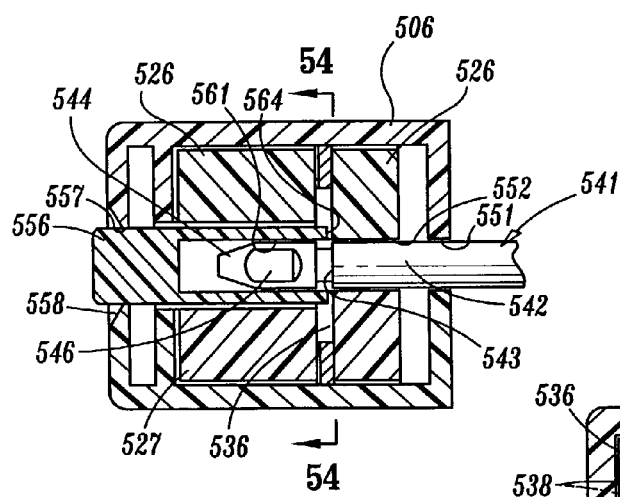
FIG. 53
FIG. 54
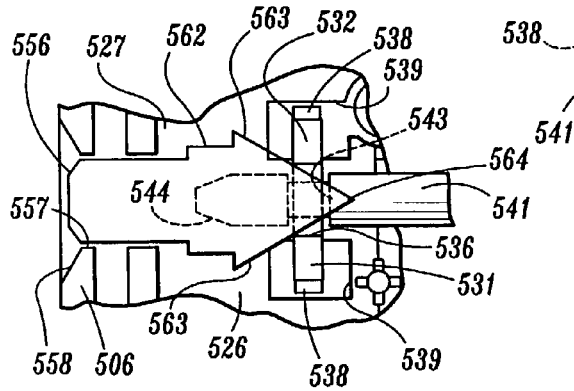
FIG. 55

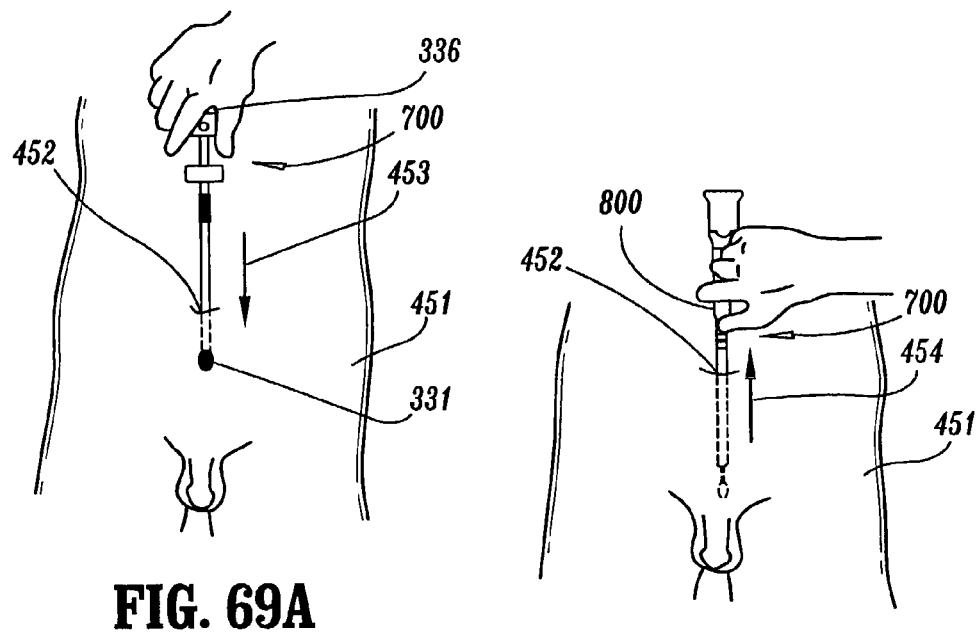
FIG. 69A
FIG. 69B
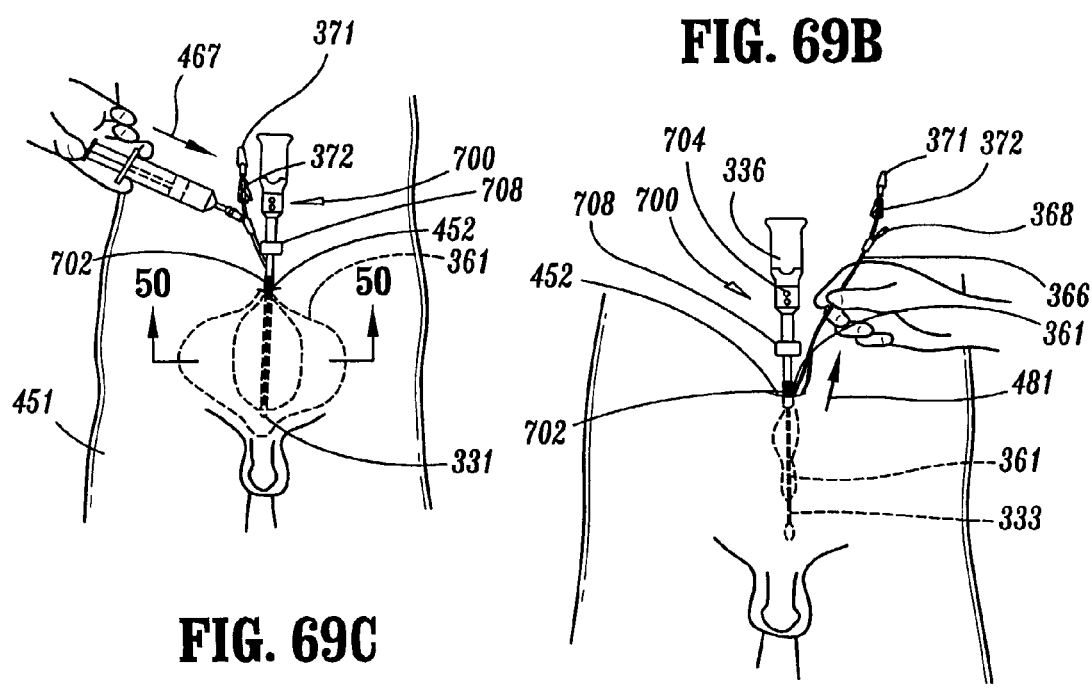
FIG. 69C
FIG. 69D

BALLOON DISSECTION APPARATUS

CROSS REFERENCE TO RELATED APPLICATIONS

This is a continuation of application Ser. No. 09/415,336, filed on Oct. 8, 1999 now U.S. Pat. No. 6,592,602. The disclosure of this prior application is hereby incorporated by reference in its entirety.

BACKGROUND OF INVENTION

This invention relates to an apparatus and method for developing an anatomic space for laparoscopic hernia repair and a patch for use therewith.

In the past, in developing spaces and potential spaces within a body, blunt dissectors or soft-tipped dissectors have been utilized to create a dissected space which is parallel to the plane in which the dissectors are introduced into the body tissue. This often may be in an undesired plane, which can lead to bleeding which may obscure the field and make it difficult to identify the body structures. In utilizing such apparatus and methods, attempts have been made to develop anatomic spaces in the anterior, posterior or lateral to the peritoneum. The same is true for pleural spaces and other anatomic spaces. Procedures that have been performed in such spaces include varicocele dissection, lymph node dissection, sympathectomy and hernia repair. In the past, the inguinal hernia repair has principally been accomplished by the use of an open procedure which involves an incision in the groin to expose the defect in the inguinal floor, remove the hernial sac and subsequently suture the ligaments and fascias together to reinforce the weakness in the abdominal wall. Recently, laparoscopic hernia repairs have been attempted by inserting laparoscopic instruments into the abdominal cavity through the peritoneum and then placing a mesh to cover the hernia defect. Hernia repair using this procedure has a number of disadvantages, principally because the mesh used for hernia repair is in direct contact with the structures in the abdominal cavity, as for example the intestines, so that there is a tendency for adhesions to form in between these structures. Such adhesions are known to be responsible for certain occasionally serious complications. Such a procedure is also undesirable because typically the patch is stapled into the peritoneum, which is a very thin unstable layer covering the inner abdomen. Thus, the stapled patch can tear away from the peritoneum or shift its position. Other laparoscopic approaches involve cutting away the peritoneum and stapling it closed. This is time consuming and involves the risk of inadvertent cutting of important anatomic structures. In addition, such a procedure is undesirable because it requires the use of a general anesthesia. There is therefore a need for a new and improved apparatus and method for developing an anatomic space and particularly for accomplishing hernia repair by laparoscopy.

SUMMARY OF THE INVENTION

In general, it is an object of the present invention to provide an apparatus and method for developing an anatomic space.

Another object of the invention is to provide an apparatus and method in which such an anatomic space is developed by applying perpendicular forces to create the anatomic space at the weakest plane to create a more natural, less traumatic and bloodless region in which to work.

Another object of the invention is to provide an apparatus and method to obtain surgical exposure in the preperitoneal space.

Another object of the invention is to provide an apparatus and method to create an extraperitoneal working space utilizing a balloon dissector.

Another object of the present invention is to provide an apparatus and method of the above character for developing an anatomic space for laparoscopic hernia repair through the anatomic space.

Another object of the invention is to provide an apparatus and method for decreasing the time and risk associated with creating a preperitoneal working space.

Another object of the present invention is to provide an apparatus and method of the above character for developing an anatomic space for laparoscopic hernia repair through the anatomic space.

Another object of the invention is to provide an apparatus and method of the above character which requires a minimally invasive procedure.

Another object of the invention is to provide an apparatus and method of the above character which can be accomplished without the use of a general anesthesia.

Another object of the invention is to provide an apparatus and method of the above character which can be accomplished with a spinal or epidural anesthesia.

Another object of the invention is to provide an apparatus and method of the above character which provides substantially reduced medical costs and a greatly reduced patient recovery time.

Another object of the invention is to provide an apparatus of the above character which is relatively simple and compact.

Another object of the invention is to provide an apparatus and method of the above character which can be readily utilized by surgeons.

Another object of the invention is to provide a patch for use in the apparatus which is firmly secured during the hernia repair.

Another object of the invention is to provide a balloon which has a modified symmetric manta ray configuration to aid in providing the desired configuration for the extraperitoneal working space for hernia repair.

Another object of the invention is to provide a balloon dissection apparatus in which the balloon cover is detachably secured to the obturator so that the balloon dissection device is relatively rigid to permit the balloon dissection apparatus to be grasped by the handle to operate the same during dissection.

Another object of the invention is to provide a balloon dissection apparatus of the above character in which a precise release mechanism is provided for releasing the balloon cover from the obturator so that the surgeon can be assured that the balloon cover has been released before it is removed to release the balloon.

Another object of the invention is to provide a balloon dissection apparatus of the above character in which the guide rod or obturator remain in place to maintain ready access to the extraperitoneal working space.

Another object of the invention is to provide a balloon dissection apparatus of the above character in which certain of the parts which are to be moved relative to other parts are color coded to aid the surgeon in use of the apparatus.

Another object of the apparatus is to provide an introducer member which is provided with a tip having an inclined surface.

Another object of the invention is to provide a balloon dissection apparatus which is provided with a blunt tip which has a diameter which is less than the diameter of the cannula tube.

Another object of the invention is to provide a balloon dissection apparatus of the above character in which at least a part of the same can be sterilized and reused.

Additional objects and features of the invention will appear from the following description in which the preferred embodiments are set forth in detail in conjunction with the accompanying drawings.

BRIEF DESCRIPTION OF THE DRAWINGS

FIG. 1 is a side elevational view partially in cross-section of a laparoscopic apparatus incorporating the present invention.

FIG. 2 is a cross-sectional view taken along the 2-2 of FIG. 1.

FIG. 3 is a side elevational view partially in cross-section of the tunneling shaft forming a part of the apparatus shown in FIG. 1 after it has been removed from the apparatus shown in FIG. 1.

FIG. 4 is a cross-sectional view taken along the line 4-4 of FIG. 3.

FIG. 5 is an isometric view of the inflatable balloon utilized in the apparatus in FIG. 1 secured to the tunneling rod.

FIG. 6 is a cross-sectional view taken along the line 6-6 of FIG. 5, and showing by dotted lines the manner in which the balloon as it unfolds develops the anatomic space.

FIG. 7 is a partial plan view of a prone human body, showing the lower abdomen showing the manner in which the laparoscopic apparatus of the present invention is utilized for performing a hernia repair through the preperitoneal space.

FIG. 8 is a sagittal view of the lower abdominal cavity of the human being shown in FIG. 7 showing the apparatus of the present invention introduced into the preperitoneal space.

FIG. 9 is a view similar to FIG. 8 but showing the sleeve removed from the apparatus and with the balloon inflated.

FIG. 10 is a sagittal view similar to FIG. 8 showing the balloon deflated and being removed.

FIG. 11 is a sagittal view similar to FIG. 8 showing removal of the tunnelling shaft.

FIG. 25 is an isometric view of another embodiment of a balloon and patch for use with the apparatus of the present invention.

FIG. 26 is a rolled-up cross-sectional view of the balloon and patch shown in FIG. 25.

FIG. 27 is an isometric view of another embodiment of a patch for use with the apparatus of the present invention.

FIG. 28 is an isometric view of the patch shown in FIG. 27 wrapped in an introducer assembly.

FIG. 29 is a top plan view of another embodiment of a laparoscopic apparatus incorporating the present invention.

FIG. 30 is a side elevational view taken along the line 30-30 of FIG. 29.

FIG. 31 is a cross-sectional view taken along the line 31-31 of FIG. 30.

FIG. 32 is a cross-sectional view taken along the line 32-32 of FIG. 30.

FIG. 36 is a side elevational view of another embodiment of a laparoscopic apparatus incorporating the present invention.

FIG. 37 is a plan view showing the balloon from the apparatus shown in FIG. 36 in an inflated condition and showing the tunneling rod mounted therein being prevented from being advanced beyond the distal extremity of the balloon.

FIG. 38 is a plan view showing the manner in which the balloon is separated from the tunneling rod as it is retracted.

FIG. 51 is a cross-sectional view taken along the line 51-51 of FIG. 52 showing another embodiment of a balloon dissection apparatus incorporating the present invention.

FIG. 52 is an end elevational view taken along the line 52-52 of FIG. 51.

FIG. 53 is an enlarged cross-sectional view taken along the line 53-53 of FIG. 51.

FIG. 54 is an enlarged cross-sectional view taken along the line 54-54 of FIG. 53.

FIG. 55 is an enlarged cross-sectional view of a portion of the view shown in FIG. 51 showing the latch members moved to permit removal of the guide rod.

FIG. 69A-69G illustrate use of the surgical dissector shown in FIGS. 56-68 in a laparoscopic hernia procedure.

DETAILED DESCRIPTION OF THE PREFERRED EMBODIMENT

Figure 15:
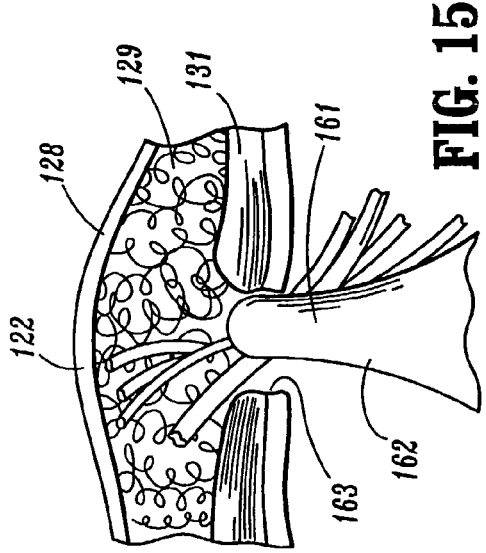
FIG. 15 is a sagittal view showing the hernia sac of hernia that is to be repaired.

In general, the apparatus of the present invention is used for insertion into a body to create an anatomic space. The apparatus is comprised of a tubular introducer member having a bore extending therethrough. A tunneling shaft is slidably mounted in the bore and has proximal and distal extremities including a bullet-shaped tip. A rounded tunneling member is mounted on the distal extremity of the tunneling shaft. An inflatable balloon is provided. Means is provided on the balloon for removably securing the balloon to the tunneling shaft. Means is also provided for forming a balloon inflation lumen for inflating the balloon. The balloon is wrapped on the tunneling shaft. A sleeve substantially encloses the balloon and is carried by the tunneling shaft. The sleeve is provided with a weakened region extending longitudinally thereof, permitting the sleeve to be removed whereby the balloon can be unwrapped and inflated so that it lies generally in a plane. The balloon as it is being inflated creates forces generally perpendicular to the plane of the balloon to cause pulling apart of the tissue along a natural plane to provide the anatomic space.

More in particular, as shown in the drawings, the apparatus or device 31 for creating such an anatomic space for use in a laparoscopic procedure (see FIG. 1) includes an introducer sleeve or device 32 which includes a tubular member 33 formed of a suitable material such as plastic which is provided with a bore 34 extending throughout the length thereof. A handle section 36 is mounted on one end of the tubular member 33 and is also formed of a suitable material such as plastic. It is provided with a bore 37 which is in communication with the bore 33. A flapper valve 38 is mounted within the section 36 and is movable between a position in which it closes off the bore 37 and position out of the way of the bore 37, by means of a finger operated actuator 39 mounted on the exterior of the section 36. A stopcock 41 is mounted on the section 36 and is in communication with the passage 37. A lever 42 is provided for opening and closing the stopcock 41.

A tunneling shaft assembly 46 is slidably mounted in the bores 37 and 34 of the introducer sleeve 32. The tunneling shaft assembly 46 includes a tunneling shaft or rod 47 formed of a suitable material such as stainless steel, of a suitable length, as for example 18 inches, and a suitable diameter of approximately ⅛ inch. The tunneling rod 47 is provided with proximal and distal extremities 48 and 49.

An introducer member 51 is slidably mounted on the tunneling shaft or rod 47 and is formed of a suitable material such as plastic. The introducer member 51 is substantially hollow as shown and is provided with a bore 52 through which the tunneling shaft 47 extends. The introducer member 51 is provided with a substantially hemispherical tip 53 to form a rounded protrusion or first obturator through which the rod 47 extends. The introducer member 51 has a length such that when it is introduced into the bore 34 of the introducer sleeve, it extends out of the distal extremity of the introducer sleeve 32, as shown particularly in FIG. 1. This diameter of the introducer member 51 is sized so that it can be slidably mounted in the bore 34. The other end of the introducer member 51 is provided with a chamfer 54.

A disk-type seal 43 having a central opening is provided in the section 36 in alignment with the bore 37, and is adapted to permit the introduction of the introducer member 51 therethrough.

The section 36 forms one part of a three-piece handle 56 of the laparoscopic apparatus 31 which is sized so that it is adapted to be grasped by the human hand. As can be seen particularly in FIG. 4, the handle 56 is generally rectangular in cross-section. The handle 56 is provided with an intermediate section 57 which has a bore 58 extending therethrough in registration with the bore 37 and has the same general diameter as the bore 37 so that the introducer member 51 can travel therethrough. The sections of the handle 56 can be characterized as having first, second and third sections, in which section 36 is the first section and intermediate section 57 is the second section. Latching means is provided for interconnecting the intermediate section 57 to the end section 36, and includes a pair of oppositely disposed latches 61 pivotally mounted on the pins 62 in the intermediate section 57. Each of the latches 61 is provided with a latch portion 63 adapted to engage a protrusion 64 provided on the end section 36, and is yieldably urged into engagement therewith by a spring 66. Each of the latches is provided with a cam surface 67 which is adapted to be engaged by the chamfer 54 of the introducer member 51 to cam the latch portion 63 out of engagement with the protrusion 64 to release the intermediate section 57 from the end section 36 for a purpose hereinafter described.

The handle 56 also includes another end section 71, which can also be characterized as the third section, which is secured to the proximal extremity of the tunneling shaft or rod 47. A pair of latches 72 are provided in the end section 71 and are pivotally mounted on pins 73. The latches 72 are provided with latch portions 74 adapted to engage projections 76 provided in the intermediate section 57. Means is provided for yieldably retaining the latches 72 in engagement with the projections 76 and comprises a U-shaped spring 77 mounted within the end section 71 and engaging the latches 72. The latches 72 are provided with knurled portions 72a which extend outwardly which are adapted to be grasped by the fingers of the hand so that the latch portions 74 can be moved out of engagement with the projections 76 against the force of the spring 77.

The tunneling shaft assembly 46 also includes a tunneling member or tip 79 which is mounted on the distal extremity of the tunneling shaft or rod 47. As shown, the tip 79 is substantially olive-shaped and can also be called a second obturator. It is provided with a rounded hemispherical surface on its distal extremity which has a maximum diameter which is slightly less than the diameter of the bores 34 and 37 so that it can pass through the introducer sleeve 32. The proximal extremity of the tip 79 is of smaller diameter to provide an annular step 81 in the tip. The proximal extremity of the tip 79 is also hemispherical, as shown. The tunneling member or tip 79 can be formed of a suitable material such as plastic and can be secured to the distal extremity of the tunneling shaft or rod 47 by suitable means such as an adhesive. As hereinafter explained, the tunneling shaft or guide rod 47 is movable so that the tip 79 can be brought into engagement with the hemispherical end 53 of the introducer member 51 for a purpose hereinafter described.

The laparoscopic apparatus 31 also includes a balloon assembly 86 which is shown in FIGS. 2, 5 and 6. As shown in FIG. 5, when the balloon assembly 86 includes a balloon 87 which in plan, when deflated, has a pear-shaped configuration. The balloon is preferably formed of a non-elastomeric, medical-grade material of a suitable type such as PVC. Thus, the balloon 87 can be formed of two sheets 88 and 89 of such a material which have their outer margins bonded together by suitable means such as by a heat seal 91 extending around the perimeter of the flat balloon 87. The balloon 87 is provided with a neck 94 into which a flexible tubular member 96 extends, and is secured therein in a suitable airtight fashion such as by an adhesive. The tubular member 96 is provided with a lumen 97 which is in communication with the interior of the balloon and which can be used for inflating the balloon through a Luer-type fitting 98 mounted on the free end of the tubular member 96.

Means is provided for removably securing the balloon 87 to the tunneling rod or shaft 47, and a sleeve 101 formed of the same material as the balloon 87, and which can be formed integral or separate therefrom and adhered thereto by suitable means such as an adhesive. The sleeve 101 extends longitudinally of the balloon 87 and is disposed generally equidistant from the side margins of the same. The sleeve 101 is provided with a passage 102 extending therethrough which is sized to slidably accommodate the tunneling shaft or rod 47. Means is provided for permitting separation of the balloon 87 from the tunneling rod by movement sidewise from the axis of the passage 102 and takes the form of longitudinally spaced apart perforations 103 in the sleeve 101 extending longitudinally the length of the sleeve 101. The perforations 103 are spaced close enough together to form a weakened region so that the balloon can be readily separated from the tunneling rod by separating the plastic sleeve 101 by tearing the plastic between the perforations as hereinafter described.

As shown in FIG. 6, the sleeve 101 is disposed equidistant from the side margins of the balloon, permitting the balloon to be inflated as hereinafter described and as also shown by the dotted lines in FIG. 6, to be inflated around the rod 47. When deflated, the side margins of the balloon 87 can be rolled inwardly toward the rod 47 as shown by the broken lines in FIG. 6 to permit the same to be folded into a generally cylindrical configuration as shown in FIG. 2, and to be enclosed within a removable sleeve 106 carried by the tunneling shaft or rod 47. The removable sleeve 106 is formed of a relatively thin-walled tubular member 107 of a suitable material such as Teflon which has a weakened region 108 in its wall extending longitudinally the length thereof. This weakened region 108 can take the form of a slit as shown, or can be a series of perforations or slots formed in the wall, or a combination thereof. The proximal extremity of the tubular member 107 is provided with split-apart or separable end portions 107a and 107b to which are secured finger rings 109 of a suitable material such as plastic and secured thereto by fasteners 111.

Operation and use of the laparoscopic apparatus in performing the method for laparoscopic hernia repair through preperitoneal space may now be briefly described as follows. Let it be assumed that the laparoscopic apparatus 31 has been assembled as shown in FIG. 1. As shown in FIG. 7, let it be assumed that a human patient 121 is in a prone position and has a hernia 122 in the lower abdominal area which he wishes to have repaired. The patient is prepared in an appropriate manner by administering a suitable anesthesia, as for example a spinal anesthesia, and any other necessary preparation. The surgeon first makes an infraumbilical incision 126 in the skin below the navel or umbilicus 127 and separates the fat 129 and then incises the anterior rectus sheath or fascia 131 in the midline. Care should be taken not to penetrate the peritoneum overlying the abdominal cavity 133 (see FIG. 8).

After the incision 126 has been made in the manner hereinbefore described, the laparoscopic apparatus 31 is then taken by one hand of the surgeon, grasping the handle 56 and utilizing the other hand to facilitate the insertion of the rounded blunt tip 79 into the incision 126. The blunt tip 79 is caused to enter the slit in the fascia 131 and pass anterior to the peritoneum 132, in between the rectus muscles (laterally), and enters the potential preperitoneal space 136 to be provided for the laparoscopic procedure. The blunt tip 79 is then utilized as a tunneling device by the surgeon using one hand 56 to advance the blunt end 79 toward the pubic region of the patient while the surgeon places his other hand on the abdomen to feel the apparatus or device 31 as it is being advanced. The advance of the device 31 is continued until the blunt tip 79 is below the symphysis pubis 137 as shown in FIG. 8, and preferably is disposed between the symphysis pubis 137 and the bladder 138.

After the apparatus or device 31 has been properly positioned as shown in FIG. 8, the removable sleeve or sheath 106 is removed by the surgeon using one hand to engage the finger rings 109 which are exterior of the body of the patient and outside of the incision 126. At the same time, the other hand of the surgeon is utilized to stabilize the portion of the device 31 which is within the preperitoneal space. The sheath 106 can be readily withdrawn since it is formed of Teflon and is split or weakened along its length, by pulling it proximally and away from the longitudinal axis of the tubular member 33. As the sheath 106 opens and slips off, it exposes the balloon 87 of the balloon assembly 86. When the sheath 106 is completely removed, a sterile saline solution serving as a balloon inflation medium is introduced into the balloon 87 through the tubular member 96 by connecting a conventional syringe 141 to the Luer fitting 98. The balloon 87 typically can be inflated to a suitable size by introducing 500 cc or less of normal saline solution into the balloon by pressing on the plunger 142. As the balloon 87 is inflated, the balloon progressively unwraps with its side margins rolling outwardly from the center while expanding into a plane to cause progressive separation or dissection of tissue (i.e. 131, 132) along its weakest points by application of forces generally perpendicular to the plane of the balloon as indicated by the arrows 143 in FIGS. 6 and 9, to create the preperitoneal or anatomic space. The balloon 87 expands around the tunneling shaft 47 in the manner shown in broken lines in FIG. 6 to achieve the progressive separation until complete inflation is achieved. The surgeon can sense the filling of the balloon by feeling the abdomen of the patient as the balloon is inflated. The balloon 87 serves to open up the preperitoneal space 136 to provide a bloodless space for the procedures hereinafter to be performed. Since the balloon is formed of a non-elastomeric material, it is a volume-limited balloon to prevent overexpansion. Different sizes of balloons can be utilized for different patient sizes. With a smaller balloon it is possible to deflate the balloon and then shift the balloon and again reinflate it to obtain the desired bloodless preperitoneal space.

After the desired bloodless anatomic space or pocket 136 is formed, the balloon 87 is deflated by withdrawing the normal saline solution by withdrawal of the plunger 142 of the syringe 141 or via a hospital vacuum aspirator. After the balloon 87 has been deflated, the balloon assembly 86 can be removed by grasping the handle 56 of the laparoscopic apparatus or device 31 with one hand and using the other hand to grasp the tubular member 96 and the proximal extremity of the balloon 87 and to remove the same through the incision 126, as shown in FIG. 10. As the balloon 87 is being removed, it is progressively separated from the tunneling rod or shaft 47 by causing the sleeve 101 to split apart along the longitudinal perforations 103 provided in the sleeve 101. This makes it possible to separate the balloon 87 from the tunneling rod 47 without the necessity of removing the tunneling rod 47 or the introducer device 32.

After the balloon assembly 86 has been removed, the introducer device 32 can be advanced distally over the tunneling shaft or rod 47 so it extends well into the preperitoneal space 36 as shown in FIG. 11. The end section 71 of the handle 56 is then removed by depressing the latches 72 by having the fingers engage the portions 72a to disengage the latch portions 74 from the intermediate section 57 of the handle 56. The end section 71 is then drawn proximally as shown in FIG. 11 to bring the olive-shaped tip 79 into engagement with the obturator 53 disposed in the distal extremity of the tubular member 33 to cause both the tip 79 and the obturator 53 to be withdrawn or retracted. As the introducer member 51 is being withdrawn, its chamfer 54 will strike the cam surfaces 67 of the latches 61 to cause them to disengage from the end piece 36 to carry it along with the introducer member 51 and shown in FIG. 2. Thus, it can be seen that the tunneling shaft assembly 46 can be readily removed merely by one motion of the surgeon's hand. Thereafter, a conventional laparoscope 144 (see FIG. 16) can be introduced through the introducer sleeve 32 to permit the surgeon to view the preperitoneal space 136.

The dissected preperitoneal space 136 is then insufflated with carbon dioxide through the stopcock 41 to a pressure ranging from 6 to 8 mm of mercury. Thereafter, two additional trocars 146 and 147 are introduced through the abdominal wall into the dissected preperitoneal space 136 in appropriate locations. Thus, as shown in FIG. 7, trocar 146 is introduced into the left side of the abdomen of the patient below the introducer sleeve 32 and the trocar 147 is introduced into the dissected preperitoneal space immediately above the symphysis pubis and directly below the introducer sleeve 32. As can be appreciated, the locations of the trocars 146 and 147 is generally dictated by the location of the hernia 122 to be repaired.

Figure 12:
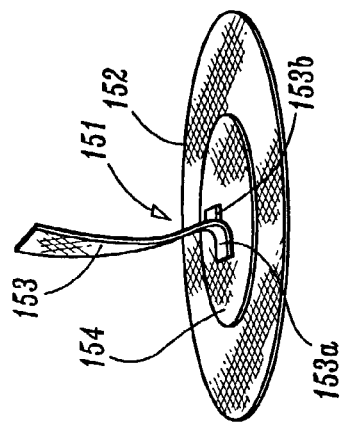
FIG. 12 is an isometric view of a patch incorporating the present invention.
Figure 13:
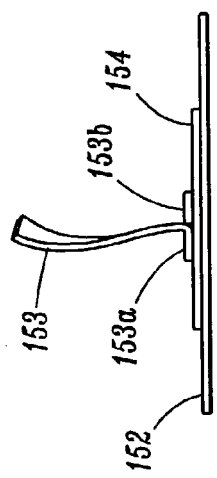
FIG. 13 is a side elevational view of the patch shown in FIG. 12.
Figure 14:
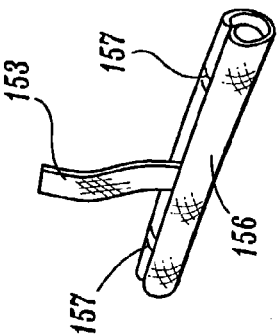
FIG. 14 is an isometric view showing the patch in FIGS. 12 and 13 in a rolled-up, generally cylindrical configuration.

A patch 151 of the present invention to be utilized in the hernia repair procedure is shown in detail in FIGS. 12, 13 and 14. The patch 151 can be characterized as a hernia patch or graft and is made of a suitable plastic mesh such as a Prolene mesh manufactured by Ethicon, Inc. The patch 151 can be of any desired configuration. For example it can be generally circular as shown, and a disk 152 of a suitable diameter, as for example 2 inches. A tail 153 is secured to the disk substantially in the center thereof, in a suitable manner. For example, as shown, the tail 153 can be provided with split portions 153a and 153b which are split apart and offset with respect to each other, which are secured to a smaller reinforcing disk 154 formed of the same material as disk 152 and secured to the disk 152 by suitable means such as surgical thread (not shown). The tail 153 is formed of the same material as the disk 152 and 154, or it can be formed of a different material, such as Goretex. It can have a size such that it has a width of approximately ½ inch and a length of approximately 1½ inches. As shown particularly in FIG. 14, the side margins of the disk 152 can be rolled inwardly towards the center adjacent the tail 153 to form a cylindrical roll 156 such as shown in FIG. 14 with the tail 153 extending outwardly therefrom. The roll 156 can be maintained in its rolled-up condition by means of sutures 157 disposed adjacent opposite ends of the roll and on opposite sides of the tail 153.

Figure 16:
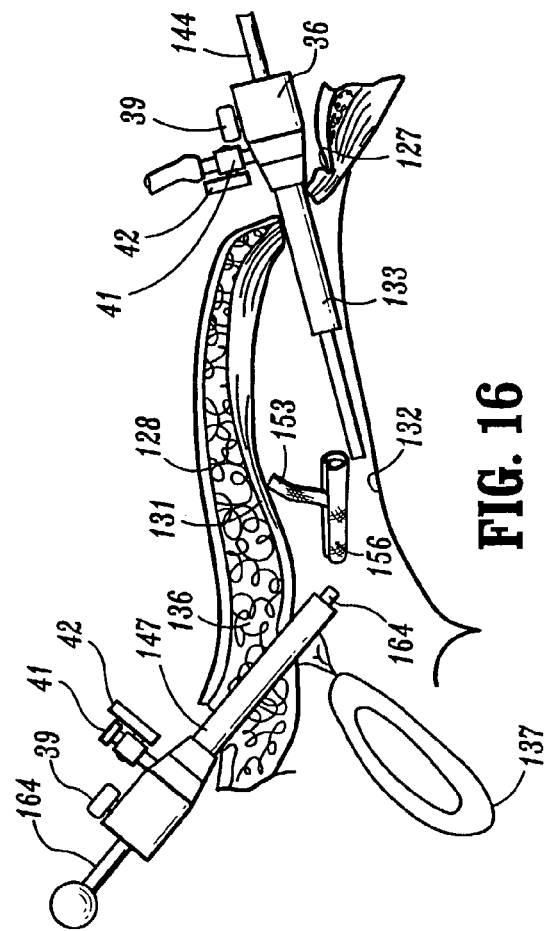
FIG. 16 is a sagittal view showing the introducer through which the rolled-up patch in FIG. 17 has been introduced into the preperitoneal space by an introducer rod.

Conventional laparoscopic instruments are utilized which are introduced through the trocars 146 and 147 while visualizing the same through the laparoscope 144 introduced through the introducer device 32 to dissect the hernia 161 to permit visualization of its neck 162 as it is entering the internal inguinal ring 163. The hernia sac 161 is dissected from the surrounding tissue (spermatic duct and vessels) (see FIG. 15). The process is facilitated by $CO_2$ pressure impinging on the neck of the hernia sac. As soon as this dissection is completed, the roll 156 is pushed into the trocar 147 and advanced through the same by suitable means such as a deployment rod 164 (see FIG. 16) to enter the dissected preperitoneal space 13 as shown in FIG. 16. Alternatively, the roll 156 can be placed in a tubular member (not shown) which can be used to position the roll 156 within the trocar 157. Thereafter, by the deployment rod 164, the roll 156 can be pushed out of the tubular member into the dissected preperitoneal space 136.

Figure 17:
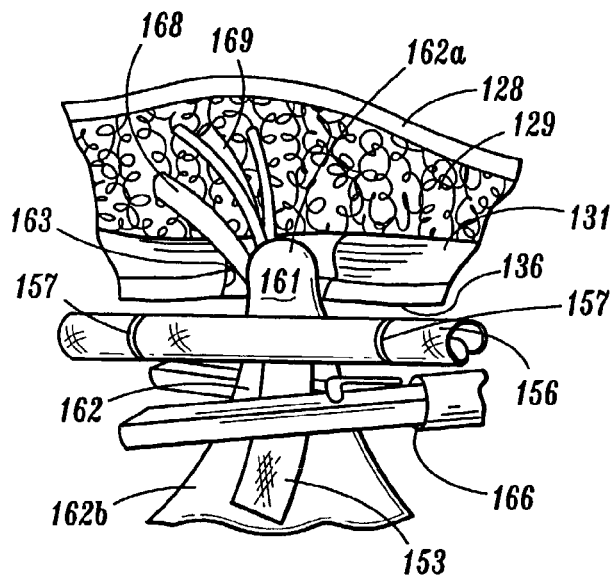
FIG. 17 is a sagittal view similar to FIG. 16 showing the attachment of the patch to the hernia sac.
Figure 18:
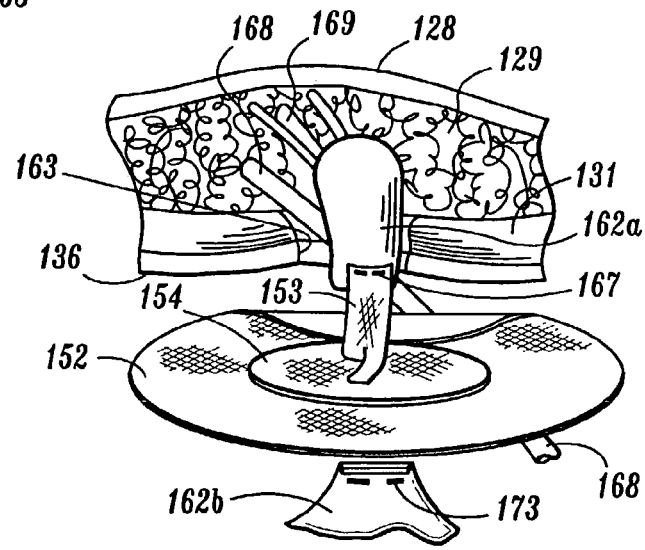
FIG. 18 is a sagittal view similar to FIG. 17 showing the dissection of the hernia sac and the unrolling of the patch.
Figure 19:
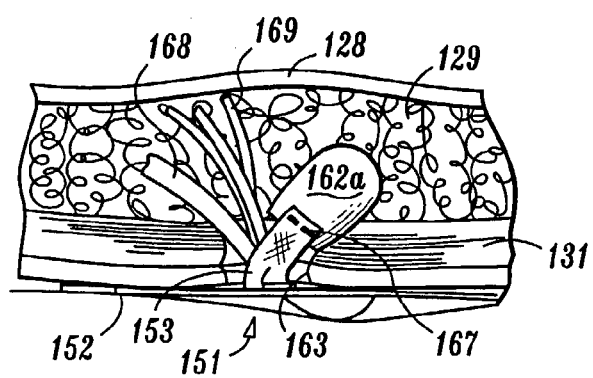
FIG. 19 is a sagittal view showing the patch in place to provide the hernia repair.

The roll 156 after it is in the preperitoneal space is then manipulated so that its tail 153 is disposed alongside the neck 162 of the hernia sac 161 as shown in FIG. 17. A conventional stapling device 166 is then introduced through the trocar 146 to staple the tail 153 to the neck 162 by placing staples 167 therein. These staples 167 serve to divide the neck of the sac into distal and proximal portions 162a and 162b. As soon as this stapling operation is completed, the two portions 162a and 162b are separated from each other because of the pressure of the insufflation gas to cause the tail 153 of the patch 151 to be pulled upwardly into the inguinal ring to pull with it the disk 152. The sutures 157 are cut apart to permit the disk 152 to unroll and to be placed across the inguinal ring 163 which created the main weakness in the abdominal wall permitting the hernia which is being repaired to occur. The proximal portion 162b of the neck 162 is stapled together by staples 173 as shown in FIG. 18. The proximal portion 162 is then permitted to fold back into the desired anatomical location within the abdomen.

Thereafter, while observing the procedure under the laparoscope, the dissected preperitoneal space 136 can be deflated by permitting the carbon dioxide gas to escape to the atmosphere through the stopcock 41 in the introducer device 32 by operation of the stopcock lever arm 42. As deflation is taking place, the movement of the patch 151 is observed through the laparoscope 144 so that it does not become displaced. When the deflation has been completed, the patch 151 is in a position over the inguinal ring 163 and serves to provide enforcement to prevent the occurrence of another hernia in that area. The tail 153 is disposed with the inguinal ring 163 and retains the mesh disk 152 so that it surrounds the inguinal ring 163.

After deflation has been accomplished, the trocars 146 and 147 as well as the introducer device 32 can be removed. Small sutures can then be utilized to close the various small openings which have been provided in the abdominal wall so that upon healing there will be minimal noticeable scars from the procedure. The scar in the navel or umbilicus typically is almost nearly invisible.

It has been found that the use of the laparoscopic apparatus 31 in accomplishing the method as hereinbefore set forth provides a procedure in which the pain after the operation is markedly reduced. This is particularly true since the operation does not involve suturing of any ligaments which typically produces the pain. In addition, the recovery time for the patient is greatly accelerated. In the procedure of the present invention, a patient can return to work within a matter of 3 to 5 days rather than in a number of weeks as in a conventional hernia repair procedure. The procedure also has other advantages. For example, there is a lack of necessity for a general anesthesia. Another principal advantage of the procedure is there is no contact of mesh patch 151 with the intestines of the patient or other intra-abdominal structures, thus greatly reducing the possibility of adhesion formation. In addition, the graft which is formed by the patch 151 is more secure and is positioned in an anatomically correct position. This is because the hernia sac is in exact alignment with the hernia and pulls with it the tail 153 of the graft to ensure that the graft formed by the patch 151 is drawn into the correct position and is maintained in that position to prevent migration. In addition, the graft, by having an additional central disk 154, ensures that additional reinforcement is provided in the proper location in the center where the weakest region in the abdominal wall has occurred. In addition, by such proper centering, the mesh construction of the patch 151 serves to uniformly reinforce the area surrounding the hernia.

Figure 20:
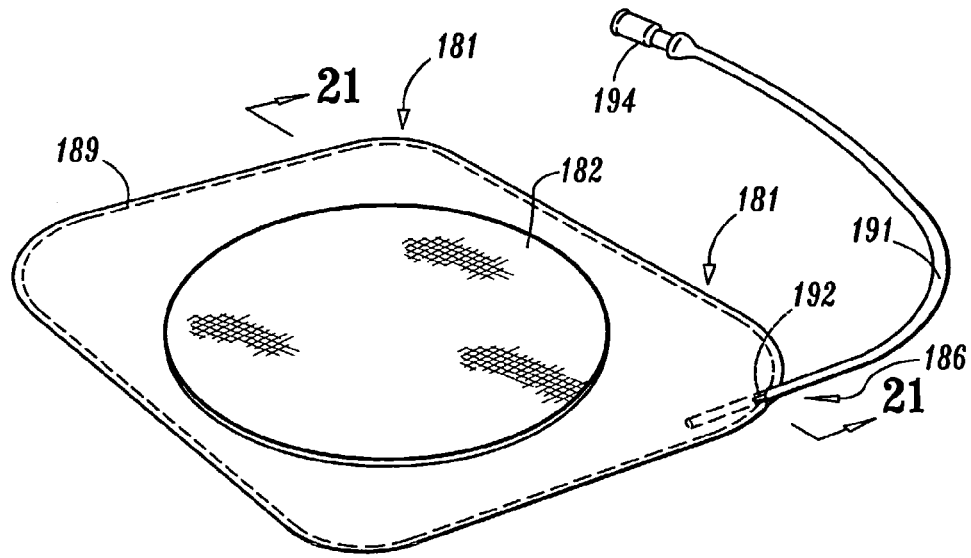
FIG. 20 is an isometric view of another embodiment of a balloon with a patch disposed thereon for use with the apparatus of the present invention.
Figure 21:
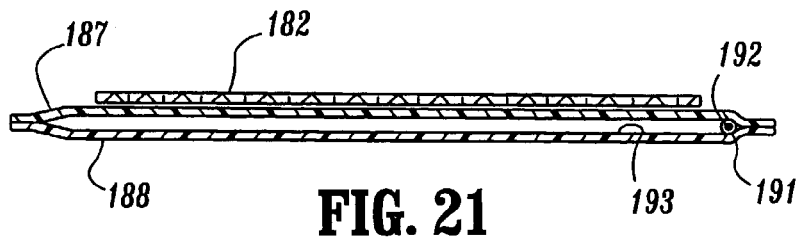
FIG. 21 is a cross-sectional view taken along the line 21-21 of FIG. 20.
Figure 22:
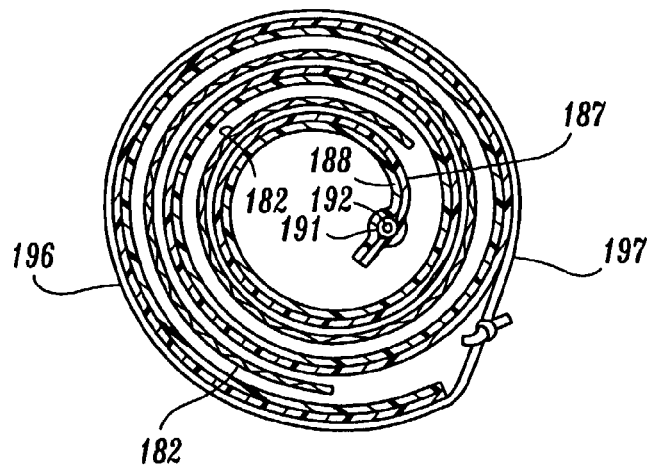
FIG. 22 is an enlarged cross-sectional view taken along the line 22-22 of FIG. 23.

Another embodiment of the present invention is shown in FIGS. 20, 21 and 22 with respect to another embodiment of a balloon assembly 181 and another embodiment of a patch or graft 182. The balloon assembly 181 includes a balloon 186 formed of two sheets 187 and 188 which are rectangular in shape, as for example square as shown in FIG. 20, which are heat-sealed together at their outer margins as indicated by the broken line 189. A tubular member 191 is provided which has one end sealed into one corner of the balloon 186 as shown in FIG. 20. The tubular member 191 is provided with a lumen 192 which opens up into the interior space 193 of the balloon.

The sheets 187, 188 are formed of a non-elastomeric material of the type hereinbefore described. A Luer fitting 194 is connected into the free end of the tubular member 191 and is utilized for introducing a saline solution into the balloon 186 for inflating the same.

The graft or patch 182 can have a desired configuration, as for example circular as shown in FIG. 20. It is formed of a non-absorbable synthetic surgical mesh, as for example from polypropylene manufactured by Ethicon Inc. As shown, the mesh patch 182 overlies the sheet 187.

Figure 23:
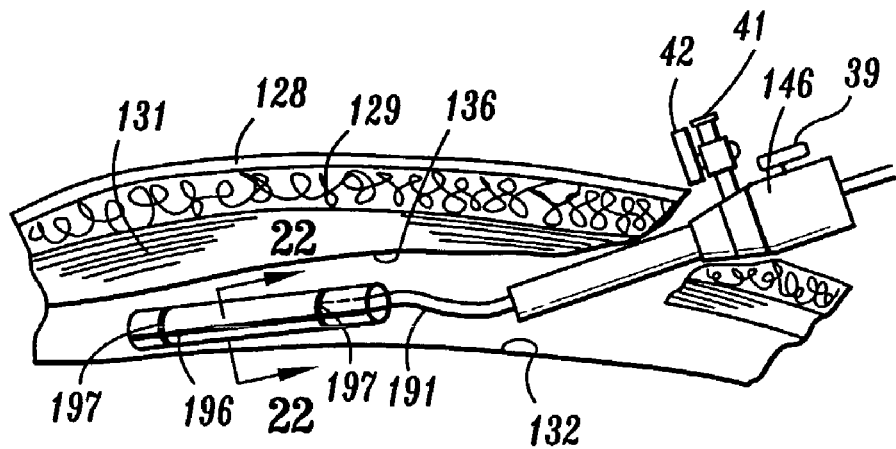
FIG. 23 is a sagittal view showing the manner in which the balloon and patch shown in FIG. 20 are disposed in the preperitoneal space.
Figure 24:
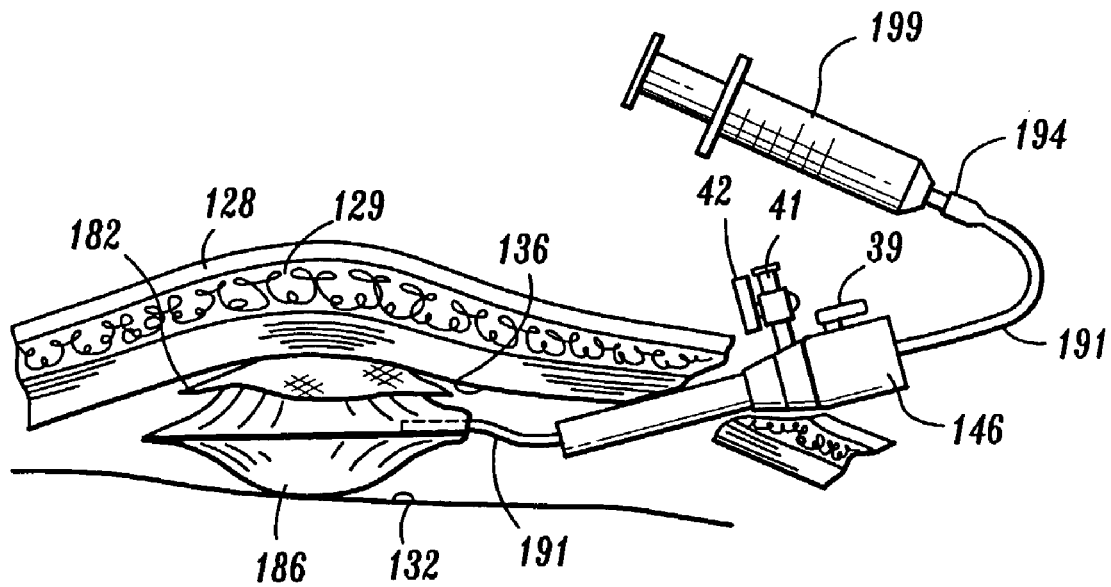
FIG. 24 is a sagittal view showing the placement of the balloon and the patch of FIG. 20, and the inflation of the balloon in the preperitoneal space.

The balloon assembly 182 with the patch 182 thereon can be rolled up into a roll 196 as shown in FIG. 22 in which the patch or graft 182 is disposed within the roll. The roll can be maintained in the roll configuration by sutures 197 wrapped about the same. The roll 196 can then be introduced through a side trocar 146 and introduced into the dissected preperitoneal space 136 with the tubular member 191 extending through the trocar 146 and having its Luer fitting 194 disposed outside of the trocar. After the roll 196 has been introduced, the sutures 197 can be removed and the balloon can be inflated by introducing a saline solution through the fitting 194 by use of a syringe 199. Before the saline solution is introduced to inflate the balloon, the roll 196 is properly positioned so that when it is inflated and begins to unroll it will unroll in the proper direction so that the graft or patch 182 carried thereby is properly positioned as shown in FIG. 23. After the roll 196 has been completely unrolled, continued inflation of the balloon 186 moves the patch 182 so that it is pressed against the portion of the fascia through which the hernia has occurred as shown in FIG. 24. As soon as the graft 182 has been properly positioned, the balloon 186 is deflated. The trocar 146 is then removed, and thereafter the balloon can be withdrawn through the opening in which the trocar was present. Thereafter, the gas utilized for insufflation can be permitted to discharge through another trocar so that the fascia 131 comes into engagement with the peritoneum 132 with the large-area patch 182 held in place therebetween. Thereafter, the trocars can be removed in the manner hereinbefore described to complete the procedure.

Another embodiment of a balloon assembly for deploying a large-area patch or graft through a trocar is shown in FIG. 25. The large-area graft 201 shown in FIG. 25 is formed of a mesh material of the type hereinbefore described and has a generally oval-shaped configuration conforming to the general shape of the balloon 202 of the balloon assembly 203. The balloon 202 is constructed of a non-elastomeric material in the manner hereinbefore described. A tubular member 206 is provided for inflating the balloon and has a Luer fitting 207 on the free end thereof. Means is provided for retaining the mesh graft 201 on one side of the balloon and plastic flaps 208 provided on opposite sides of the balloon 202, and secured thereto by a suitable means such as a heat seal along the broken line 209. The inner margins of the flaps 208 are free and are adapted to receive the outer margins of the graft 201 as shown particularly in FIG. 25.

The balloon 202 with the mesh graft 201 thereon can be rolled up into a substantially cylindrical roll 211 by rolling the outer margins of the balloon inwardly on top of the mesh material to provide two rolls 211 and 212 which are brought in adjacent to each other as shown in FIG. 26 with the mesh graft 201 being wrapped up therewith. The two rolls 211 and 212 can then be inserted into a tubular sheath 214. The sheath 214 can then be introduced through a trocar in a manner hereinbefore described and then pushed out of the sheath into the abdominal cavity. The balloon can then be inflated with a saline solution to cause the two rolls 211 and 212 to unroll in opposite directions and then for the balloon to inflate to move the patch 201 carried thereby into engagement with the portion of the fascia having the hernia therein. Thereafter, the balloon can be deflated, the trocar removed, the balloon removed, and the dissected preperitoneal space deflated so that the large mesh graft 201 is disposed between the fascia and the peritoneum and is retained in position therebetween.

Another embodiment of a graft which can be utilized in connection with the present invention is shown in FIG. 27. The patch or graft 216 is constructed in a manner similar to the graft or patch 151 shown in FIGS. 12 and 13, with the exception that it is constructed in a manner so that it can be utilized with a direct hernia rather than an indirect inguinal hernia hereinbefore described. The graft 216 is formed of a sheet of circular mesh in the form of a disk 217 with a reinforcing central disk 218 which has a barbed head 219 secured thereto. The barbed head 219 is formed of a biodegradable material such as polyglycolic acid. The mesh graft 216 can be folded over a deployment rod 221 and introduced into a cylindrical sheath 222 (see FIG. 28) which is sized so that it can be introduced through a conventional trocar, then deployed from the sheath 22 by pushing on the deployment rod 221. After the graft 216 has been deployed into the dissected preperitoneal space 136, it can be positioned in an appropriate manner so that the barb 219 is positioned so that it is in alignment with the inguinal ring whereby upon deflation of the preperitoneal space 136, the barb 219 will extend through the inguinal ring to serve to retain the graft 201 firmly in place.

Another embodiment of a laparoscopic apparatus incorporating the present invention is laparoscopic apparatus 231 as shown in FIGS. 29 through 32. The laparoscopic apparatus 231 includes introducer sleeve or device 32 identical to that hereinbefore described. It also includes a tunneling shaft assembly 46 which is provided with a tunneling shaft or rod 47 and a proximal extremity 49 (see FIG. 32). In the previous embodiment of the laparoscopic apparatus, the tunneling shaft assembly is provided with an olive-shaped or bullet-shaped tip 79 which was secured to the distal extremity 49 of the tunneling shaft 47. In the present embodiment of the apparatus shown in FIGS. 29 through 32, the obturator tip 79a is detachably mounted on the distal extremity 49 of the tunneling rod 47. The proximal extremity of the tip 79a is provided with a slot 236 which extends through one side of the proximal extremity into the central portion of the proximal extremity of the tip 79a. The slot 236 is adapted to receive the rounded extremity 237 provided on the distal extremity 49 of the tunneling rod 47 (see FIG. 32). A removable sleeve 241 is provided as a part of a laparoscopic apparatus 231, and is similar in many respects to the removable sleeve or sheath 106 hereinbefore described. The removable sleeve 241 is formed of a suitable material such as Teflon as hereinbefore described and is provided with a tubular member 242 which is provided with a relatively thin wall 243 that has a weakened portion extending longitudinally thereof in the form of a slit 244 (see FIG. 31). The tubular member 242 is provided with a proximal extremity 246 and a distal extremity 247. The proximal extremity 246 has a thicker cross-section than the distal extremity 247, as shown in FIGS. 31 and 32. The proximal extremity 246 is provided with a recess 248 formed in the wall which is diametrically opposite the slit 244 that serves as a relief region to permit the movable sleeve 241 to be split apart when it is removed from the balloon.

The proximal extremity 246 is provided with wing-like members 251 and 252 which extend diametrically therefrom, spaced 90° apart from the slit 244. These outstretched wings 251 and 252 serve to help the physician orient the laparoscopic apparatus 231 as it is being utilized. The proximal extremity 246 is also provided with a handle 256 which is formed integral therewith and which extends radially from the tubular member 242. The handle 256 is provided with a finger hole 257 extending therethrough through which a finger can be inserted to facilitate pulling the removable sleeve 241 off of the balloon as described in connection with the previous embodiment.

Figure 33:
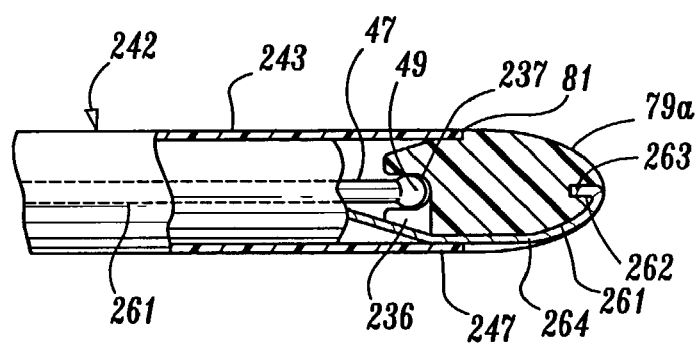
FIG. 33 is an enlarged cross-sectional view of the distal extremity of the laparoscopic apparatus shown in FIG. 29.
Figure 34:
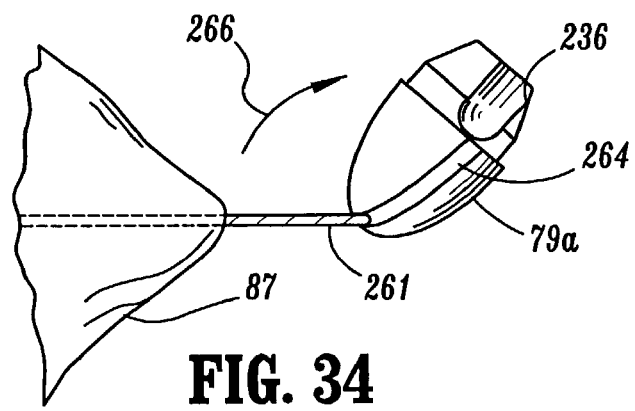
FIG. 34 is a partial plan view showing the balloon after it has been removed from the laparoscopic apparatus with the obturator tip shifting its position.
Figure 35:
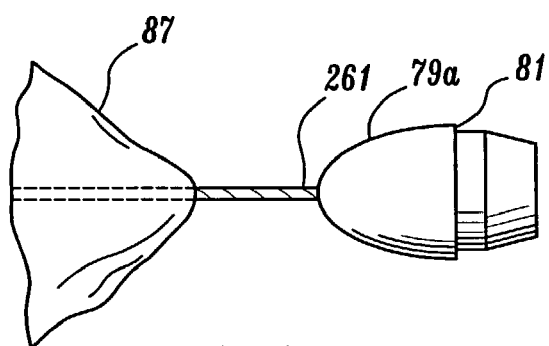
FIG. 35 is a plan view of the balloon shown in FIG. 34 as it is being removed from the body of the patient and bringing along with it the obturator tip.
Figure 39:
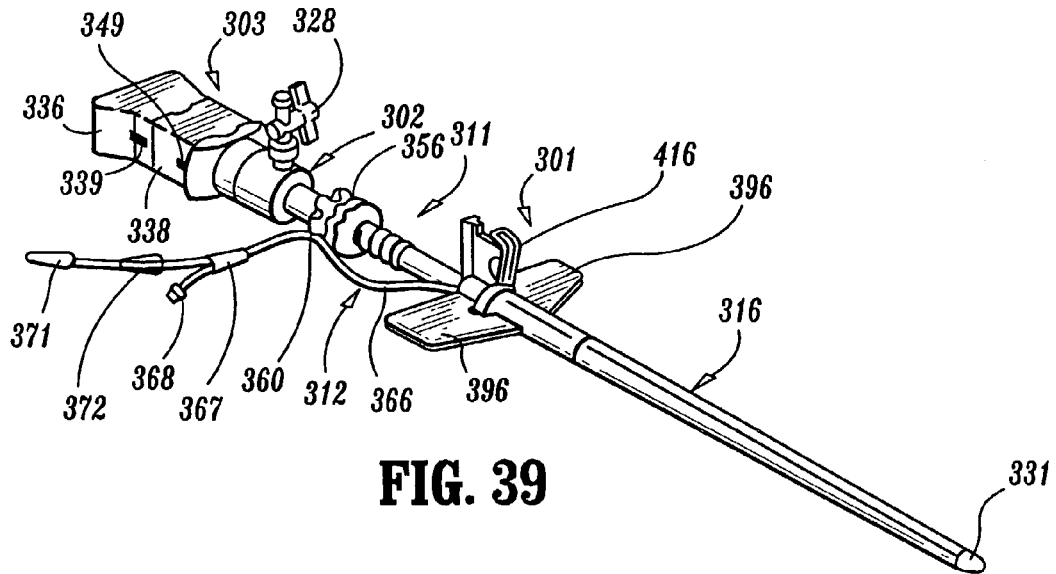
FIG. 39 is an isometric view of a surgical dissector with a cannula incorporating the present invention in an assembled condition.

As shown in FIG. 33, the tip 79a is detachably mounted in the proximal extremity of the removable sleeve 241 so that the tip 79 can serve as a second obturator during introduction of the laparoscopic apparatus 231 as hereinbefore described. Means is provided for securing the detachable tip 79a to prevent it from becoming separated from the laparoscopic apparatus 231 and for permitting its withdrawal after the laparoscopic procedure is being completed. As shown in FIGS. 33 and 34, such means include a flexible elongate element 261 in the form of a braided string formed of a suitable fabric such as Nylon, which has one end 262 secured in a slot 263 provided on the distal extremity of the tip 79a by suitable means such as an adhesive (not shown). The flexible elongate element 261 extends from the distal extremity of the tip 79a in a recess 264 opening through the external surfaces of the tip 79a. The proximal extremity of the flexible elongate element 261 can be secured directly to the balloon 87 or, alternatively, it can extend through the perforated sleeve 101 provided in the balloon along the tunneling shaft so that it extends beyond the proximal extremity of the tunneling shaft.

The use of the laparoscopic apparatus 231 in performing a laparoscopic procedure is substantially identical to that hereinbefore described with the exception that when the removable sleeve 241 is removed from the balloon 87, the removable sleeve can be pushed forwardly to detach the tip 79a from the tunneling shaft 47. The removable sleeve 241 then can be pulled rearwardly to separate it from the balloon along the slit 244. As soon as this occurs, the tip 79 becomes free of the sleeve and begins to rotate in the direction of the arrow 266 shown in FIG. 34. When the balloon has been inflated and has performed its functions as hereinbefore described and it is now desired to remove the balloon 87, the balloon 87 can be withdrawn in the manner hereinbefore described, and since the tip 79a is tethered to the balloon 87 itself or flexible elongate element 261 attached thereto extends out proximally of the balloon 87, the tip 79a is withdrawn or can be withdrawn with the balloon 87.

This laparoscopic apparatus 231 with its detachable obturator tip 79a will be useful in certain applications of the present invention. With the previous laparoscopic apparatus hereinbefore described, there is a possibility that when the obturator tip 79 is withdrawn, critical structures, as for example small arteries, may be inadvertently incised between the tip 79 and the distal extremity of the tubular member 33 of the introducer device 32. This possibility is eliminated by having the detachable tip 79a, which is withdrawn when the balloon is withdrawn.

Still another embodiment of the laparoscopic apparatus incorporating the present invention is shown in FIGS. 36, 37 and 38, in which the laparoscopic apparatus 271 comprises a balloon 272 of the type hereinbefore described, which is provided with a perforated sleeve 273 through which the tunneling rod 47 extends. The distal extremity 274 of the sleeve is closed by an end piece 276. The balloon 272 is wrapped in the manner hereinbefore described around the tunneling shaft 247. The tunneling shaft or rod 47 is not provided with a tunneling member or second obturator of the type hereinbefore described but its end is rounded as shown by providing a rounded tip 47a.

The wrapped balloon 272 is enclosed within a removable sleeve 281 which is similar to those hereinbefore described. It is provided with a tubular member 282 that has a weakened region in the form of a slit 283 extending longitudinally the length thereof. The removable sleeve 281 differs from those hereinbefore described in that rather than being open at the end as in previous embodiments, it is provided with a closed-end, bullet-shaped or olive-shaped tip 286. The slit 283 is provided with a curved portion 283a which extends through the bullet-shaped tip 286 so that the sleeve can be peeled off of the balloon 272 in the manner hereinbefore described by pulling on the handle 288 having a finger hole 289 therein. During the time that the removable sleeve 281 is being peeled off or separated from the balloon 272, the balloon is held in place by the tunneling rod 47 which engages the end 276 of the perforated sleeve 273. The balloon 272 after it is inflated can be separated from the tunneling rod 47 by pulling on the balloon and causing its distal extremity to lift up and to break apart at the perforations and peel away from the rounded extremities 47a of the tunneling shaft 47 as shown in FIG. 38. Continued pulling on the balloon 272 will cause it to separate from the tunneling rod 47 so that the balloon 272 can be removed as hereinbefore described. Thus, it can be seen that there has been provided an embodiment of the laparoscopic apparatus of the present invention in which the need for an obturator carried by the distal extremity of the tunneling rod 47 has been eliminated by providing the second obturator as a part of the removable sleeve 281. In all other respects, the operation and use of the laparoscopic apparatus 271 is similar to that hereinbefore described.

From the foregoing it can be seen that there has been provided an apparatus and method for developing an anatomic space by the use of a wrapped balloon which, as it is inflated, gradually unwraps to tend to form a plane to cause forces to be created perpendicular to the plane for pulling apart tissue along a natural plane to provide an anatomic space, thereby providing a dissection in the weakest plane creating a more natural, less traumatic and bloodless region in which to perform various medical procedures. Such anatomic spaces can be created in various parts of the human body, for example in the preperitoneal area to provide a space anterior to the peritoneum for hernia repair and for varicocele dissection. Spaces can also be developed lateral to the peritoneum and spaces posterior to the peritoneum for performing medical procedures such as a sympathectomy and a lymph node dissection.

As hereinbefore explained, the apparatus and method is particularly appropriate for performing laparoscopic hernia repair, permitting the use of grafts and patches which can be used for direct and indirect hernias with minimal pain to the patient and with the patient being able to return to work within a few days.

Another embodiment of a laparoscopic apparatus 301 incorporating the present invention is shown in FIGS. 39-48. The laparoscopic apparatus 301 can also be described as an assembly in the form of a surgical dissector with a cannula which serves as a hand manipulated surgical instrument that can be used during general surgical laparoscopic procedures to dissect the layers of fascia between the skin and the peritoneum as described in conjunction with the previously disclosed embodiments of the invention. The laparoscopic apparatus 301 comprises a cannula 302 with a tunneling device 303 mounted therein. The tunneling device 303 or guide rod 306 comprises a blunt obturator and an introducer member 307. The laparoscopic apparatus also includes a skin seal assembly 311, a balloon assembly 312 and a balloon cover assembly 316 as shown particularly in FIGS. 39 and 40.

The cannula 302 comprises a cannula tube 321 formed of a rigid plastic having proximal and distal extremities 322 and 323. A flow passage 324 extends from the proximal extremity 322 to the distal extremity 323. A cannula housing or handle 326 is mounted on the proximal extremity by suitable means such by molding it directly thereon. As disclosed in application Ser. No. 07/968,201, now U.S. Pat. No. 5,324,270, filed on Oct. 29, 1992, the handle 326 includes first and second valve members (not shown) in which one valve member serves as a duck-bill valve and the other valve member serves as a circular instrument or tool seal. The housing is provided with a Luer-type fitting 327 which is in communication with the interior of the housing outside of the duck-bill valve and is in communication with the passage 324 in the cannula tube 321.

As described in said application Ser. No. 07/968,201, filed on Oct. 29, 1992, now U.S. Pat. No. 5,324,270, the cannula 302 is adapted to receive the tunneling device or blunt obturator device 303 which is generally of the type described hereinbefore in the present application. This device 303 comprises the blunt obturator 306 having a blunt tip 331 which is generally olive-shaped as shown (see FIG. 41) and is formed of a suitable material such as plastic. The olive-shaped tip 331 is molded on the distal extremity 332 of a rod or a shaft 333 formed of a suitable material such as stainless steel. The blunt tip 331 is sized so that its outside diameter is slightly less than the inside diameter of the cannula tube 321. The proximal extremity 334 of the rod or shaft 333 has mounted thereon a handle part 336 of a handle assembly 337 which includes a second handle part 338. The handle parts 336 and 338 are adapted to mate with each other and are detachably connected in a manner described in copending application Ser. No. 07/968,201, filed on Oct. 21, 1992 by the use of latch means (not shown) adapted to be actuated by spring-operated latch members 339 disposed on opposite sides of the handle part 336 and adapted to be engaged by the fingers of the hand holding the handle assembly 337. The second handle part 338 forms a part of the introducer device 307 and is mounted on the proximal extremity 341 of an introducer member 342 formed of a suitable material such as plastic. The introducer member 342 is provided with a distal extremity 343 and has a bore 344 extending from the proximal extremity to the distal extremity through an end surface 346 (see FIG. 41) which is inclined at a suitable angle, as for example approximately 45° proximally from the horizontal axis for the bore 344. The bore 344 is sized so it can slidably receive the shaft 333.

The handle part 338 is provided with latch means (not shown) which is adapted to releasably connect the handle part 338 to the cannula housing 326 and includes latch members 349 disposed on opposite sides of the handle part 338 adapted to be engaged by the fingers of the hand holding the handle assembly 337 to permit the handle part 338 to be separated from the cannula housing 326.

The skin seal assembly 311 generally can be of the type described in application Ser. No. 08/124,333, filed on Sep. 20, 1993, now abandoned, and as described therein includes a screw body 350 formed of a suitable material such as plastic having a helical thread 351 and a scalloped flange 352. A resilient insert 353 is disposed in the screw body 351 and is formed of a suitable resilient material such as silicone. The insert 353 is provided with a bore 354 extending therethrough. A collet 357 having slots 358 therein surrounds the insert 353 and is engaged by a collar 356 movable axially of the screw body 351 and is adapted to move the collet to compress the insert 353 to move the insert between a retaining position for the cannula tube 321 extending through the bore 354 to retain the cannula 302 in a desired longitudinal position with respect to the skin seal assembly 311 and a releasing position in which the cannula 302 can be slidably moved longitudinally inwardly or outwardly with respect to the skin seal 311. The collar 356 is provided with an annular shoulder 359 having circumferentially spaced-apart slots 360 therein which are used for a purpose hereinafter described. As explained in copending application Ser. No. 08/124,333, filed Sep. 20, 1993, means is provided to restrain rotation of the collar 356 with respect to the collet 357 and includes longitudinally extending keys 355 spaced 180° apart.

Figure 40:
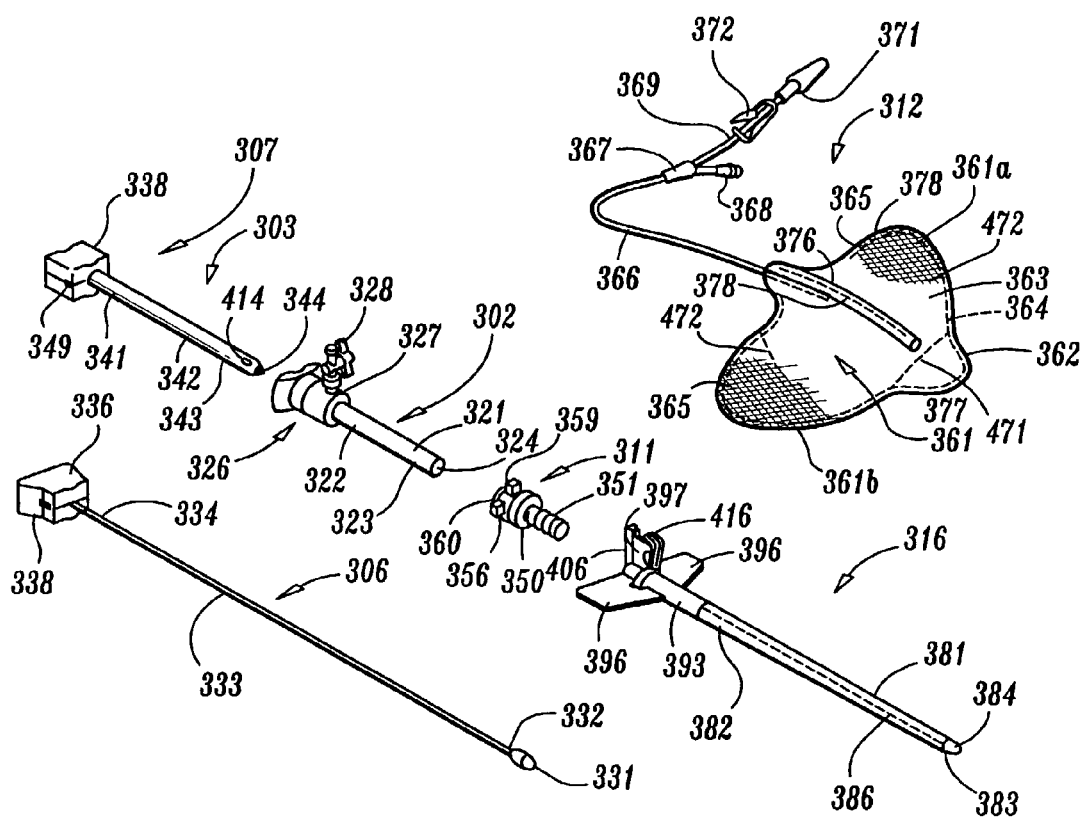
FIG. 40 is an isometric exploded view of the components of the surgical dissector with cannula shown in FIG. 39.
Figure 41:
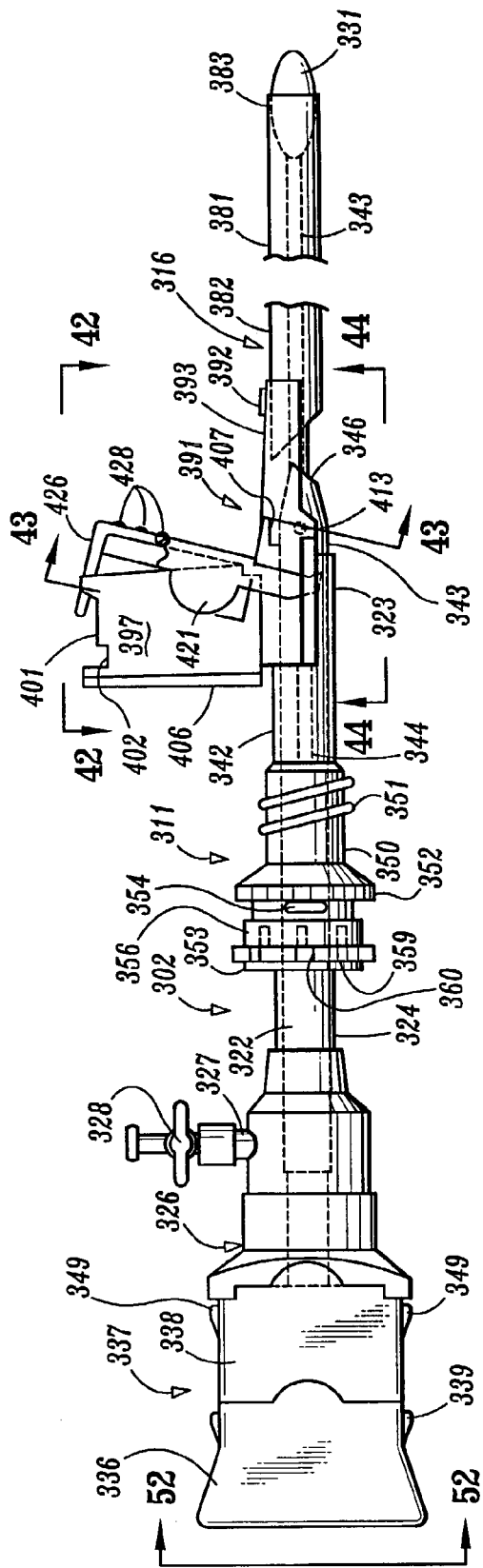
FIG. 41 is a side elevational view of the assembly shown in FIG. 39.

The balloon assembly 312 comprises a balloon 361 formed of a non-elastomeric, medical grade plastic material of a suitable type such as polyurethane. The balloon 361 can be characterized as having an symmetric manta ray configuration when viewed in plan and is provided with a forwardly extending rounded protuberance 362 which has a width substantially less than that of the balloon 361. The balloon 361 comprises at least one sheet of material which can be identified as a first or upper sheet 363 and a second or lower sheet 364 which have been die cut to the desired configuration with their edges bonded together in a suitable manner such as by means of a heat seal to form a balloon which has a generally flat configuration when deflated as shown in FIG. 40. The upper or outer surface of the first or upper sheet 363 has been roughened in areas 365 as shown in FIG. 40 on the outwardly extending lobe portions 361*a* and 361*b* for a purpose hereinafter described. The roughening can be accomplished in any suitable manner such as by embossing the plastic material with a pattern having raised portions therein.

Means is provided for inflating the balloon with a suitable medium, as for example a liquid such as a saline solution and a flexible tube 366 that extends into the balloon between the two sheets 363 and 364 and forms a fluid-tight seal therewith. The interior of the balloon can be inflated and deflated by introduction of the fluid through the tube 366. The tube 366 is connected to a Y-adapter 367 which has one leg of the Y connected to a one-way valve 368 having a Luer fitting and the other leg connected to a tube 369 which is connected to a tapered fitting 371. A conventional pinch off clamp 372 is mounted on the tube 369. The tube 366 is adapted to be releasably retained in the slots 360 of the shoulder 359.

Means is provided for removably securing the balloon 361 to the tunneling rod or shaft 306 and an elongate tubular member or sleeve 376 which extends along the length of the balloon 361 and is disposed on one side of the balloon 361 which can be called the top side generally centrally of the balloon 361. The tubular member 376 is provided with a passage 377 therein through which the tunneling or guide rod or shaft 333 extends. As hereinbefore explained, this tubular member or sleeve 376 can be formed as a separate member which is bonded to the top sheet 363 or alternatively can be formed integral with the top sheet 363 with two heat seals being provided above and below to form the sleeve 376 with the passage 377 therein. The tubular member 376 can be provided with spaced-apart elongate slits or perforations (not shown) extending along a line 378 in the tubular member 376 to facilitate separation of the balloon from the tunneling rod 333 as hereinafter described. With a such a construction it can be seen that the tunneling rod or blunt dissector or obturator 306 overlies the balloon 361 for advantageous features hereinafter described.

The balloon cover assembly 316 is a semi-rigid tube 381 formed of a suitable material such as plastic and is provided with proximal and distal extremities 382 and 383. It is provided with a bore 384 (see FIG. 42) which extends from the proximal extremity 382 to the distal extremity 383. The tube 381 is provided with a weakened region in the form of a partial slit 386 extending from the distal extremity 383 to the proximal extremity 382 of the tube 381 on the bottom side of the tube 381 as viewed in FIG. 40 (also see FIG. 42). The tube 381 is provided with a proximal end wall 387 which extends at a suitable angle, as for example 45° proximally with respect to the axis of the bore 384.

Figure 42:
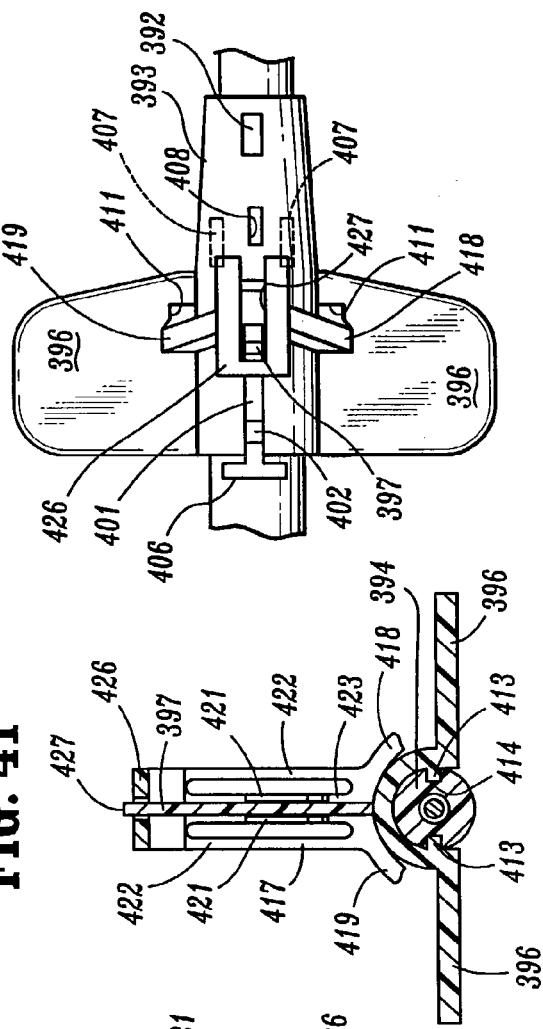
FIG. 42 is a top plan view looking along the line 42-42 of FIG. 41.
Figure 43:
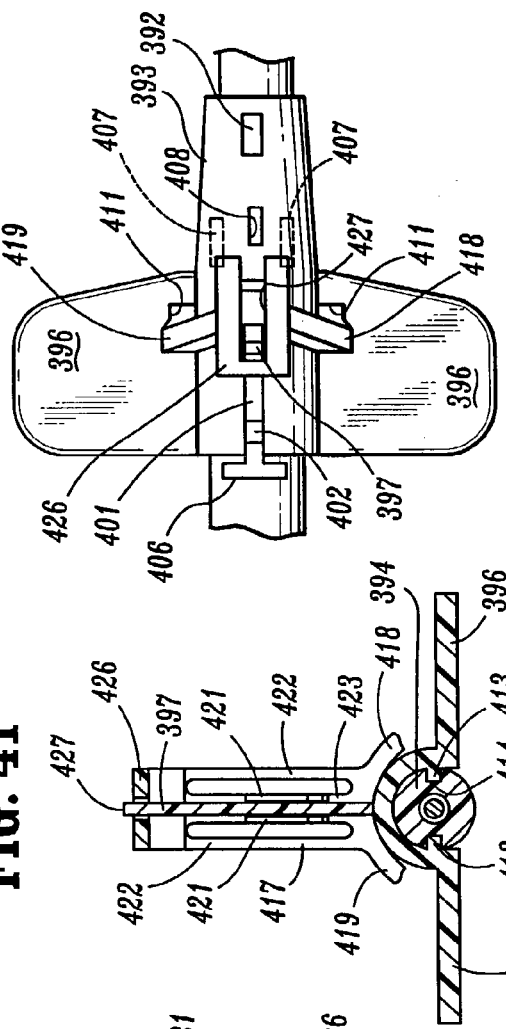
FIG. 43 is a view partly in cross section taken along the line 43-43 of FIG. 42.
Figure 44:
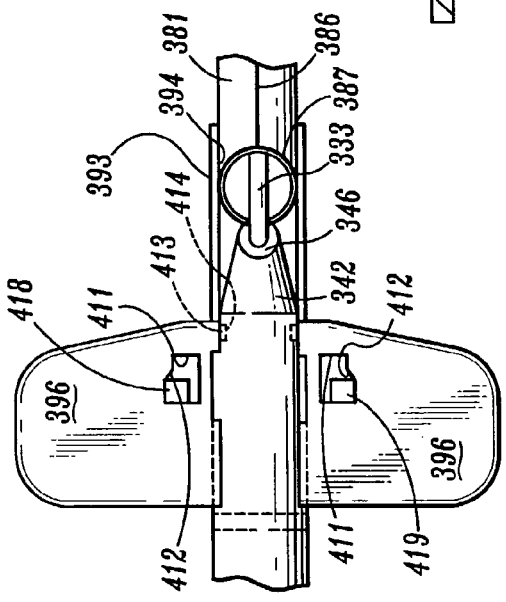
FIG. 44 is a view looking along the line 44-44 of FIG. 41.
Figure 45:
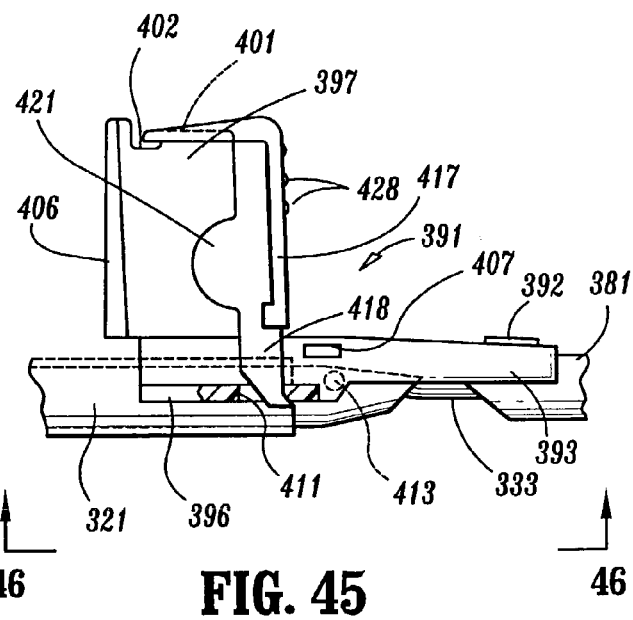
FIG. 45 is a partial side elevational view of the assembly shown in FIG. 1 with the clamping mechanism moved to a release position.
Figure 46:
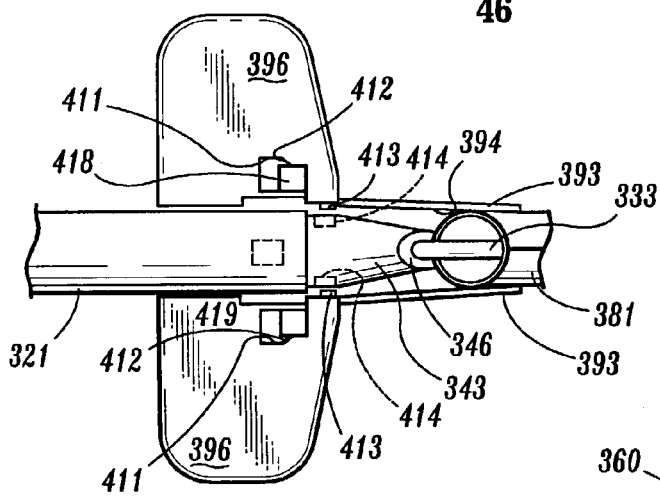
FIG. 46 is a view taken along the line 46-46 of FIG. 45.
Figure 47:
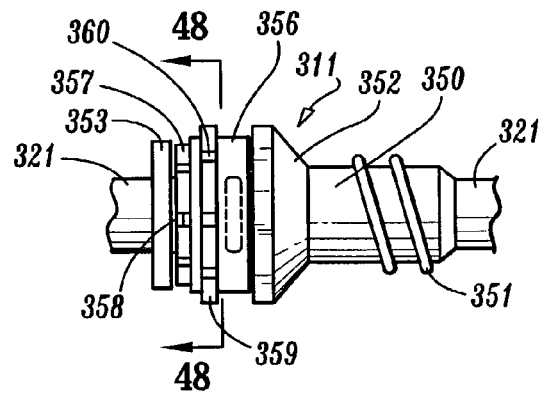
FIG. 47 is a partial side elevational view of an assembly shown in FIG. 41 with the retaining ring moved to a locked position.
Figure 48:
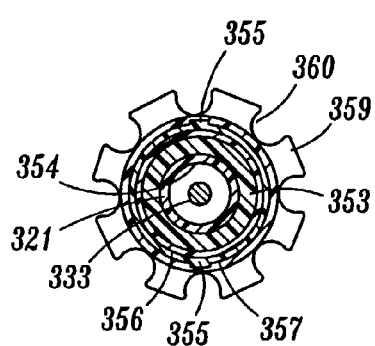
FIG. 48 is a cross-sectional view taken along the line 48-48 of FIG. 47.

The balloon cover assembly 316 also includes a handle 391 which as shown can be formed as a separate part and is secured to the proximal extremity 382 of the tube 381 by a metal clip 392. The handle 391 is provided with a tapered body 393 formed of a suitable material such as plastic which as shown in FIGS. 42 and 47 is open on the bottom side to make accessible a longitudinally extending recess 394 which is semi-circular in cross-section. A pair of sideways extending wings 396 are formed integral with the body 393 and lie in a plane which is substantially coincident with the axis of the semi-circular recess 394. As shown, the wings 396 are disposed at the proximal extremity of the body 393.

An upwardly extending fin 397 is formed on the body 393 substantially equidistant from the wings 396 in a direction generally perpendicular to the plane in which the wings 396 lie. The fin 397 is relatively narrow and is provided with an upper surface 378 having notches 401 and 402 therein. A vertically extending wall 406 is formed as a part of the fin 397 and extends generally in a direction which is perpendicular to the plane of the wings 396. The wall 406 extends in a direction at right angles to the fin 397 and has a gradually increasing thickness from the top to the bottom ends of the wall (see FIG. 46). The body 393 is provided with a pair of spaced-apart holes 407 spaced approximately 90° apart and 45° from each side of the fin 397. An elongate slot 408 is formed in the body 393 and is generally in alignment with the fin 397. A pair of camming slots 411 are provided on opposite sides of the body 393 in the wings 396 adjacent the distal extremities of the wings adjacent the body. The camming slots 411 are provided with inclined camming surfaces 412.

The body 393 is provided with a pair of diametrically disposed protrusions 413 which extend into the recess 394 and which are adapted to seat in a pair of diametrically opposed holes 414 provided in the distal extremity of the introducer member 342.

The balloon cover assembly 316 also includes a clamping member 416 which is provided with a central body 417 and a pair of downwardly extending legs 418 and 419 (see FIG. 43) which extend downwardly into the camming slots 411. As shown, the central body 417 is disposed just distal of the fin 397 and is provided with semi-circular guides 421 formed integral with the central body 417 and disposed on opposite sides of the fin 397 in a fulcrum region which is just slightly above the point of commencement of the legs 418 and 419. The central body 417 is provided with longitudinally extending reinforcing ribs 422 (see FIGS. 43 and 45). It is also provided with a proximally extending latch portion 426 which extends generally at right angles to the central body 417. The latch portion 426 is provided with a centrally disposed slot 427 extending substantially the entire length thereof which receives the upper extremity of the fin 397 so that when the clamping member 416 is snapped into placed over the body 393, the latch portion 426 is disposed in the notch 401 and cannot clear the uppermost portion of the fin 397. The clamping member 416 as hereinafter described is adapted to be moved between positions in which it is disposed within the notch 401 or alternatively in the notch 402. Laterally extending rounded raised portions 428 are provided on the central body 417 are adapted to be engaged by a finger of the hand when moving the clamping member 416 from the notch 401 to the notch 402.

Figure 49A:
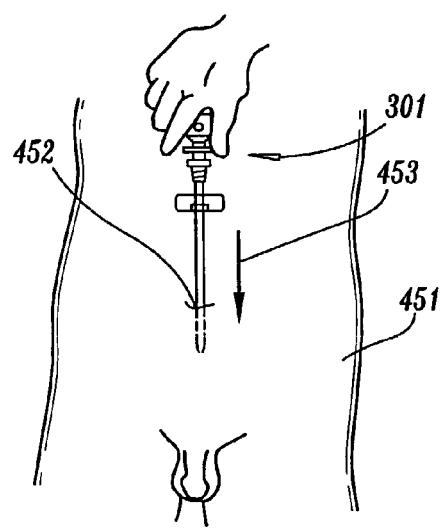
FIGS. 49A-49G are cartoons showing use of the surgical dissector shown in FIG. 1 in a laparoscopic hernia procedure.

Operation and use of the surgical balloon dissection apparatus 301 in performing the method for developing an anatomic space for laparoscopic hernia repair in connection with the apparatus shown in FIGS. 39-48 may now be briefly described as follows in conjunction with the cartoons which are shown in FIG. 49a through FIG. 49g. The surgeon in connection with the present method identifies the appropriate fascia layer to be dissected, either by direct visualization of the tissue and/or by manual palpation. Let it be assumed that it is desired to perform a hernia repair on a patient 451 and that it is desired to create an extraperitoneal working space for performing the surgical repair. The surgeon makes a small incision 452 in the skin of the patient in the umbilicus or slightly lateral of the umbilicus. A retractor (not shown) can then be utilized to open up the incision and to move it laterally to either side to locate the rectus muscles that run longitudinally of the body of the patient on both sides of the umbilicus or navel. As soon as the rectus sheath has been located, the incision is made in the rectus sheath through the incision previously made midway between the two sets of the rectus muscles. The surgeon then grasps the laparoscopic or balloon dissection apparatus 301 by using a hand, as for example his right hand as shown in FIG. 49A to grasp the handle assembly 337 to introduce the blunt end 331 into the incision to engage the anterior wall of the posterior rectus sheath. The balloon dissector 301 is then advanced longitudinally of the patient's body generally parallel to the two sets of rectus muscles as shown by the arrow 453 by using the rectus sheath as a guide to pass the blunt tip 331 to cause separation of tissue and to pass over the arcuate line and transversalis fascia to the level of the symphysis pubis. This can be readily accomplished with the balloon dissector 301 because the balloon cover assembly 316 is latched to and generally rigidly connected to the distal extremity of the introducer member 342 of the introducer device 307 by having the protrusions 413 provided on the tubular cover 381 seated within the holes 414 provided on the distal extremity of the introducer member 342. This provides a rigid assembly of the balloon dissector 301 so it can be operated by the surgeon grasping the handle assembly 337 without the need to have the physician grasp by the other hand an intermediate part of the balloon dissector to cause a desired manipulation and steering of the blunt tip 331 as the dissection of the tissue is accomplished as it is advanced.

The travel of the blunt tip 331 to the level of the symphysis pubis can be readily ascertained by the surgeon who can use his hand to palpate the abdominal region of the patient and thereby feel the blunt tip 331 as it is advanced until the blunt tip 331 strikes the symphysis pubis. This can be readily ascertained by the right hand holding the handle assembly 337 feeling the impact of the tip 331 striking the symphysis pubis 468 (see FIG. 50) which impact is communicated through the rigid structure of the balloon dissector to the handle assembly 337 where it can be felt by the hand of the surgeon. The balloon dissector 301 is then advanced a small additional amount so that the blunt tip 331 drops below the symphysis pubis 468.

Figure 49B:
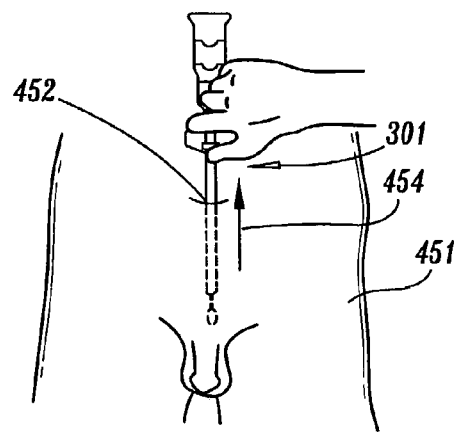
Figure 50:
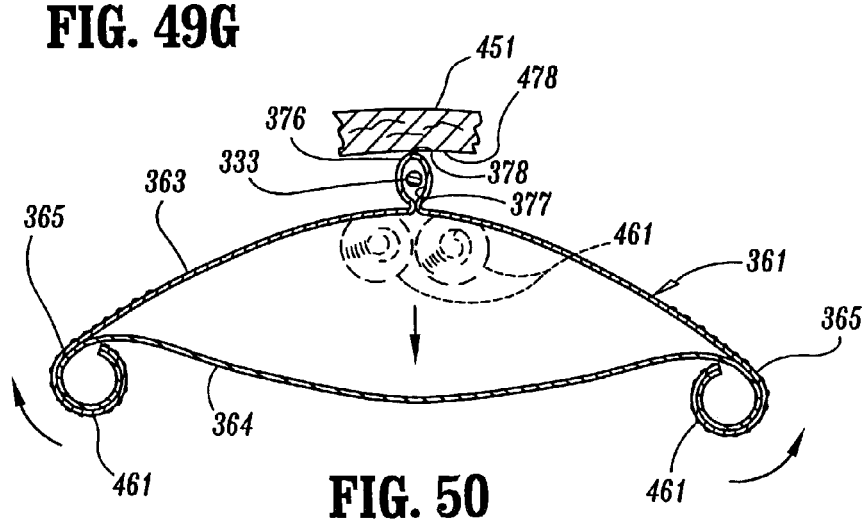
FIG. 50 is a cross-sectional view taken along the line 50-50 of FIG. 49C.

Thereafter, the balloon cover handle 391 is engaged by the same right hand of the physician as shown in FIG. 49B and the thumb is used to engage the transverse rounded protrusions 428 by moving the upper extremity of the clamping or latching member 416 proximally to cause the latch portion 426 to move into engagement with the notch 402 carried by the fin 397. As this is occurring, the legs 418 and 419 carried by the central body 417 are moved from the position shown in FIG. 42 to the position shown in FIG. 47 and in doing so engaging the camming surfaces 412 whereby the portions of the wings 396 secured to the body 393 are cammed outwardly so that the protrusions 413 are moved out of engagement with the holes 414. The direction of movement of the latch or clamping member 416 is indicated by the arrow 454 in FIG. 49B. As soon as the handle 391 has been released, the handle 391 is moved proximally with two fingers of the hand grasping the wings 396 to pull them upwardly and proximally to cause the balloon cover assembly 316 to be removed. The balloon 361 is held in place by the tunneling shaft or rod 336 and exits through the slit 386 provided at the bottom of the tubular cover 381 which serves as a tear away sheath. The balloon inflation tube 366 is retained in one of the slots 360 in the shoulders 359 so that it does not become entangled in the wings 396 as the balloon cover assembly 316 is removed. This exposes the balloon 361 which has its side margins rolled inwardly in rolls 461 with one being rolled in a counterclockwise direction and the other being rolled in a clockwise direction so that they underlie the tunneling rod 333 as shown in FIG. 50. Also to provide optimum dissection as hereinafter described before the rolling up occurs the forwardly extending protuberance 362 can be folded inwardly along a fold line 471 and the sidewardly extending lobe portions also can be folded inwardly along fold lines 472. To inflate the balloon the pinch off clamp 372 is closed and a conventional 60 cc syringe 476 containing a saline solution is connected to the one-way valve 368. The syringe 466 is then operated as shown by the arrow 477 to introduce the saline solution from the syringe 476 into the tubular member 366 and into the interior of the balloon 361 to gradually inflate the same. The one-way check valve 368 ensures that saline solution cannot exit therefrom when the syringe 466 is removed. The syringe 476 after it has been emptied can be removed and refilled with a saline solution which is introduced into the balloon in the same manner to cause the side margins of the balloon 461 to unwrap in opposite directions as shown in FIG. 50 on opposite sides of the tunneling rod 333 until they become completely unwrapped. Typically, it may take as many as approximately ten syringes of saline solution to cause the balloon 361 to completely unwrap and the move into an inflated condition as shown in FIG. 50. As the balloon is being filled and unwrapping, it continues to separate or dissect tissue overlying the peritoneum to provide an extraperitoneal working space between the transversalis fascia and the rectus muscles.

As hereinbefore described, the balloon 361 in plan has a symmetric manta ray-like configuration to provide the desired optimum extraperitoneal working space for the hernia repair. The forwardly extending protrusion 362 provided on the balloon 361 as it is inflated dissects distally from the distal extremity of the blunt tip 331 of the guide rod 333 serves to provide good dissection of tissue in the area of Cooper's ligaments and also to dissect laterally around the inguinal rings. By utilizing a symmetric manta ray-like construction, it is possible to provide a balloon 361 with its wide side margins or lobe portions 361a and 361b which when inflated to cause forward movement of the balloon 361 to dissect downwardly around the inguinal rings and to wedge the balloon 361 in place. The forwardly extending protrusion 362 as it is inflated dissects like a small balloon down to the Cooper's ligament. In this way, it is possible to obtain an extraperitoneal working space 478 which exposes all the desired anatomy at one time before moving off to the hernia sac and to do the final dissection for the hernia repair. By providing such a large extraperitoneal working space it is unnecessary to manually advance the dissection. The balloon has also been shaped to properly match the anatomy in which the procedure is to be formed so as to reduce to a minimum the amount of manual dissection which may be needed. Since the balloon has a particular shape and is formed of a non-elastomeric material, the dissection will occur in the desired locations which would not necessarily be the case if the balloon were formed of an elastomeric material which generally would have a tendency to follow the path of least resistance. Additional assurance is provided for ensuring that dissection will occur in the desired locations with the non-elastomeric balloon of the present invention because the balloon is held in place by the tunneling rod 333 underlying the symphysis pubis 468 as shown in FIG. 50. Also by providing roughened areas 365 these areas frictionally engage overlying tissue so that the lobe portions 361a and 361b can serve as anchors to prevent displacement of the balloon 361 after the balloon 361 as it is being inflated.

Figure 49C:
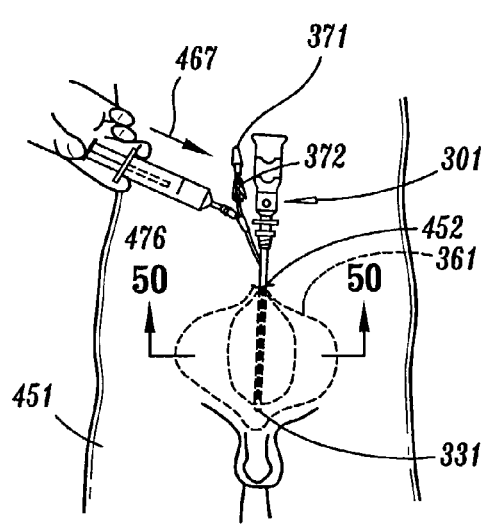

After the amount of desired tissue dissection has taken place by inflation of the balloon 361 to provide the extraperitoneal working space, the balloon 361 is deflated by connecting the evacuation fitting 371 into an evacuation port (not shown) of an operating room suction system. The pinch clamp 372 is released to open the tube 369 to permit the saline solution which had been introduced into the balloons 361 to be sucked out to completely deflate the balloon from the inflated condition as shown in FIG. 49C.

Figure 49D:
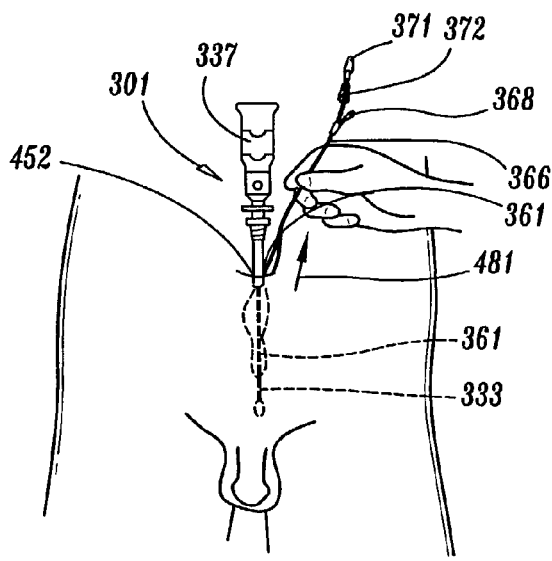
Figure 49E:
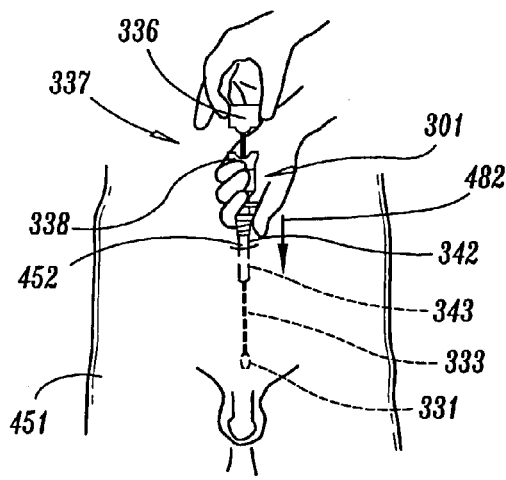

After the balloon has been deflated, the tubular member 366 can be grasped by the fingers of the hand as shown and the deflated balloon 361 pulled out through the incision 452 in the direction as shown by the arrow 481 in FIG. 49D. If necessary, the handle assembly 337 can be held by the other hand. The balloon 361 as it is being pulled off has its sleeve 376 separates from the tunneling or guide rod 331 by breaking through the linear perforations lying along the line 378. The guide rod 331 remains in place to preserve an easy entry into the extraperitoneal space which has been created. The balloon 361 can then be discarded.

After the balloon 361 has been removed, the left hand is used to grasp the lower second handle part 38 with the left hand while the right hand engages the upper or first handle part 336 of the handle assembly 337. The fingers of the right hand then engage the latch members 339 on opposite sides by the fingers of the hand to release the first part 336 from the second part 338 and to permit the left hand to move the second part 338 in the direction of the arrow 482 shown in FIG. 49E. The second part 338 carries with it the cannula 302 attached thereto and the introducer device 307 which extends therethrough with the skin seal assembly 311 mounted on the cannula tube 321. This advancement over the guide rod 333 is continued until the distal extremity 343 of the introducer member 342 has been advanced into the desired position. As soon as this has been accomplished, the skin seal assembly 311 is slidably advanced on the cannula tube 321 until the skin seal approaches the incision 452. The screw body 351 is then rotated by the fingers of the hand engaging the flange 352 and/or to the shoulder 359 to screw it into the incision 452 and to form a gas tight skin seal with the skin of the patient. As soon as a good skin seal has been established, the introducer device 307 is clamped in a fixed position with respect to the skin seal assembly 311 by pushing generally downwardly on the collar 356 to engage the collet 357 to form a friction grip between the elastomeric insert 353 and the cannula tube 321.

Figure 49F:
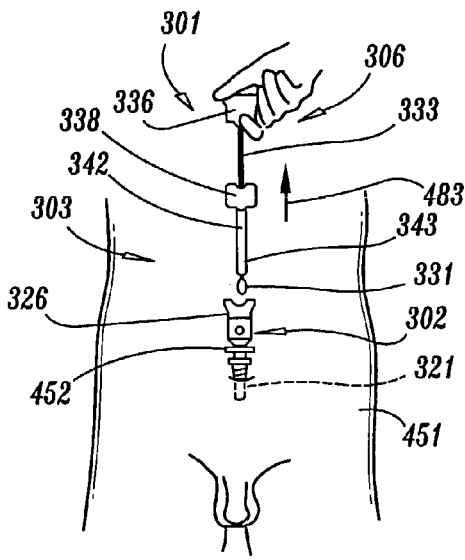
Figure 49G:
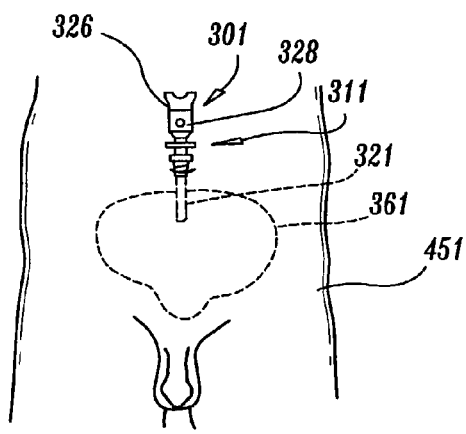

After the cannula 302 is in a fixed in position, the blunt obturator 306 can be removed along with the tunneling device or blunt obturator device 303. This is accomplished merely by continuing to pull upwardly on the handle part 336 with the hand in the direction indicated by the arrow 483 as shown in FIG. 49F. As this pulling motion continues, the blunt tip 331 will engage the distal extremity 343 of the introducer member 342 causing a withdrawal force to be applied to the second handle part 338 to cause it to automatically release from the housing 326. This permits the blunt obturator device 303 to be removed through the cannula tube 321. This is possible because the blunt tip 331 has a diameter which can pass through the interior of the cannula tube 321 and through the valving provided in the housing 326. In withdrawing the guide rod 333 carrying the obturator tip 331, it can be seen that it continues to be guided by the introducer member 342 and thus will remain centered with respect to the cannula tube 321 to avoid any pinching action at the distal end 323 of the cannula tube 321. As soon as the obturator tip 331 strikes the introducer member 342, the handle part 338 is automatically disengaged from the cannula handle 326. The latch parts 349 are substantially buried within the second handle part 338 so they are relatively inaccessible to the surgeon ensuring that he will operate the latch parts 339 carried by the first handle 336 which helps to ensure that the surgeon remove the handle parts 336 and 338 in two stages.

After this has been accomplished a source of gas such as carbon dioxide is connected to the stop cock valve 328. The stop cock valve 328 is opened to permit the carbon dioxide to inflate the dissected extraperitoneal working space such as indicated by the dotted lines 476 shown in FIG. 49G. The cannula 302 can then be utilized for introducing instruments of various types into the dissected extraperitoneal working space. The inflation gas cannot escape because of the valving provided in the handle 326 of the cannula 302.

Additional cannulae can be introduced in various positions in the abdomen of the patient through which additional surgical instruments can be introduced for performing the surgical procedure to be performed in the extraperitoneal working space. The remainder of the hernia repair procedure to be accomplished in the extraperitoneal working space is substantially the same as hereinbefore described and therefore will not be described in detail. By way of example, let it be assumed that a hernia sac has been formed in the patient, as for example by passing down into the scrotum to form a typical indirect hernia. The hernia sac can be pulled out and ligated in a manner hereinbefore described. Thereafter, a piece of mesh as hereinbefore described can be introduced through another site and rolled out over the region through which the sac had previously passed. The mesh can then be stapled in place, as for example along the Cooper's ligament. After the hernia repair has been completed, the extraperitoneal working space can be deflated by opening the stop cock valve 328 and bleeding the $CO_2$ contained therein to atmosphere to permit the abdominal wall to return to its normal position to help retain the mesh which has been placed in the desired position.

In connection with the formation of the extraperitoneal working space with the apparatus of the present invention, it has been found that it is desirable to have the guide rod 333 be in position in which it overlies the balloon 361 because this helps to ensure that the balloon dissection will occur in appropriate areas because the blunt tip 331 underlying the symphysis pubis is retained in the desired position even during the time that the balloon is unrolling during inflation. Positioning the guide rod 333 in this manner, ensures that the balloon 361 will roll out in the opposite directions from the rod and also to help to push the balloon downwardly during inflation.

In order to make the apparatus more user friendly, the parts which are to be moved for operation with respect to other parts have been color coded, as for example they can be colored black with the remaining parts being of another color, such as grey or white. Thus, the clamping or latch member 416 is of a black color because it must be removed to unlatch the balloon cover assembly 316. Similarly, the collar 356 of the skin seal assembly 311 is of a black color because it must be moved to clamp the cannula 302 in a desired position.

Similarly, the latch parts 339 and 349 are of black color because they also must be moved to separate the handle parts.

The wings 396 are provided on the balloon cover 316 in addition to serving as means to facilitate grasping of the balloon cover assembly 316 when it is desired to remove the same, as serve to visually indicate the plane in which the balloon 361 of the balloon dissection apparatus 301 causes dissection. Generally this dissection plane is in a plane which is parallel to the plane in which the wings 396 lie.

As hereinbefore explained, the introducer member 342 is provided with an obturator end surface or tip which is inclined at an angle in a direction away from the normal direction of insertion to inhibit any tendency that the tip might hang up on tissue as it is being advanced through the tissue during dissection.

The sizing of the blunt obturator tip 331 so it is smaller than the inner diameter of the cannula tube 321 helps to ensure that tissue will not become entrapped or pinched between the tip 331 and the cannula tube 321. In addition, as hereinbefore described, the obturator tip 331 is tapered in both directions into a smaller dimension from the center to also minimize the possibility of any tissue being entrapped between the tip 331 and the cannula tube 321 and thereby ensuring that a shearing action will not occur.

In conjunction with the foregoing disclosure, it has been assumed that the balloon dissection apparatus hereinbefore described typically would be disposed of after each use. In the event it is desired to economize and it is desired to reutilize at least certain portions of the balloon dissection apparatus after a use in a laparoscopic procedure, another embodiment of a balloon dilatation apparatus 501 incorporating the present invention is shown in FIGS. 51-55. As shown therein it comprises a handle assembly 502 similar to the handle assembly 337 hereinbefore described which includes a handle part 503 similar to the handle part 336. Other parts of the balloon dissection apparatus 501 are not shown because they can be identical to those hereinbefore described. The handle part 503 is provided with two sections 506 and 507 which can be fastened together in a suitable manner such as by ultrasonic bonding or an adhesive. Latch members 511 and 512 are provided on opposite sides of the handle part 503 and are provided with finger portions 513 that are adapted to be engaged by fingers of the hand which extend outwardly through recesses 514 in the sections 506 and 507. The latch members 511 and 512 are each provided with a latch 516 which is yieldably urged in an outward direction by a yieldable spring member 517 engaging a downwardly depending lip 518 provided within the sections 506 and 507. The latch members 511 and 512 are pivotally mounted between the sections 506 and 507 by pivot pins 519 formed integrally on the latch members 511 and 512 and extending into bosses 521 provided in the sections 506 and 107 which are formed of a suitable material such as plastic.

First and second inserts 526 and 527 formed of a suitable material such as plastic are mounted in the sections 506 and 507. First and second latch members 531 and 532 formed of a suitable material such as metal are provided which are seated in recesses 533 and 534 provided in the insets 526 and 527. The latch members 531 and 532 are generally U-shaped and are yieldably urged into engagement with each other to form an elongate slot 536 extending therethrough. Upstanding legs 538 formed integral with the inserts 526 and 527 are provided in rectangular spaces 539 in the inserts 526 and 527 so that the upper extremities of the legs 538 can be flexed by movement of the latch members 531 and 532 as shown by dotted lines in FIG. 54.

A guide rod 541 is provided which is similar to the guide rod 333 with the exception that its distal extremity 542 is also provided with an annular recess 533. The distal extremity 542 is provided with a chamfer 544 and a pair of opposed flats 546 which extend through the chamfer 544. The guide rod 541 extends through a hole 551 provided by semicircular recesses formed in the sections 506 and 507 and by a hole 552 formed by semicircular recesses in the inserts 526 and 527. A larger hole 553 formed by semicircular recesses in the inserts 526 and 527 of a larger diameter than the hole 552 is provided which receives a push-button 556 and extends through a hole 557 also formed by semicircular recesses provided in the sections 506 and 507. A dish-shaped or concave recess 558 is provided in the sections 506 and 507 and facilitates engaging the push-button 556 by a finger of the hand.

The pushbutton 556 is provided with a bore 561 which is sized so that it can receive the distal extremity 542 of the guide rod 541. The pushbutton is provided with sideways extending skirts 562 extending 180° with respect to each other and which are provided with distally and inwardly extending camming surfaces 563 which terminate at a tip 564 that is generally V-shaped as shown in FIG. 51. The tip 564 is formed so that it is adapted to enter into the slot 536 formed by the U-shaped members 531 and 532. Thus, when the pushbutton 556 is depressed, the tip 564 will enter the slot 536 in a progressive manner to urge them apart so that the camming surfaces 563 carried thereby engage the U-shaped latch members 531 and 532 in regions just above and below the guide rod 541 so that the guide rod 541 is released by the U-shaped latch members 531 and 532 permitting it to be pulled out of the handle part 503. Release of the guide rod 541 makes it possible to separate the guide rod 541 from the remainder of the balloon dissection apparatus 501 so that the handle assembly 502 and the other parts carried thereby can be separated from the guide rod. Thereafter, the guide rod 541, the balloon 361 and the balloon cover assembly 316 can be disposed of. The other parts of the apparatus can be reutilized after appropriate sterilization. In order to ensure that the other parts survive sterilization, it may be desirable to form the plastic reusable parts of a suitable plastic such as a polysulfone.

In connection with the foregoing, it can be seen that by making minor changes in the construction it is possible to save a great number of parts of the balloon dissection apparatus for reuse after sterilization. Only the parts which are most difficult to clean are disposed of after a one-time use.

Figure 56:
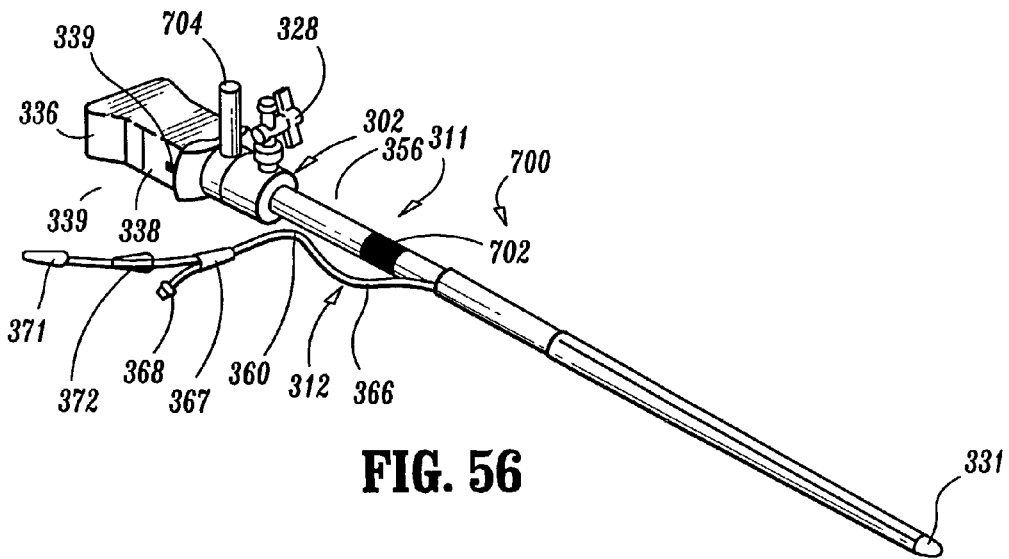
FIG. 56 is an isometric view of an alternative embodiment of a surgical dissector with a cannula incorporating the present invention in an assembled condition without the balloon cover handle.

Another embodiment of a laparoscopic dissection apparatus is shown in FIGS. 56-69. For ease of understanding, some of the elements in FIGS. 56-69 are referenced with reference numerals that are the same as those used in previous figures. The assembly 700 is a surgical dissector with a cannula which serves as a hand manipulated surgical instrument that can be used during laparoscopic surgical procedures to dissect tissue layers as described in conjunction with the previously disclosed embodiments of the invention. The assembly 700 includes a cannula 302 with a tunneling device 306 mounted therein. The tunneling device or guide rod 306 comprises of a blunt tip obturator 331, an tunneling rod 333, and a tunneling rod guide assembly 600. The laparoscopic apparatus also includes a skin seal assembly 701, a balloon assembly 312 and a balloon cover assembly 316 as shown particularly in FIGS. 56 and 57.

The cannula 302 comprises a cannula tube 321 formed of a rigid plastic having proximal and distal extremities 322 and 323. A flow passage 324 or lumen extends from the proximal extremity 322 to the distal extremity 323. A cannula housing or handle 326 is mounted on the proximal extremity by suitable means such by molding it directly thereon. As disclosed U.S. Pat. No. 5,324,270, the disclosure of which is incorporated by reference herein, the handle 326 includes first and second internal seal members (not shown) in which one seal member serves as a duck-bill valve and the other seal member serves as an instrument seal. The housing is provided with a Luer-type fitting 327 which is in communication with the interior of the housing distal of the duck-bill valve and is in communication with the passage 324 in the cannula tube 321.

Figure 60:
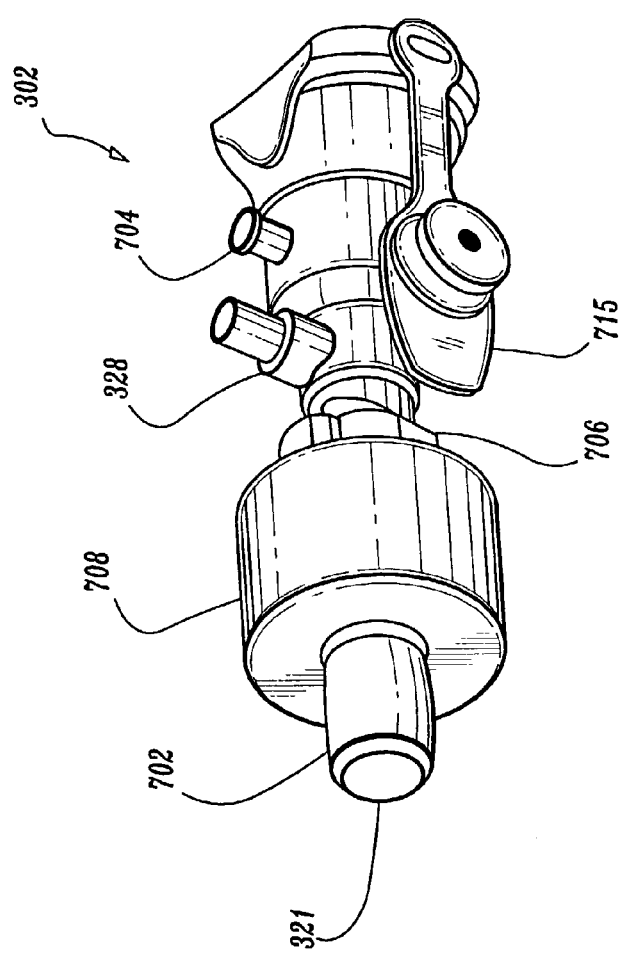
FIG. 60 is an isometric view of an alternative embodiment of the cannula with skin seal apparatus in a deflated state.
Figure 61:
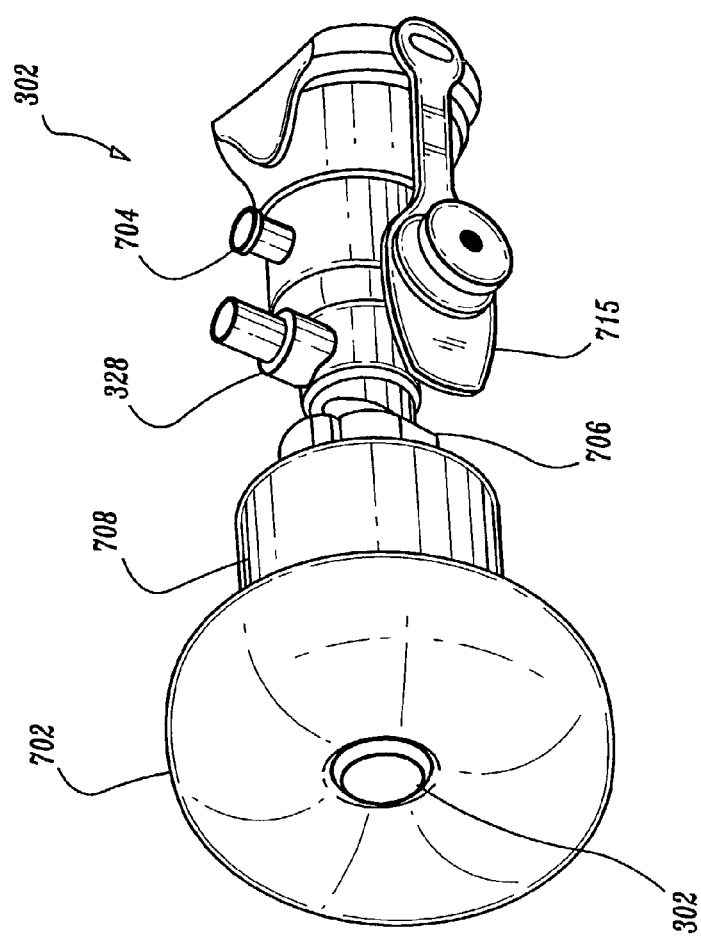
FIG. 61 is an isometric view of an alternative embodiment of the cannula with skin seal apparatus in an inflated state.

Circumnavigating or surrounding the distal end portion of the cannula tube 321 is a toroidal shaped balloon that serves as a skin seal balloon 702. This is best shown in FIGS. 60 and 61. In a deflated state, the skin seal balloon is generally the same diameter as outside of the cannula tube 321. In an inflated state, the skin seal balloon is generally 2 to 3 times the diameter of the cannula tube 321. In alternate embodiments, the skin seal balloon 702 may be of a different shape and size to meet the needs of a particular application. The inner volume of the skin seal balloon is in fluid communication with an skin seal fluid port 704 located on the upper face of the cannula 302. The fluid may comprise air, liquid or gel type material. In one embodiment, an outer cannula tube 321 partially or completely surrounds the outer diameter of an inner cannula tube not shown to thereby achieve the fluid communication between the skin seal balloon 702 and the skin seal port 704 through the annulus between said tubes. Alternatively, the fluid communication between the skin seal port 704 and the skin seal balloon 702 may be through a lumen in the wall of the cannula tube 321. Also shown in FIGS. 60 and 61 is a reducer 715 to adapt the proximal end of the cannula to accept different sized or diameter inserts.

It is contemplated that any suitable device may connect to or be integral with the skin seal port 704 to facilitate the entry of fluid into the skin seal balloon 702 and prevention of fluid out of an inflated skin seal balloon until such time as such deflation of the skin seal balloon is desired. A check valve which can be mechanically opened is useful for this purpose. These devices include but are not limited to a stop-cock valve 328, shown in FIG. 58, having a hose connector barb as one possible connector means, a tubing pinch-off device or a syringe.

A cannula skin seal clamp 706 resides on cannula tube 321 and may be selectively located by a user at any axial position on the cannula tube intermediate the enlarged proximal end 327 and the skin seal balloon 702 of the cannula. In one embodiment the cannula skin seal clamp 706 comprises a securing device 710 to secure the cannula skin seal clamp to a particular location along the cannula tube 321, a resilient skin contact portion 708 to press against the patient's skin to further assure a generally fluid tight skin seal. As shown the resilient skin contact portion 708 comprises a tubular section of foam configured circularly around the cannula tube 321. Adhesive or some other connection means connects the securing device 710 to the resilient skin contact portion 708. Use of the skin seal clamp 706 and skin seal balloon 702 is described in greater detail below.

As described in said U.S. Pat. No. 5,324,270, the cannula 302 is adapted to receive the tunneling device 306.

Tunneling device 306 is provided with a blunt tip 331 which is generally olive-shaped as shown (see FIG. 62) and is formed of a suitable material such as plastic. The olive-shaped tip 331 is molded on the distal extremity 332 of a tunneling rod or a shaft 333 formed of a suitable material such as stainless steel. The blunt tip 331 is sized so that its outside diameter is slightly less than the inside diameter of the cannula tube 321.

The proximal extremity 334 of the rod or shaft 333 has mounted thereon a handle part 336. The handle part 336 is adapted to mate with the handle part of the proximal end of the cannula housing 326. The handle part 336 and cannula housing 326 can be detachably connected by the use of latch means (not shown) adapted to be actuated by biased latch members 339 disposed on opposite sides of the handle part 336 and further adapted to be engaged by the fingers of the hand holding the handle part for latch release.

Accordingly, the cannula housing 326 is also provided with latch means (not shown) which is adapted to releasably connect the handle part 336. The cannula housing 326 includes latch receiving members 349 disposed on opposite sides of the cannula housing that mate with the latches of the handle part 336 to permit the handle part to be releasably connected to the cannula housing.

Figure 62:
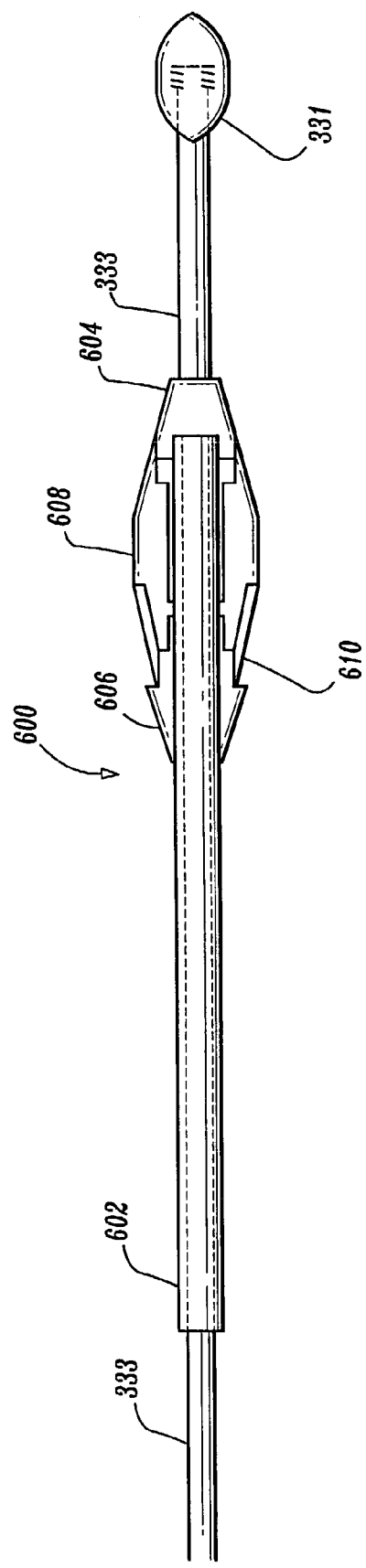
FIG. 62 is a side plan view of the tunneling rod guide assembly of an alternative embodiment of the present invention.
Figure 62A:
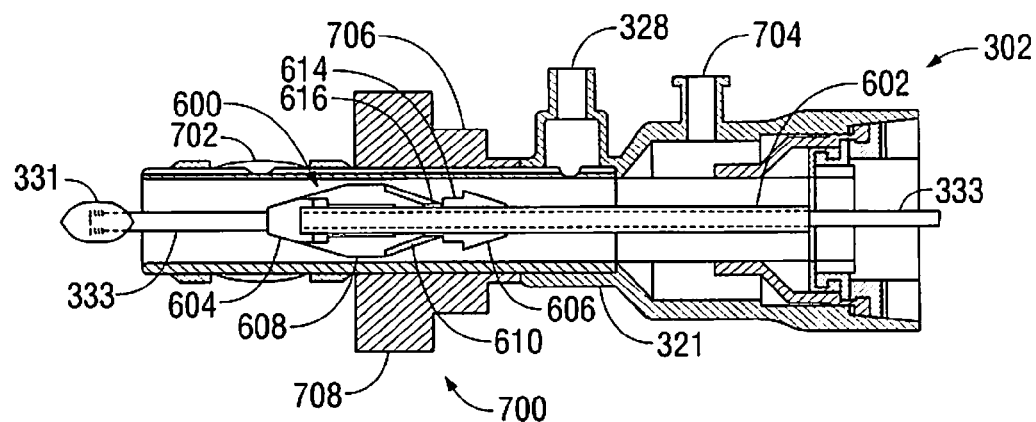
FIG. 62A is a cross-sectional view of the tunneling rod guide assembly of FIG. 62 shown in a first state and disposed within the cannula with skin seal apparatus of FIG. 60.
Figure 62B:
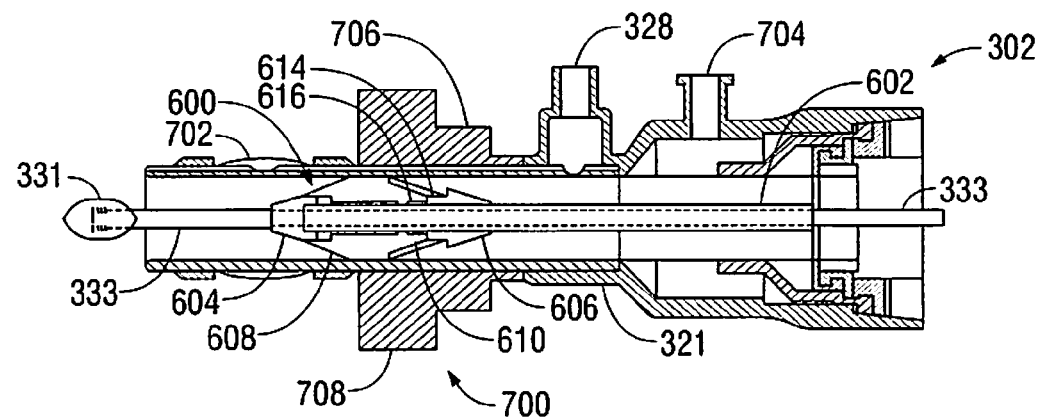
FIG. 62B is a cross-sectional view of the tunneling rod guide assembly of FIG. 62 shown in a second state and disposed within the cannula with skin seal apparatus of FIG. 60.
Figure 63:
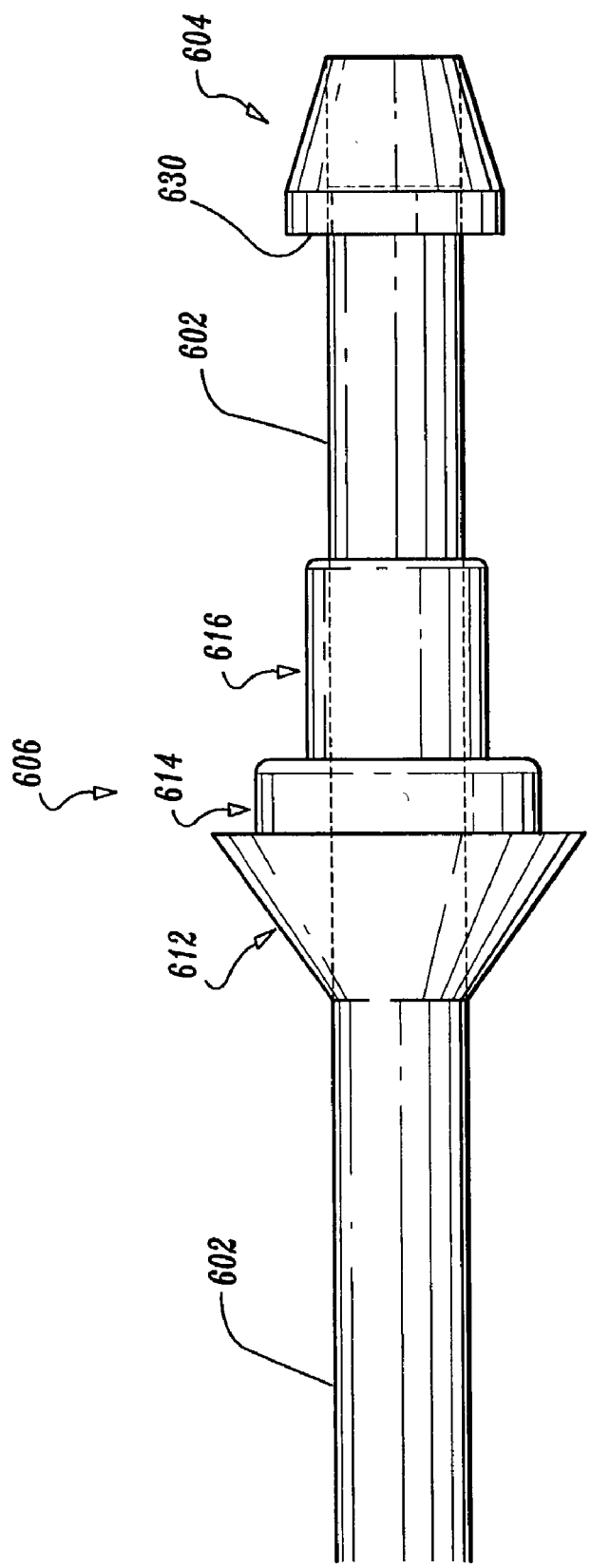
FIG. 63 is a side plan view of the inner collar and end collar on the sleeve of the tunneling rod guide assembly.
Figure 64D:
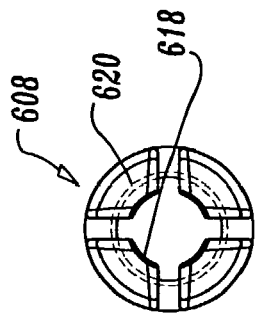
FIG. 64D is an end plan view from the distal end of the guide collar.
Figure 64C:
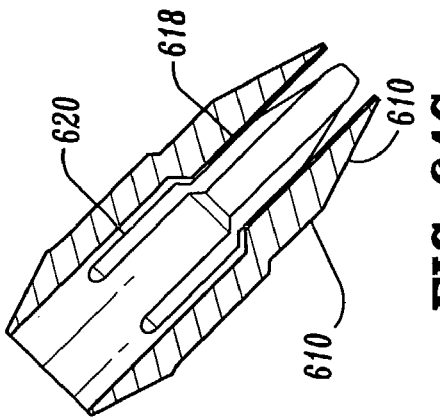
FIG. 64C is a cross-sectional top plan view of the guide collar of the tunneling rod guide assembly.
Figure 64A:
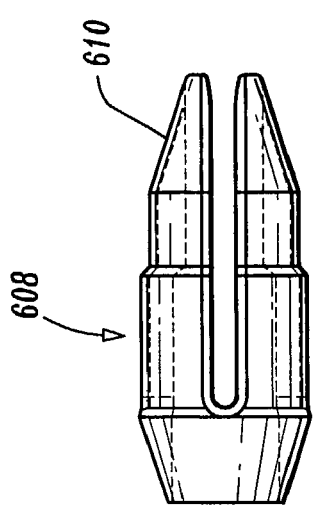
FIG. 64A is a side plan view of the guide collar of the tunneling rod guide assembly.
Figure 64B:
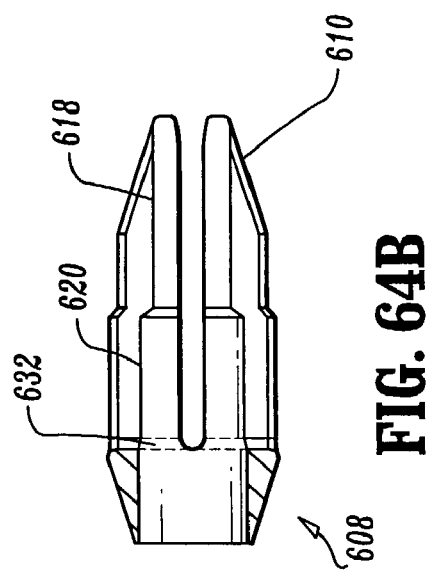
FIG. 64B is a side plan view of a guide collar rotated along the guide collar center axis.

In reference to FIGS. 62 and 63, a tunneling rod guide 600 is located on the rod intermediate the tunneling rod blunt tip 331 and the handle 336 of the tunneling device 306. The tunneling rod guide 600 comprises a sleeve 602, a tapered end collar 604, a ledged inner collar 606, and a movable guide collar 608 with expanding and contracting fingers 610. Each aspect is now described in detail.

The sleeve 602 comprises a hollow tube section having inner diameter slightly greater than the outer diameter of the tunneling rod 333. The sleeve is free to move longitudinally along the length of the tunneling rod 333. Prior to use and during use of the device until prior to the removal of the tunneling device 306, the sleeve 602 resides largely within the cannula 302. Advantageously, the diameter of the sleeve 602 is only slightly greater than the diameter of the tunneling rod 333. As such, the diameter of the sleeve is sufficiently small so as to not cause permanent set of the duck bill gas seal in the cannula 302 during sterilization and storage. Set of the duck bill seal will allow insufflation gas to escape from the patient later during the surgical procedure.

Mounted on the distal end of the sleeve 602 is a tapered end collar 604. The tapered end collar 604 is best illustrated in FIGS. 62-63. As shown the tapered end collar 604 permanently connects to the distal end of the sleeve 602. The inner diameter of the tapered collar 604 is generally the same as the outer diameter of the sleeve 602. During retraction of the tunneling rod 333, the blunt tip 331 on the distal end of the tunneling rod contacts the tapered end collar 604 thereby pulling the sleeve 602 proximally out of the cannula 302. Operation of the tunneling rod guide 600 is discussed in more detail below.

An inner collar 606 is also attached to the sleeve 602 at a location proximal from the distal end of the sleeve as shown in FIG. 63. From a proximal direction to a distal direction, the inner collar 606 comprises a tapered section 612, a first shoulder 614, and a second shoulder 616. The tapered section 612 inclines from a diameter generally identical to the outer diameter of the sleeve 602 to a diameter generally greater than the first shoulder 614. The outer diameter of the first shoulder 614 is generally greater than the outer diameter of the second shoulder 616. The outer diameter of the second shoulder 616 is generally intermediate the outer diameter of the first shoulder 614 and the outer diameter of the sleeve 602. The outer diameter of the end collar 604 and the inner collar 606 are less then the inner diameter of the cannula tube 302.

Figure 65:
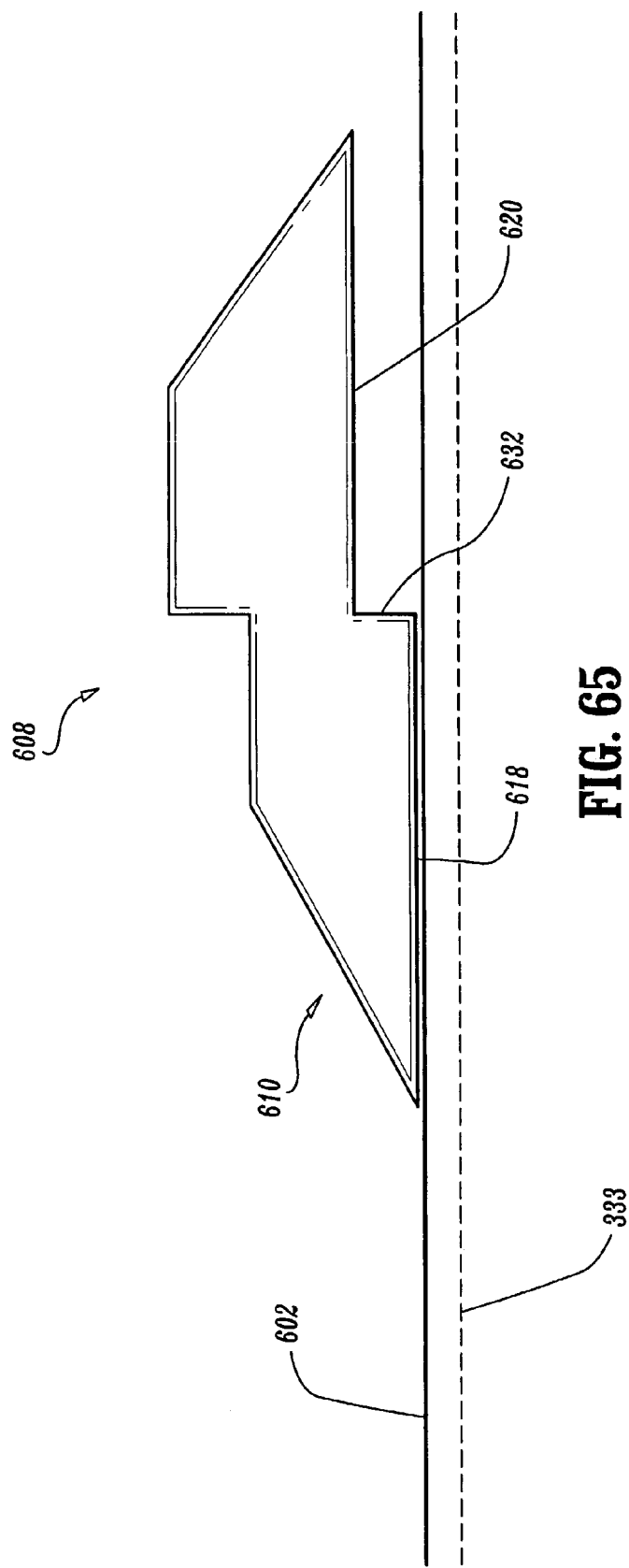
FIG. 65 is an enlarged cross-sectional view of the guide collar in relation to the upper surface of a tunneling rod.
Figure 66:
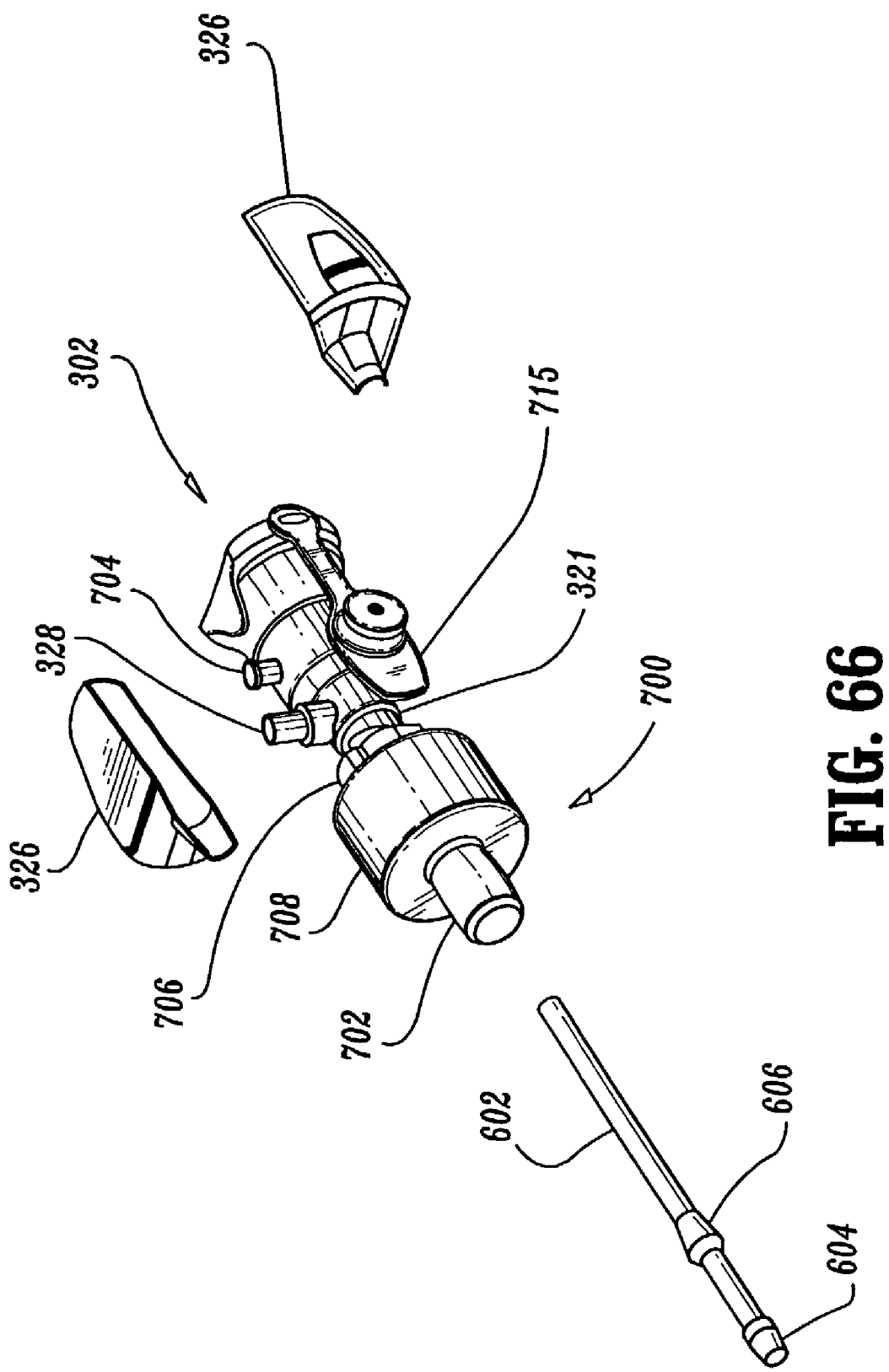
FIG. 66 is an isometric view of the rod guide assembly, cannula with integrated skin seal and handle as found in an alternative embodiment of the present invention.

In reference to FIGS. 64 and 65, a movable guide collar 608 with expandable fingers 610 resides generally intermediate the end collar 604 and the inner collar 606 and likewise surrounds the tunneling rod 333. The movable guide collar 608 comprises a hollow tubular portion having fingers 610 on the proximal end. The inner diameter of the guide collar 608 is stepped such that the proximal inner diameter 618 is less then the outer diameter of the end collar 604. The distal inner

620 of the guide collar 608 is greater than the outer diameter of the end collar 604. Such stepped configuration allows the guide collar 608 to move between a first position wherein the guide collar is prevented from further motion in the proximal direction by the fingers 610 contacting the stepped edge of the second shoulder 614 on the inner collar 606 and second position wherein the guide collar is prevented from further motion in the distal direction by the ledge created by the smaller inner diameter 618 of the guide collar 606 contacting the proximal edge of the end collar 604. The significance of this first position and this second position is discussed below in greater detail.

The movable guide collar 608 is preferably composed of a somewhat flexible plastic or nylon type material having fingers 610 formed from cantilvered sections connected only on the distal end to the guide collar. In another embodiment the finger 610 are formed by removing materal from between each finger in some manner of a machining process to thereby create the proximally extending fingers. Such configuration allows each finger 610 to flex radially outward to a degree sufficient to expand over the second shoulder 610 on the inner collar 606. Operation of the guide collar 608 and sleeve 602 is described below in greater detail.

It should be noted that when the fingers 610 of the guide collar 608 are expanded around the first shoulder 614 of the inner collar 606 the outer diameter of the guide collar is greater than the inner diameter of cannula tube 321. Accordingly the guide collar 606 will not slide into the cannula tube 321 since the outer diameter of the guide collar is greater than the inner diameter of the cannula tube. Likewise, the sleeve 602 and end collar 604 and inner collar 606, are also prevented from movement within the cannula tube 321 since the ledge 630 on the proximal end of the end collar 604 contacts the ledge 632 on the inner diameter of the guide collar 608. To reduce the diameter of the guide collar 608 the guide collar must move in the distal direction with relation to the sleeve 602 and inner collar 606 so that the fingers 610 of the guide collar generally rest on the second shoulder 616, the second shoulder being of reduced diameter as compared to the first shoulder 614.

Movement of the guide collar 608 in general is achieved by movement of the connected sleeve 602, and end collar 604 with relation to the guide collar. Such movement is achieved by force excereted by the proximal end 332 of the blunt tip 331 as the tunneling rod 333 is moved in the proximal direction through the cannula 302 the guide collar 608 is prevented from movement in the proximal direction by the fingers 610 on the first shoulder 614 of the cannula tube. After application of sufficient force on the tunneling rod 333 in the proximal direction the blunt tip 331 moves the sleeve 602, and inner collar 606 connected thereto, a sufficient distance causing the guide collar fingers 610 to slip from the first shoulder 614 to the second shoulder 616. Because the second shoulder 616 is of smaller outer diameter than the first shoulder 614, the outer diameter of the guide collar 608 is now reduced sufficiently to slide within and through the cannula tube (lumen) 321.

Stated another way, the blunt tip 331 contacts the end collar 604 just prior to the blunt tip moving into the cannula tube 321. Advantageously, the guide collar 608 remains in place, being unable to fit into the cannula tube 321, until the blunt tip 331 is ready to enter the cannula tube. This desirably centers the tunneling rod 333 and blunt tip 331 during the entire tunneling rod extraction process and further reduces the opportunity for pinching or tearing of patient tissue between the blunt tip and the distal end of the cannula tube 321. When pressure is applied by the proximal end of the blunt tip 331 to the end collar 604, which is connected to the sleeve 602, the fingers 610 of the guide collar 608 are forced to slide from the first shoulder 614 to the second shoulder 616. Movement of the proximal end of the fingers 610 to the reduced diameter second shoulder 616 allows the fingers to assume a shoulder 616 smaller diameter which in turn allows the guide collar 608 to fit into the cannula tube 321. In this manner the guide collar 608 remains in place to center and guide the tunneling rod 333 until contacted by the blunt tip 331.

Figure 57:
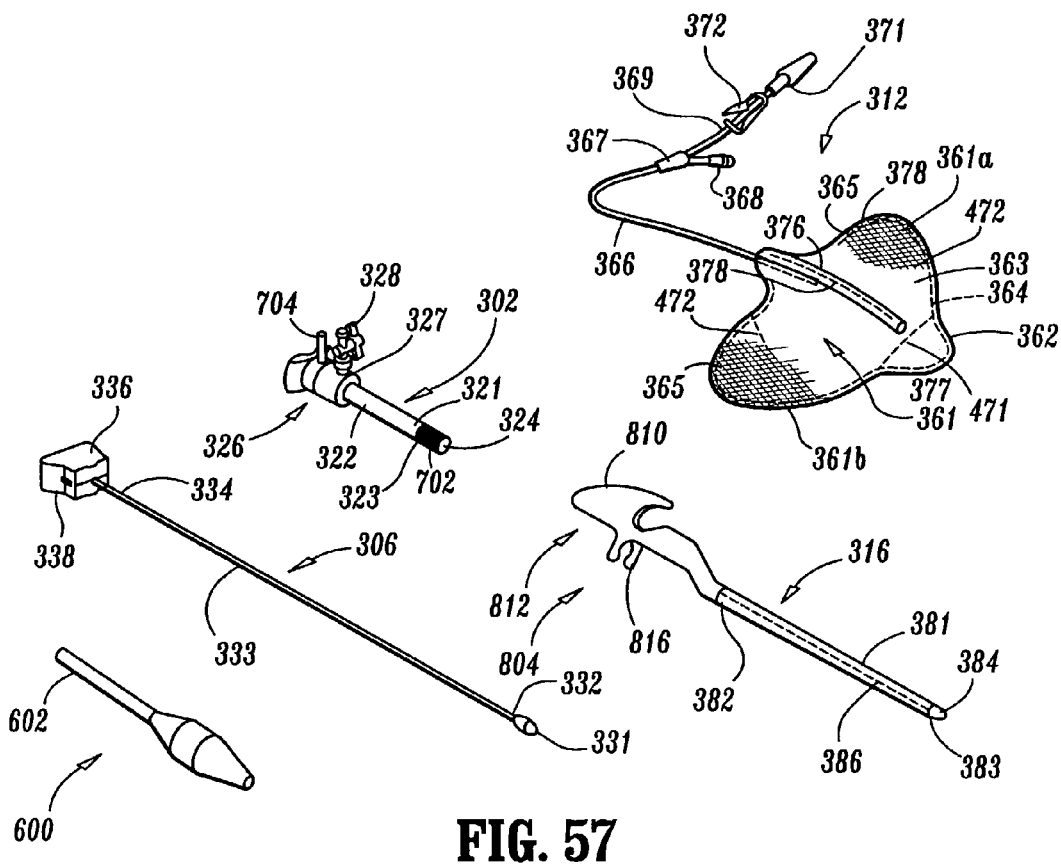
FIG. 57 is an isometric exploded view of the components of an alternative embodiment of the surgical dissector with cannula shown in FIG. 56.

The balloon assembly 312 comprises a balloon 361 formed of a non-elastomeric, medical grade plastic material of a suitable type such as polyurethane. The balloon 361 can be characterized as having a symmetric manta ray configuration about the guide rod when viewed in plan and may be provided with a forwardly extending rounded protuberance 362 which has a width substantially less than that of the balloon 361. The balloon 361 comprises one or more sheets of material which can be identified as a first or upper sheet 363 and a second or lower sheet 364 which have been die cut to the desired configuration with their edges bonded together in a suitable manner such as by means of a heat seal to form a balloon which has a generally flat configuration when deflated as shown in FIG. 57.

Means is provided for inflating the dissection balloon with a suitable medium, as for example a liquid such as a saline solution and comprises of a flexible tube 366 that extends into the balloon between the two sheets 363 and 364 and forms a fluid-tight seal therewith. The interior of the balloon can be inflated and deflated by introduction of the fluid through the tube 366. A conventional pinch off clamp 372 is mounted on the tube 369 to control fluid flow. The tube 366 is adapted to optionally be releasably retained in one or more slots (not shown) on the assembly. In alternative embodiments the pinch-off clamp 372 may be replaced with a stop-cock valve, as shown as element 328, or any other valve-type device able to control the flow of fluid within a tube. In one embodiment the stop-cock valve includes a barbed ended connector or a screw-type connector for efficient and cost effective connection to medical tubing or other medical devices.

Means is provided for removably securing the dissection balloon 361 to the tunneling rod or shaft 306 and may comprise an elongate tubular member or sleeve 376 which extends along the length of the balloon 361 and is disposed on one side of the balloon 361 which can be called the top side generally centrally of the balloon 361. The tubular member 376 is provided with a passage 377 therein through which the tunneling or guide rod or shaft 333 extends. As hereinbefore explained, this tubular member or sleeve 376 can be formed as a separate member which is bonded to the top sheet 363 or alternatively can be formed integral with the top sheet 363 with two heat seals being provided above and below to form the balloon sleeve 376 with the passage 377 therein. The tubular member 376 can be provided with spaced-apart elongate slits or perforations (not shown) extending along a line 378 in the tubular member 376 to facilitate separation of the balloon from the tunneling rod 333 as hereinafter described. With a such a construction it can be seen that the tunneling rod or blunt dissector or obturator 306 overlies the balloon 361 for advantageous features hereinafter described.

Figure 67:
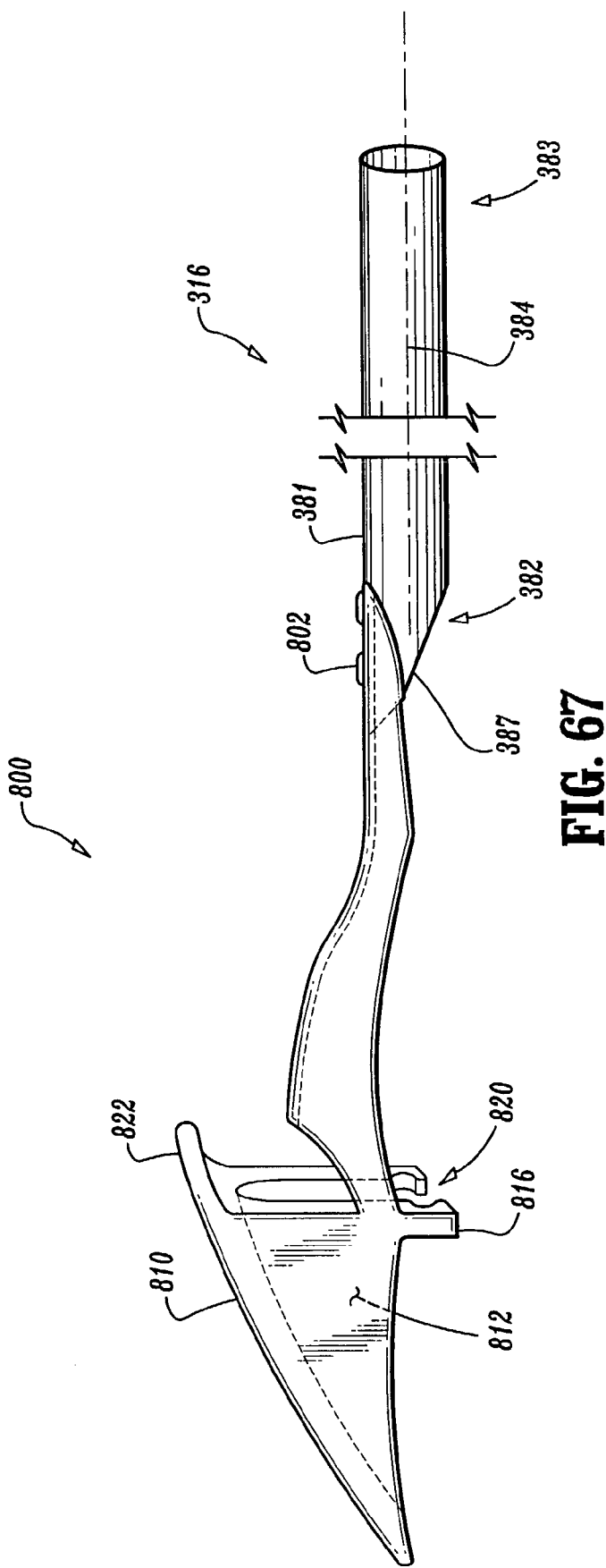
FIG. 67 is an isometric view of the balloon cover and balloon cover handle.
Figure 68:
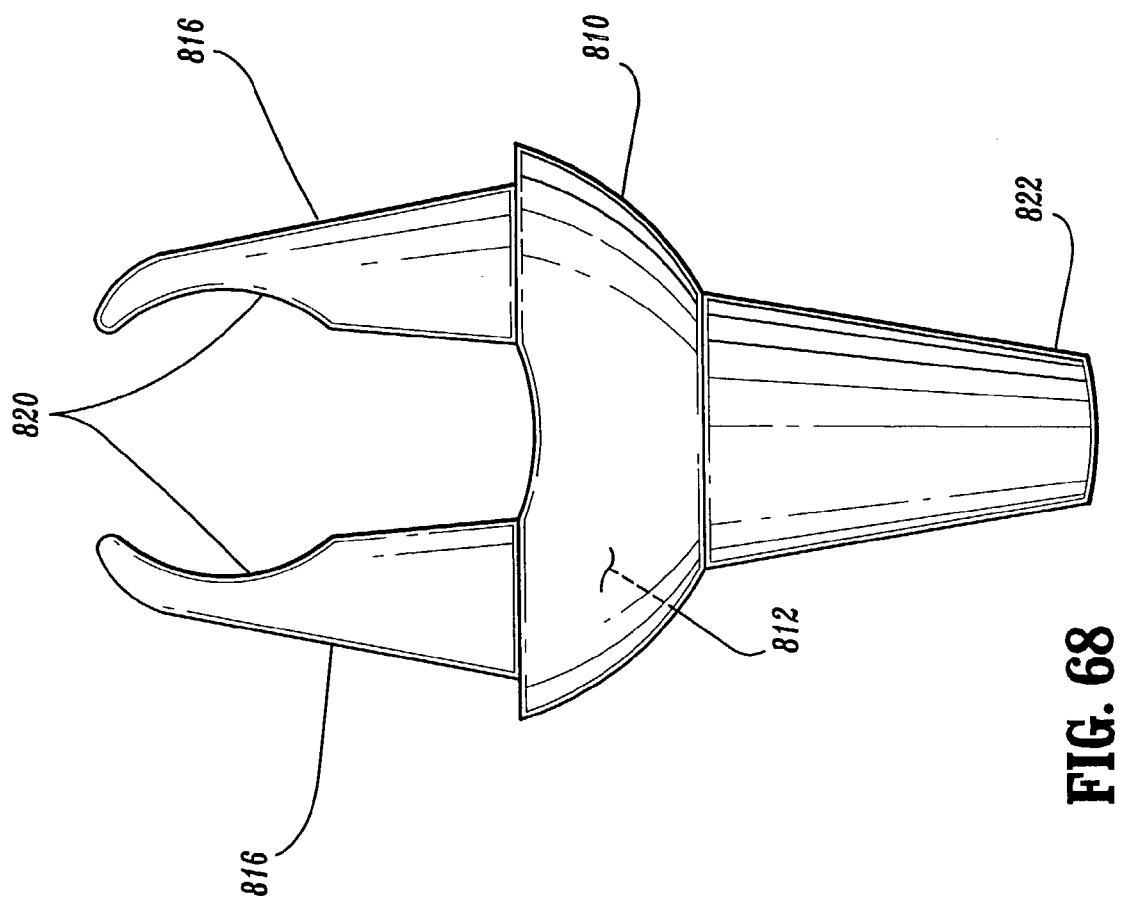
FIG. 68 is an end plan view from the proximal end of the balloon cover handle.

In reference to FIGS. 67 and 68 the balloon cover assembly comprises a balloon cover 316 and balloon cover lock and port shield 800 configured to cover at least one of the fluid ports 328, and 704 that are utilized to access either of the insufflation port or the skin seal balloon port. For purposes of discussion of this alternative embodiment the balloon cover assembly is comprised of a balloon cover tube 316 and a balloon cover lock and port shield 800.

Figure 58:
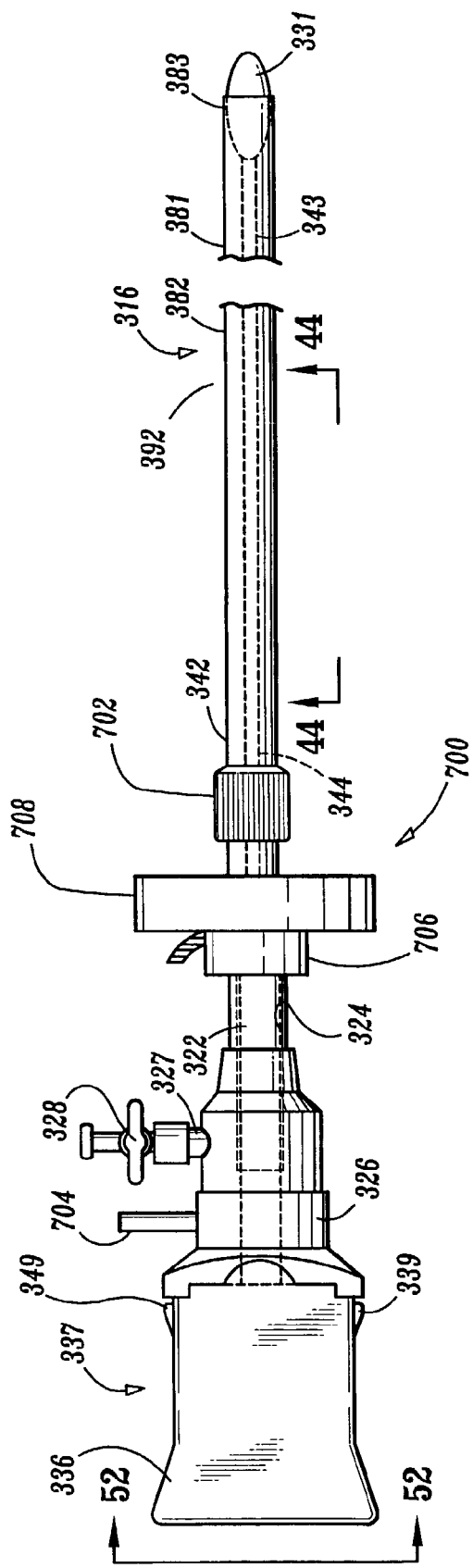
FIG. 58 is a side plan view of an alternative embodiment of the surgical dissector.
Figure 59:
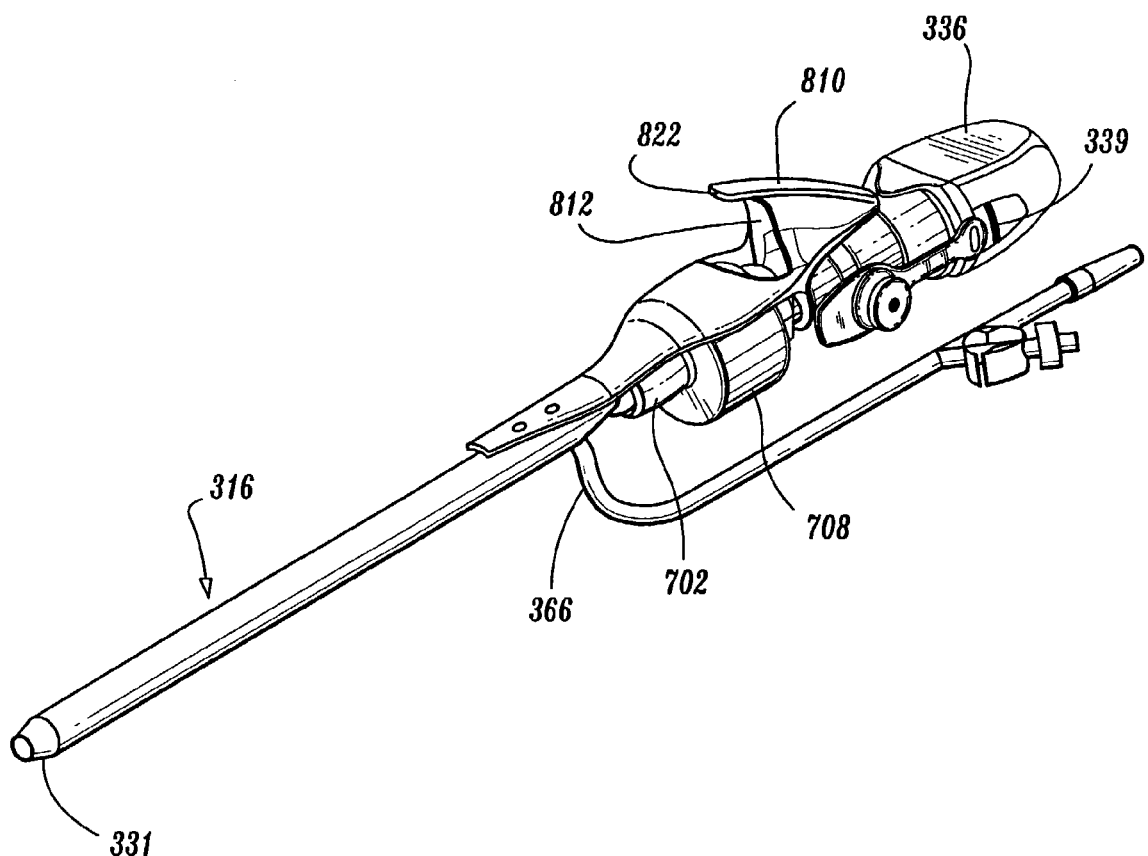
FIG. 59 is an isometric view of an alternative embodiment of a surgical dissector with a cannula incorporating the present invention in an assembled condition without the balloon cover handle.

The balloon cover 316 is generally identical to the balloon cover described above. As shown in FIGS. 57 and 58. The balloon cover assembly 316 comprises a semi-rigid tube 381 formed of a suitable material such as plastic and is provided with proximal and distal extremities 382 and 383. It is provided with a bore 384 which extends from the proximal extremity 382 to the distal extremity 383. The tube 381 is provided with a weakened region in the form of a partial slit 386 extending from the distal extremity 383 to the proximal extremity 382 of the tube 381 on the bottom side of the tube 381 as viewed in FIGS. 57 and 58. The tube 381 is truncated extending at a suitable angle, as for example 45° with respect to the axis of the bore 384.

The balloon cover assembly 316 also includes a balloon cover lock and port shield 804 which as shown can be formed as a separate part and is secured to the proximal extremity 382 of the tube 381 by a metal clip, plastic rivet, glue, thermal bond or any other manner of connection 802 known to those of ordinary skill in the art. In an alternative embodiment, the balloon cover and balloon cover lock and port shield 800 are integrally formed of a single piece of material.

The balloon cover lock and port shield 800 is provided with a tapered body 810 formed of a suitable material such as plastic which as shown in FIG. 67 is open on the bottom side to make accessible a longitudinally extending recess 812 which is semi-circular in cross-section. The recess is concave to form an oval shaped shell that extends in the proximal direction a distance sufficient to cover at least one of the fluid ports 327, 704 of the present invention. In a preferred embodiment the balloon cover lock and port shield 800 covers both fluid ports.

A pair of opposing jaws 816 (FIGS. 67 and 68) are provided on opposite sides of the balloon cover lock and port shield 800. The jaws 816 extend from the recessed shell of the balloon cover lock and port shield and are configured with arcuate camming surfaces 820. The camming surfaces 820 of the balloon cover lock and port shield 800 flex around and grip the round exterior surface of the cannula tube 321 to thereby secure or clamp the balloon cover lock and port shield to the cannulas. To remove the balloon cover lock and port shield a user applies sufficient pressure to a lifting hook 822 on the balloon cover lock and port shield 800 in a direction away from the cannula to overcome the friction fit exerted by the two opposing jaws 820 against and around the cannula tube 321. The balloon cover may than be removed by pulling proximally causing the tube to split at its weakened region.

Forming the balloon cover lock and port shield 800 in the above-described manner provides the advantage of shielding and preventing access to the fluid ports prior to removal of the balloon cover 381. Such an arrangement prevents inadvertent inflation of the balloon on the cannula tip prior to removal of the balloon cover 804 and protects the ports of the device from damage or debris.

Figure 69E:
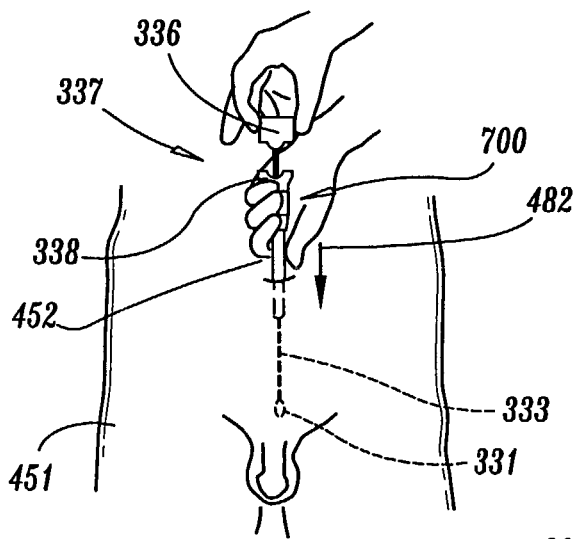

Operation and use of the surgical balloon dissection apparatus 700 in performing the method for developing an anatomic space for laparoscopic hernia repair in connection with the apparatus shown in FIGS. 56-68 may now be briefly described and follows in conjunction with the illustrations which are shown in FIG. 69A through FIG. 69G. The surgeon in connection with the present method identifies the appropriate tissue plane to be dissected, either by direct visualization of the tissue and/or by manual palpation. Let it be assumed that it is desired to perform a hernia repair on a patient 451 and that it is desired to create an extraperitoneal working space for performing the surgical repair. The surgeon makes a small incision 452 in the skin of the patient in the umbilicus or slightly lateral of the umbilicus. A retractor (not shown) can then be utilized to hold open the incision and to locate the rectus muscles that run longitudinally of the body of the patient on both sides of the umbilicus or navel. As soon as the rectus sheath has been located, an incision is made in the rectus sheath and muscle through the previously created incision. The surgeon then grasps the balloon dissection assembly 700 as shown in FIG. 69A and introduces the blunt end 331 into the incision to engage the anterior wall of the posterior rectus sheath. The balloon dissector assembly 700 is then advanced inferiorly and generally parallel to the two sets of rectus muscles as shown by the arrow 453 by using the posterior rectus sheath as a guide causing separation of tissue, passing beyond the arcuate line along the transversalis fascia to the level of the symphysis pubis. This can be readily accomplished with the balloon dissector assembly 700 because the balloon cover assembly 316 is latched to and generally rigidly connected to the distal extremity of the cannula member 302 of the device by having the jaws 816 provided on the tubular cover 381 seated around the shaft of the cannula tube 302 connection sufficient rigidity such that the surgeon can advance the device along the tissue plane.

The travel of the blunt tip 331 can be readily ascertained by the surgeon who can use his hand to palpate the abdominal region of the patient and thereby feel the blunt tip 331 as it is advanced to strike the symphysis pubis. The balloon dissector assembly 700 is then advanced a small additional amount so that the blunt tip 331 drops below the symphysis pubis 468.

The surgeon may then lift the balloon cover lock and port shield to disengage the jaws 816 from around the cannula tube 321 to thereby free the jaws from the cannula 302. Retracting the balloon cover assembly (316) in the direction of the arrow 454 in FIG. 69B, exposes the balloon within the patient. The balloon 361 is held in place by the tunneling shaft or rod 336 and exits through the slit 386 provided at the bottom of the tubular cover 381. The balloon cover thus serves as a tear away sheath. In one embodiment the balloon inflation tube 366 is retained in a slots (not shown) in the device so that it does not become entangled as the balloon cover assembly 316 is removed. This exposes the balloon 361 which has its side margins gathered or rolled inwardly. If rolled, rolls 461 may roll in a counterclockwise and clockwise direction so that they lie adjacent the tunneling rod 333. Also to provide optimum dissection as hereinafter described before the rolling up occurs, the forwardly extending protuberance 362 if present can be folded inwardly along a fold line 471 and the sidewardly extending lobe portions also can be folded inwardly along fold lines 472.

To inflate the balloon the pinch off clamp 372 or other valve is opened and a conventional syringe 476 containing a saline solution is connected to the tube or valve. The syringe 466 is then operated as shown by the arrow 467 to introduce the saline solution from the syringe 476 into the tubular member 366 and into the interior of the balloon 361 to gradually inflate the same. The valve or pinch off claim 372 ensures that saline solution cannot exit therefrom when the syringe 466 is removed. The syringe 476 after it has been emptied can be removed and refilled with a saline solution which is introduced into the balloon in the same manner to cause the side margins of the balloon 461 to unwrap in opposite directions as shown in FIG. 50 on opposite sides of the tunneling rod 333 until they become completely unwrapped. Typically, it may take several syringes of saline solution to cause the balloon 361 to completely unwrap and assume an inflated condition as shown in FIG. 50. As the balloon is being filled and unwrapping, it continues to separate or dissect tissue overlying the peritoneum to provide an extraperitoneal working space between the peritoneal and the overlying layers. Alternatively, gas may be used to fill the balloon instead of a liquid such as saline solution.

As hereinbefore described, the balloon 361 in plan has a symmetric manta ray-like configuration to provide the desired optimum extraperitoneal working space for the hernia repair. The forwardly extending protrusion 362 if provided on the balloon 361 dissects distally from the distal extremity of the blunt tip 331 of the guide rod 333 serves to provide good dissection of tissue in the area of Cooper's ligaments and also to dissect laterally around the inguinal rings. By utilizing a symmetric manta ray-like construction, it is possible to provide a balloon 361 with its wide side margins or lobe portions 361a and 361b which when inflated to cause forward movement of the balloon 361 to dissect downwardly around the inguinal rings and to wedge the balloon 361 in place. The forwardly extending protrusion 362 as it is inflated dissects down around Cooper's ligament. In this way, it is possible to obtain an extraperitoneal working space 478 which exposes all the desired anatomy at one time before reducing the hernia sac and proceeding with the hernia repair. By providing such a large extraperitoneal working space it is usually unnecessary to manually advance the dissection. The balloon is preferably shaped to properly match the necessary anatomy in which the procedure is to be performed. Hence, the balloon may assume a variety of different shapes and/or sizes. Since the balloon has a particular shape and is formed of a non-elastomeric material, the dissection will occur in the desired locations which would not necessarily be the case if the balloon were formed of an elastomeric material which would have a tendency to follow the path of least resistance. Additional assurance is provided for ensuring that dissection will occur in the desired locations because the balloon is held in place by the tunneling rod 333 underlying the symphysis pubis 468 as shown in FIG. 50.

After the desired tissue dissection has taken place by inflation of the balloon 361, the balloon is deflated by connecting the evacuation fitting 371 into an evacuation port (not shown) of an operating room suction system. The pinch clamp 372 is released to open the tube 369 to permit the saline solution, air, or gel which had been introduced into the balloon 361 to be sucked out to completely deflate the balloon from the inflated condition as shown in FIG. 69C. If desired the suction fitting, "Y" fitting and check valve may be replaced by a single stop cock.

After the balloon 361 has been deflated, the balloon assembly 312 can be grasped by the fill tube 366 as shown and the deflated balloon pulled out through the incision 452 in the direction as shown by the arrow 481 in FIG. 69D. The handle assembly 337 can be held in place by the other hand. The balloon 361, as it is being pulled off, its sleeve 376 separates from the tunneling or guide rod 331 by breaking of the linear perforations lying along the line 378. The guide rod 331 remains in place to preserve an easy entry into the extraperitoneal space which has been created. The balloon 361 is discarded.

After the balloon 361 has been removed, the left hand may be used to grasp the cannula 302 while the right hand engages the upper or first handle part 336 of the handle assembly. The fingers of the right hand then engage the latch members 339 on opposite sides to release the handle 336 from the cannula 302 permitting the cannula to be advanced into the incision in the direction of the arrow 482 shown in FIG. 69E. The removal of the guide rod 333 is continued and the forward movement of the skin seal is advanced to the desired position.

Figure 69F:
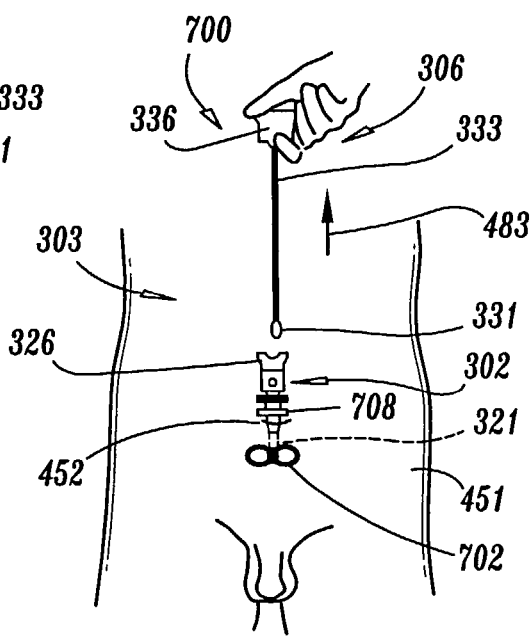
Figure 69G:
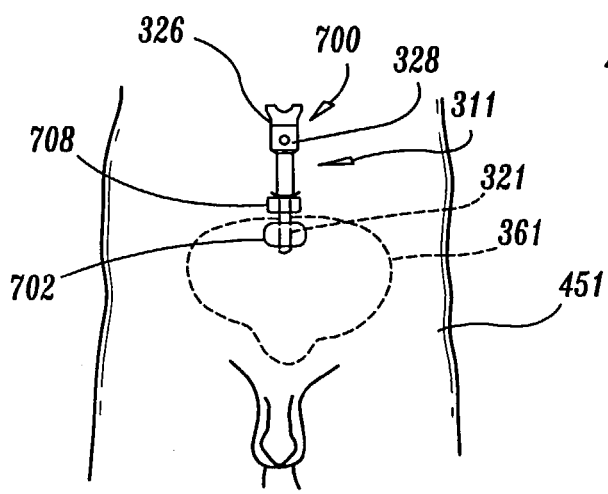

When the skin seal balloon 702 is between the two dissected layers of tissue, as shown in FIG. 69F the skin seal balloon is inflated with a bulb or syringe, and the resilient skin contact portion 708 of the skin seal assembly 701 moved into position and locked in place. Steps are taken to prevent gas escape from the skin seal balloon 702. These may include but are not limited to actuation of a stop-cock or a use of a conventional check valve.

After establishing the fluid tight seal, the tunneling rod 333 may be fully removed from the cannula. Removing the tunneling rod 333 after establishing the skin seal further decreases the likelihood of tissue being pinched between the blunt tip 331 of the tunneling rod and the distal edge of the cannula 302 because the inflated skin seal 702 displaces tissue from near the distal end of the cannula. When the tunneling rod 333 is removed from the patient a duck bill gas seal prevents the escape of gas from the space created by the tissue dissection balloon.

Removal of the tunneling rod 336 from the cannula 321 and the patient 451 is accomplished by continuing to retract the handle part 336 in the direction indicated by the arrow 483 as shown in FIG. 69F. As this pulling motion continues, the blunt tip 331 will engage the distal end of the tunneling rod guide assembly 600 causing a withdrawal force to be applied to the end collar 604 to thereby cause the fingers 610 to automatically release from the first shoulder 614. This permits the tunneling rod guide assembly 600 to be removed with the tunneling rod 333 through the cannula tube 321. This is possible because the blunt tip 331 has a diameter which can pass through the interior of the cannula tube 321 and through the valving provided in the housing 326 when the fingers drop to the second shoulder 616. In withdrawing the guide rod 333 carrying the tunneling rod guide assembly 600, it can be seen that it continues to be guided by the guide collar 608 and guide sleeve 602 and thus will remain centered with respect to the cannula tube 321 to avoid any pinching action at the distal end 323 of the cannula tube 321. The guide collar fingers 610 are substantially at the distal end of the tunneling rod guide assembly 600 and thus are inaccessible to the surgeon ensuring that he will not or can not move the guide collar 608 into the cannula tube 321 until the blunt tip 331 of the tunneling rod 333 is about to enter the cannula tube.

After removal of the tunneling device 306 and tunneling rod guide assemble 600 has been accomplished a source of insufflation gas such as carbon dioxide is connected to the stop-cock valve 328. The stop-cock valve 328 is opened to permit the carbon dioxide to insufflate the dissected extraperitoneal working space as indicated by the dotted lines 476 shown in FIG. 69G. The cannula 302 can then be utilized for introducing instruments of various types into the dissected extraperitoneal working space. The inflation gas cannot escape because of the valve and seal provided in the handle 326 of the cannula 302.

Additional cannulas can be introduced in various positions in the abdomen of the patient through which additional surgical instruments can be introduced for performing the surgical procedure to be performed in the extraperitoneal working space. The remainder of the hernia repair procedure to be accomplished in the extraperitoneal working space is substantially the same as hereinbefore described and therefore will not be described in detail. By way of example, let it be assumed that a hernia sac has been formed in the patient, as for example by passing down into the scrotum to form a typical indirect hernia. The hernia sac can be pulled out and ligated in a manner hereinbefore described. Thereafter, a piece of mesh as hereinbefore described can be introduced through another site and rolled out over the region through which the sac had previously passed. The mesh can then be stapled in place, as for example along the Cooper's ligament.

After the hernia repair has been completed, the extraperitoneal working space can be deflated by disconnecting the insufflation gas opening the stop cock valve 328 and bleeding the $CO_2$ contained therein to atmosphere to permit the abdominal wall layer to return to their normal positions to help retain the mesh which has been placed over the hernia site.

In connection with the formation of the extraperitoneal working space with the apparatus of the present invention, it has been found that it is desirable to have the guide rod 333 be in position in which it overlies the balloon 361 because this helps to ensure that the balloon dissection will occur in appropriate areas because the blunt tip 331 underlying the symphysis pubis is retained in the desired position even during the time that the balloon is unrolling during inflation. Positioning the guide rod 333 in this manner ensures that the balloon 361 will roll out in the opposite directions.

In order to make the apparatus more user friendly, the parts which are to be moved for operation with respect to other parts have been color coded, as for example they can be colored black with the remaining parts being of another color, such as gray or white. In this example, the latch parts 339 and 349 will be of black color because they must be moved to separate the handle parts.

The sizing of the blunt obturator tip 331 so it is smaller than the inner diameter of the cannula tube 321 and the operation of obturator assembly 600 help to ensure that tissue will not become entrapped or pinched between the tip 331 and the cannula tube 321. In addition, as hereinbefore described, the obturator tip 331 is tapered in both directions to a smaller dimension from the center to also minimize the possibility of any tissue being entrapped between the tip 331 and the cannula tube 321 and thereby ensuring that a shearing action will not occur.

If a stop-cock valve is utilized to control gas ingress and egress from the skin seal balloon 702 and the dissection balloon 312, several advantages over the prior art harness include, but are not limited to, ease of use, easier connection, and lower cost. Various connectors may attach to the opening of the stop-cock valve to facilitate connection to various hoses, pump-devices or syringes. These include a screw-type connector, a barbed connector, or a clamp-type connector. Valves, seals, connectors, clamps, and tubing are known by those of ordinary skill in the art and are therefore not described in great detail herein.

From the foregoing it can be seen that there has been provided an apparatus and method which is particularly suitable for developing an anatomic space such as an extraperitoneal working space between the abdominal wall and the peritoneum by dissecting tissue with the use of a non-elastomeric balloon. The balloon dissection apparatus has many features facilitating its use in developing such an anatomic space, particularly for developing an extraperitoneal working space for hernia repair. Although the foregoing invention has, for purposes of clarity of understanding, been described in some detail by way of illustration and example, it will be obvious that certain changes and modifications may be practiced which will still fall within the scope of the appended claim. It will also be understood that each feature of each embodiment discussed herein, and of each reference cited herein, can be used in combination with the features of any other embodiment.

What is claimed is:

1. An apparatus for separating tissue, comprising:
   a) a cannula tube having a lumen;
   b) an obturator rod having a distal end, the obturator rod being received in the lumen of the cannula tube;
   c) a guide having a distal end, the guide being movably received between the obturator rod and the cannula tube so that the distal end of the obturator rod engages the distal end of the guide when the obturator rod is moved in a proximal direction, the guide including:
   a guide tube having a distal end, the guide tube being disposed around the obturator rod, an end collar fixedly disposed at the distal end, a first collar fixedly disposed on the guide tube proximally of the end collar, and a guide collar slidably disposed on the guide tube;
   the guide collar having a proximal portion for engaging the first collar, the guide collar transitional from a first state defined by engagement of the proximal portion with a first region of the first collar having a first diameter to a second state defined by engagement of the proximal portion with a second region of the first collar having a second diameter different from the first diameter, wherein relative proximal movement between the obturator rod and the guide transitions the guide collar from the first state to the second state, wherein the guide collar is movable within the lumen of the cannula tube when in the second state; and
   d) the guide collar being expandable to engage the cannula tube when the guide collar is in the first state; and
   e) a balloon mounted on the obturator rod.

2. The apparatus of claim 1, wherein the first collar comprises a shoulder defining the first region and the guide collar is adapted for expansion upon engagement with the shoulder.

3. The apparatus of claim 2, wherein the guide collar comprises at least one flexible member for expanding upon engagement of the shoulder.

4. The apparatus of claim 2, wherein the guide collar is sized so as to be received in the lumen of the cannula tube before expansion.

5. The apparatus of claim 2, wherein the shoulder is sized so that the guide collar is larger than the lumen of the cannula tube after expansion.

6. The apparatus of claim 2, wherein further movement of the obturator rod moves the guide tube with respect to the guide collar, releasing the guide collar from engagement with the shoulder transitioning the guide collar from the first state to the second state engaging the guide collar with another shoulder defining the second region.

7. The apparatus of claim 1, wherein further movement of the obturator rod releases the guide from engagement with the cannula tube.

8. The apparatus of claim 1, wherein the guide collar includes at least one finger adapted to engage at least the distal end of the cannula tube when the guide collar is in the first state, the at least one finger adapted to transition the guide collar from the first state to the second state with further movement of the obturator rod in the proximal direction when the at least one finger engages the distal end of the cannula tube.

9. The apparatus of claim 1, wherein guide collar includes at least one finger adapted to disengage from an inner surface of the cannula tube when the guide collar transitions from the first state to the second state.

10. The apparatus of claim 1, wherein the guide collar is configured to engage a distal end of the cannula tube when the guide collar is in the first state.

11. A method of guiding a tunneling shaft of a tissue separation apparatus, comprising:
   a) providing a cannula tube having a lumen, an obturator rod received in the lumen of the cannula tube; a guide movably received between the obturator and the cannula, the guide including:

a guide tube having a distal end, the guide tube being disposed around the obturator rod, an end collar fixedly disposed at the distal end, a first collar fixedly disposed on the guide tube proximally of the end collar, and a guide collar slidably disposed on the guide tube;

the guide collar having a proximal portion for engaging the first collar, the guide collar transitional from a first state defined by engagement of the proximal portion with a first region of the first collar having a first diameter to a second state defined by engagement of the proximal portion with a second region of the first collar having a second diameter different from the first diameter, wherein relative proximal movement between the obturator rod and the guide transitions the guide collar from the first state to the second state, wherein the guide collar is movable within the lumen of the cannula tube when in the second state;

b) moving the obturator rod in a proximal direction so that the guide collar engages the first region and expands engaging an inner surface of the cannula tube; and c) applying a force to the obturator rod so that the guide collar engages the second region releasing the guide from engagement with the inner surface of the cannula tube.

12. The method of claim 11, wherein the step of moving the obturator rod includes engaging a distal end of the guide with a distal end of the obturator rod.

13. The method of claim 11, wherein the step of applying a force includes moving the guide tube with respect to the guide collar, releasing the guide collar from engagement with the cannula tube.

14. The method of claim 13, wherein the first collar includes a shoulder defining the first region and wherein the step of expanding the guide collar comprises engaging a proximal end of the guide collar with the shoulder.

15. The method of claim 14, wherein the guide collar includes a flexible portion at the proximal end and the step of expanding the guide collar comprises engaging the flexible portion with the shoulder.

16. The method of claim 11, further comprising removing the obturator rod from the cannula tube after the guide is released.

17. The apparatus of claim 11, wherein the obturator rod includes an engagement member disposed on a distal end of the obturator rod, the engagement member adapted to engage a distal end of the guide.

18. An apparatus for separating tissue, comprising:
a) a cannula tube having a lumen;
b) an obturator rod having a distal end, the obturator rod being received in the lumen of the cannula tube; and
c) a guide movably received between the obturator and the cannula so that the obturator rod is substantially centered in the cannula tube when the obturator rod is moved in a proximal direction, the guide including:

a guide tube having a distal end, the guide tube being disposed around the obturator rod, an end collar fixedly disposed at the distal end, a first collar fixedly disposed on the guide tube proximally of the end collar, and a guide collar slidably disposed on the guide tube;

the guide collar having a proximal portion for engaging the first collar, the guide collar transitional from a first state defined by engagement of the proximal portion with a first region of the first collar having a first diameter to a second state defined by engagement of the proximal portion with a second region of the first collar having a second diameter different from the first diameter, wherein relative proximal movement between the obturator rod and the guide transition the guide collar from the first state to the second state, wherein the guide collar is movable within the lumen of the cannula tube when in the second state; and d) the guide collar being movable between an expanded first position in engagement with an inner surface of the cannula tube defining the first state and a second position released from engagement with the cannula tube defining the second state.

19. The apparatus of claim 18, wherein the guide collar is movable from an initial position released from engagement with the cannula tube to the first position.

20. The apparatus of claim 18, wherein the guide collar has a distal end, the guide collar being disposed so that a distal end of the obturator rod engages the distal end of the guide collar when the obturator rod is moved in a proximal direction.

21. The apparatus of claim 20, wherein the guide collar transitions from the first state to the second state when the distal end of the obturator rod engages the distal end of the guide.

22. The apparatus of claim 18, wherein the first collar comprises a shoulder defining the first region and the guide collar is adapted for expansion upon engagement with the shoulder.

23. The apparatus of claim 22, wherein the guide collar comprises at least one flexible member for expanding upon engagement of the shoulder.

24. The apparatus of claim 18, wherein further movement of the obturator rod releases the guide from engagement with the cannula tube.

25. The apparatus of claim 24, wherein further movement of the obturator rod moves the guide tube with respect to the guide collar, releasing the guide collar from engagement with the shoulder.

26. The apparatus of claim 18, wherein the guide collar is adapted to remain in the second state when the guide moves in the proximal direction relative to the cannula tube after transitioning from the first state to the second state.

* * * * *